US010414743B2

(12) United States Patent
Taugerbeck et al.

(10) Patent No.: US 10,414,743 B2
(45) Date of Patent: *Sep. 17, 2019

(54) POLYMERIZABLE COMPOUNDS AND THE USE THEREOF IN LIQUID-CRYSTAL DISPLAYS

(71) Applicant: MERCK PATENT GMBH, Darmstadt (DE)

(72) Inventors: Andreas Taugerbeck, Darmstadt (DE); Achim Goetz, Seoul (KR); Alexander Hahn, Biebesheim (DE); Martin Engel, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 226 days.

This patent is subject to a terminal disclaimer.

(21) Appl. No.: 15/014,890

(22) Filed: Feb. 3, 2016

(65) Prior Publication Data
US 2016/0159763 A1   Jun. 9, 2016

Related U.S. Application Data

(62) Division of application No. 13/980,134, filed as application No. PCT/EP2011/006575 on Dec. 27, 2011, now Pat. No. 9,279,082.

(30) Foreign Application Priority Data

Jan. 20, 2011 (EP) ..................... 11000413
Feb. 4, 2011 (EP) ..................... 11000877

(51) Int. Cl.
| | | |
|---|---|---|
| *C07D 311/22* | (2006.01) | |
| *C09K 19/34* | (2006.01) | |
| *C09K 19/44* | (2006.01) | |
| *C09K 19/06* | (2006.01) | |
| *C07D 311/14* | (2006.01) | |
| *C09K 19/04* | (2006.01) | |
| *C09K 19/12* | (2006.01) | |
| *C09K 19/30* | (2006.01) | |
| *C09K 19/54* | (2006.01) | |

(52) U.S. Cl.
CPC .......... *C07D 311/22* (2013.01); *C07D 311/14* (2013.01); *C09K 19/06* (2013.01); *C09K 19/3402* (2013.01); *C09K 19/44* (2013.01); *C09K 2019/0448* (2013.01); *C09K 2019/123* (2013.01); *C09K 2019/301* (2013.01); *C09K 2019/3004* (2013.01); *C09K 2019/3009* (2013.01); *C09K 2019/3016* (2013.01); *C09K 2019/3425* (2013.01); *C09K 2019/548* (2013.01)

(58) Field of Classification Search
CPC ... C07D 311/04; C07D 311/76; C07D 311/08; C07D 311/12; C07D 311/14; C07D 311/16; C07D 311/18; C07D 311/22; C07D 311/30; C07D 311/36; C09K 19/3402; C09K 2019/3425; C09K 2019/0448
See application file for complete search history.

(56) References Cited

U.S. PATENT DOCUMENTS

| | | | | |
|---|---|---|---|---|
| 5,574,062 A * | 11/1996 | Hashimoto | .......... | C07D 311/16 514/457 |
| 8,592,007 B2 * | 11/2013 | Goetz | ................ | C09K 19/3402 252/299.61 |
| 9,279,082 B2 * | 3/2016 | Taugerbeck | ....... | C09K 19/3402 |
| 9,580,653 B2 * | 2/2017 | Archetti | ................ | C09K 19/04 |
| 9,714,381 B2 * | 7/2017 | Archetti | ............... | C09K 19/542 |
| 9,726,933 B2 * | 8/2017 | Archetti | ............... | C09K 19/063 |
| 9,982,194 B2 * | 5/2018 | Klasen-Memmer | ........................ | C09K 19/062 |
| 2003/0212009 A1 * | 11/2003 | Hendler | ................... | A61K 8/14 514/27 |
| 2005/0096381 A1 * | 5/2005 | Kohen | ................ | C07D 311/36 514/456 |
| 2005/0143588 A1 * | 6/2005 | Heaton | ................ | C07D 311/36 549/403 |
| 2005/0244718 A1 | 11/2005 | Poetsch et al. | | |
| 2009/0062380 A1 * | 3/2009 | Grynkiewicz | ....... | A61K 31/352 514/456 |
| 2009/0170927 A1 * | 7/2009 | Bezwada | ................ | A61L 27/18 514/455 |
| 2009/0197943 A1 * | 8/2009 | Chan | ................... | C07D 311/30 514/456 |

(Continued)

FOREIGN PATENT DOCUMENTS

| | | |
|---|---|---|
| PL | 200212 B1 * | 12/2008 |
| WO | 2004/003103 A1 | 1/2004 |

(Continued)

OTHER PUBLICATIONS

Zheng et al., "Synthesis and cytotoxic activity of genistein derivatives", Oct. 14, 2009, Medicinal Chemistry Research, vol. 19, 1296-1306.*

(Continued)

*Primary Examiner* — Cynthia H Kelly
*Assistant Examiner* — Anna Malloy
(74) *Attorney, Agent, or Firm* — Millen White Zelano and Branigan, PC; Csaba Henter

(57) ABSTRACT

The present invention relates to polymerizable compounds, to processes and intermediates for the preparation thereof, and to the use thereof for optical, electro-optical and electronic purposes, in particular in liquid-crystal (LC) media and LC displays, especially in LC displays of the PS ("polymer sustained") or PSA ("polymer sustained alignment") type.

20 Claims, No Drawings

(56) References Cited

U.S. PATENT DOCUMENTS

2010/0137425 A1* 6/2010 Bergan ............... C07D 311/38
   514/456
2011/0028667 A1 2/2011 Ritter et al.
2011/0205482 A1 8/2011 Goetz et al.
2015/0166890 A1* 6/2015 Archetti ............. C09K 19/3098
   252/299.63

FOREIGN PATENT DOCUMENTS

WO 2009/074520 A2 6/2009
WO 2010/049044 A1 5/2010

OTHER PUBLICATIONS

Harborne et al., "Occurrence of the isoflavone afromosin in cabreuva wood", Mar. 1963, Journal of Organic Chemistry, vol. 28, 881-882.*
Liu et al., "A New Flavonoid from Selaginella tamariscina Spring", Jan. 14, 2010, Chemical and Pharmaceutical Bulletin, vol. 58, Iss 4, 549-551.*
Simpson, T.H. "Derivatives of 6,8-Dihydroxyflavone", Aug. 1963, Journal of Organic Chemistry, vol. 28, No. 8, 2107-2110.*
Zhang et al., "Preparation and Characterization of Imprinted Porous Materials with High Selectivity for Luteolin", Aug. 25, 2009, Chemical Engineering and Technology, vol. 32, No. 10, 1512-1519.*
Chawia et al. "TLC Separation and Identification of Some Flavonoid C-Glycosides", Aug. 1976, Chromatographia, vol. 9, No. 8, 408-409.*
Montoro et al., "Metabolic profiling of roots of liquorice (*Glycyrrhiza glabra*) from different geographical areas by ESI/MS/MS and determination of major metabolites by LC-ESI/MS and LC-ESI/MS/MS", Oct. 14, 2010, Journal of Pharmaceutical and Biomedical Analysis, vol. 54, 535-544.*
English translation of PL200212. (Year: 2008).*
Lee et al., "Targeted Degradation of the Aryl Hydrocarbon Receptor by the PROTAC Approach: A Useful Chemical Genetic Tool", 2007, ChemBioChem, 8, 2058-2062. (Year: 2007).*
Ishikawa et al., "Ring-Expansion of 2-Methylbenzo[b]Furan to 3-Hydroxychromen-4-One: A Potential Approach to a Flavonol Skeleton", 1997, Heterocycles, vol. 45, Nol. 11, 2273-2276. (Year: 1997).*
Li et al., "Synthesis and Cytotoxic Evaluation of a Series of Genistein Derivatives", 2006, Chemistry & Biodiversity, vol. 3, 463-472. (Year: 2006).*
Bezwada, Rao S., "Absorbable polymers from soybean isoflavonoids for biomedical applications", 2009, PMSE Preprints, vol. 101, 1042-1043. (Year: 2009).*
Zhang et al., "Synthesis of biflavones and their interaction with DNA", 2009, Acta Pharmaceutica Sinica, vol. 44 Iss. 8, 873-878. (Year: 2009).*
Wang et al., "Genistein derivatives as selective estrogen receptor modulators: Sonochemical synthesis and in vivo anti-osteoporotic action", 2005, Bioorganic & Medicinal Chemistry, vol. 13, 4880-4890. (Year: 2005).*
Lapcik et al., "Immunoassay for biochanin A", 2004, Journal of Immunological Methods, vol. 294, 155-163. (Year: 2004).*
Wang et al., "Hydrothermal syntheses and structures of first examples of lanthanide 7,8,4'-tricarboxymethoxyisoflavone coordination polymers", 2009, Journal of Molecular Structure, 938, 214-220. (Year: 2009).*
Hidari et al., "Identification and characterization of flavonoids as sialyltransferase inhibitors", 2009, Biochemical and Biophysical Research Communications, 382, 609-613. (Year: 2009).*
Cao et al., "Bioactive flavones and biflavones from Selaginella moellendorffii Hieron", 2010, Fitoterapia, 81, 253-258. (Year: 2010).*
Cheng et al., "Novel synthetic luteolin analogue-caused sensitization of tumor necrosis factor-a-induced apoptosis in human tumor cells", 2008, Organic & Biomolecular Chemistry Communcation, vol. 6, 4102-4104. (Year: 2008).*
Bennetau-Pelissero et al., "Synthesis of Haptens and Conjugates for ELISAs of Phytoestrogens. Development of the Immunological Tests", 2000, J. Agric. Food Chem., vol. 48, 305-311. (Year: 2000).*
Lin et al., "First Total Synthesis of Protoapigenone and Its Analogues as Potent Cytotoxic Agents", 2007, Journal of Medicinal Chemistry, vol. 50, 3921-3927. (Year: 2007).*
Xu et al., "Cytosporones, coumarins, and an alkaloid from the endophytic fungus *Pestalotiopsis* sp. isolated from the Chinese mangrove plant *Rhizophora mucronata*", 2009, Bioorganic & Medicinal Chemistry, vol. 17, 7362-7367. (Year: 2009).*
St. Denis et al., "Novel Synthesis of the Isoflavone Genistein", 2010, Synthesis, No. 10, 1590-1592. (Year: 2010).*
International Search Report for PCT/EP2011/006575 (dated Apr. 23, 2012).

* cited by examiner

POLYMERIZABLE COMPOUNDS AND THE USE THEREOF IN LIQUID-CRYSTAL DISPLAYS

The present invention relates to polymerisable compounds, to processes and intermediates for the preparation thereof, and to the use thereof for optical, electro-optical and electronic purposes, in particular in liquid-crystal (LC) media and LC displays, especially in LC displays of the PS ("polymer sustained") or PSA ("polymer sustained alignment") type.

BACKGROUND OF THE INVENTION

The liquid-crystal displays (LC displays) used at present are usually those of the TN ("twisted nematic") type. However, these have the disadvantage of a strong viewing-angle dependence of the contrast.

In addition, so-called VA ("vertically aligned") displays are known which have a broader viewing angle. The LC cell of a VA display contains a layer of an LC medium between two transparent electrodes, where the LC medium usually has a negative value of the dielectric (DC) anisotropy. In the switched-off state, the molecules of the LC layer are aligned perpendicular to the electrode surfaces (homeotropically) or have a tilted homeotropic alignment. On application of an electrical voltage to the two electrodes, a realignment of the LC molecules parallel to the electrode surfaces takes place.

Furthermore, OCB ("optically compensated bend") displays are known which are based on a birefringence effect and have an LC layer with a so-called "bend" alignment and usually positive (DC) anisotropy. On application of an electrical voltage, a realignment of the LC molecules perpendicular to the electrode surfaces takes place. In addition, OCB displays normally contain one or more birefringent optical retardation films in order to prevent undesired transparency to light of the bend cell in the dark state. OCB displays have a broader viewing angle and shorter response times compared with TN displays.

Also known are so-called IPS ("in-plane switching") displays, which contain an LC layer between two substrates, where the two electrodes are arranged on only one of the two substrates and preferably have intermeshed, comb-shaped structures. On application of a voltage to the electrodes, an electric field which has a significant component parallel to the LC layer is thereby generated between them. This causes realignment of the LC molecules in the layer plane.

Furthermore, so-called FFS ("fringe-field switching") displays have been proposed (see, inter alia, S. H. Jung et al., Jpn. J. Appl. Phys., Volume 43, No. 3, 2004, 1028), which likewise contain two electrodes on the same substrate, but, in contrast to IPS displays, only one of these is in the form of an electrode which is structured in a comb-shaped manner, and the other electrode is unstructured. A strong, so-called "fringe field" is thereby generated, i.e. a strong electric field close to the edge of the electrodes, and, throughout the cell, an electric field which has both a strong vertical component and also a strong horizontal component. Both IPS displays and also FFS displays have a low viewing-angle dependence of the contrast.

In VA displays of the more recent type, uniform alignment of the LC molecules is restricted to a plurality of relatively small domains within the LC cell. Disclinations may exist between these domains, also known as tilt domains. VA displays having tilt domains have, compared with conventional VA displays, a greater viewing-angle independence of the contrast and the grey shades. In addition, displays of this type are simpler to produce since additional treatment of the electrode surface for uniform alignment of the molecules in the switched-on state, such as, for example, by rubbing, is no longer necessary. Instead, the preferential direction of the tilt or pretilt angle is controlled by a special design of the electrodes.

In so-called MVA ("multidomain vertical alignment") displays, this is usually achieved by the electrodes having protrusions which cause a local pretilt. As a consequence, the LC molecules are aligned parallel to the electrode surfaces in different directions in different, defined regions of the cell on application of a voltage. "Controlled" switching is thereby achieved, and the formation of interfering disclination lines is prevented. Although this arrangement improves the viewing angle of the display, it results, however, in a reduction in its transparency to light. A further development of MVA uses protrusions on only one electrode side, while the opposite electrode has slits, which improves the transparency to light. The slitted electrodes generate an inhomogeneous electric field in the LC cell on application of a voltage, meaning that controlled switching is still achieved. For further improvement of the transparency to light, the separations between the slits and protrusions can be increased, but this in turn results in a lengthening of the response times. In so-called PVA ("patterned VA") displays, protrusions are rendered completely superfluous in that both electrodes are structured by means of slits on the opposite sides, which results in increased contrast and improved transparency to light, but is technologically difficult and makes the display more sensitive to mechanical influences ("tapping", etc.). For many applications, such as, for example, monitors and especially TV screens, however, a shortening of the response times and an improvement in the contrast and luminance (transmission) of the display are demanded.

A further development are the so-called PS or PSA ("polymer sustained" or "polymer sustained alignment") displays, for which the term "polymer stabilised" is also occasionally used. In these, a small amount (for example 0.3% by weight, typically <1% by weight) of one or more polymerisable compound(s) is added to the LC medium and, after introduction into the LC cell, is polymerised or cross-linked in situ, usually by UV photopolymerisation, between the electrodes with or without an applied electrical voltage. The polymerisation is carried out at a temperature where the LC medium exhibits a liquid crystal phase, usually at room temperature. The addition of polymerisable mesogenic or liquid-crystalline compounds, also known as reactive mesogens or "RMs", to the LC mixture has proven particularly suitable.

Unless indicated otherwise, the term "PSA" is used below as representative of PS displays and PSA displays.

In the meantime, the PS(A) principle is being used in diverse classical LC displays. Thus, for example, PSA-VA, PSA-OCB, PSA-IPS, PSA-FFS and PSA-TN displays are known. The polymerisation of the polymerisable compound(s) preferably takes place with an applied electrical voltage in the case of PSA-VA and PSA-OCB displays, and with or without, preferably without, an applied electrical voltage in the case of PSA-IPS displays. As can be demonstrated in test cells, the PS(A) method results in a pretilt in the cell. In the case of PSA-OCB displays, for example, it is possible for the bend structure to be stabilised so that an offset voltage is unnecessary or can be reduced. In the case of PSA-VA displays, the pretilt has a positive effect on response times. For PSA-VA displays, a standard MVA or PVA pixel and electrode layout can be used. In addition, however, it is also possible, for example, to manage with only one structured electrode side and no protrusions, which significantly simplifies production and at the same time results in very good contrast at the same time as very good transparency to light.

Furthermore, the so-called posi-VA displays ("positive VA") have proven to be a particularly suitable mode. Like in classical VA displays, the initial orientation of the LC molecules in posi-VA displays is homeotropic, i.e. substantially perpendicular to the substrates, in the initial state when no voltage is applied. However, in contrast to classical VA displays, in posi-VA displays LC media with positive dielectric anisotropy are used. Like in the usually used IPS displays, the two electrodes in posi-VA displays are arranged on only one of the two substrates, and preferably exhibit intermeshed and comb-shaped (interdigital) structures. By application of a voltage to the interdigital electrodes, which create an electrical field that is substantially parallel to the layer of the LC medium, the LC molecules are transferred into an orientation that is substantially parallel to the substrates. In posi-VA displays, too, it a polymer stabilisation (PSA) has proven to be advantageous, i.e. the addition of RMs to the LC medium, which are polymerised in the cell, whereby a significant reduction of the switching times could be realised.

PSA-VA displays are described, for example, in JP 10-036847 A, EP 1 170 626 A2, U.S. Pat. Nos. 6,861,107, 7,169,449, US 2004/0191428 A1, US 2006/0066793 A1 and US 2006/0103804 A1. PSA-OCB displays are described, for example, in T.-J-Chen et al., Jpn. J. Appl. Phys. 45, 2006, 2702-2704 and S. H. Kim, L.-C-Chien, Jpn. J. Appl. Phys. 43, 2004, 7643-7647. PSA-IPS displays are described, for example, in U.S. Pat. No. 6,177,972 and Appl. Phys. Lett. 1999, 75(21), 3264. PSA-TN displays are described, for example, in Optics Express 2004, 12(7), 1221.

Like the conventional LC displays described above, PSA displays can be operated as active-matrix or passive-matrix displays. In the case of active-matrix displays, individual pixels are usually addressed by integrated, nonlinear active elements, such as, for example, transistors (for example thin-film transistors ("TFTs")), while in the case of passive-matrix displays, individual pixels are usually addressed by the multiplex method, as known from the prior art.

In particular for monitor and especially TV applications, optimisation of the response times, but also of the contrast and luminance (thus also transmission) of the LC display continues to be demanded. The PSA method can provide crucial advantages here. In particular in the case of PSA-VA, PSA-IPS, PSA-FFS and PSA-posi-VA displays, a shortening of the response times, which correlate with a measurable pretilt in test cells, can be achieved without significant adverse effects on other parameters.

In the prior art, use is made, for example, of polymerisable compounds of the following formula:

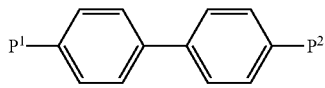

in which P denotes a polymerisable group, usually an acrylate or methacrylate group, as described, for example, in U.S. Pat. No. 7,169,449.

However, the problem arises that not all combinations consisting of LC mixture (also referred to as "LC host mixture" below)+polymerisable component (typically RMs) are suitable for PSA displays since, for example, an inadequate tilt or none at all becomes established or since, for example, the so-called "voltage holding ratio" (VHR or HR) is inadequate for TFT display applications. In addition, it has been found that, on use in PSA displays, the LC mixtures and RMs known from the prior art still have some disadvantages. Thus, not every known RM which is soluble in LC mixtures is suitable for use in PSA displays. In addition, it is often difficult to find a suitable selection criterion for the RM besides direct measurement of the pretilt in the PSA display. The choice of suitable RMs becomes even smaller if polymerisation by means of UV light without the addition of photoinitiators is desired, which may be advantageous for certain applications.

In addition, the selected combination of LC host mixture/RM should have the lowest possible rotational viscosity and the best possible electrical properties. In particular, it should have the highest possible VHR. In PSA displays, a high VHR after irradiation with UV light is particularly necessary since UV exposure is a requisite part of the display production process, but also occurs as normal exposure during operation of the finished display.

In particular, it would be desirable to have available novel materials for PSA displays which produce a particularly small pretilt angle. Preferred materials here are those which produce a lower pretilt angle during polymerisation for the same exposure time than the materials known to date, and/or through the use of which the (higher) pretilt angle that can be achieved with known materials can already be achieved after a shorter exposure time. The production time ("tact time") of the display could thus be shortened and the costs of the production process reduced.

A further problem in the production of PSA displays is the presence or removal of residual amounts of unpolymerised RMs, in particular after the polymerisation step for production of the pretilt angle in the display. For example, unreacted RMs of this type may adversely affect the properties of the display by, for example, polymerising in an uncontrolled manner during operation after finishing of the display.

Thus, the PSA displays known from the prior art often exhibit the undesired effect of so-called "image sticking" or "image burn", i.e. the image produced in the LC display by temporary addressing of individual pixels still remains visible even after the electric field in these pixels has been switched off or after other pixels have been addressed.

This "image sticking" can occur on the one hand if LC host mixtures having a low VHR are used. The UV component of daylight or the backlighting can cause undesired decomposition reactions of the LC molecules therein and thus initiate the production of ionic or free-radical impurities. These may accumulate, in particular, at the electrodes or the alignment layers, where they may reduce the effective applied voltage. This effect can also be observed in conventional LC displays without a polymer component.

In addition, an additional "image sticking" effect caused by the presence of unpolymerised RMs is often observed in PSA displays. Uncontrolled polymerisation of the residual RMs is initiated here by UV light from the environment or by the backlighting. In the switched display areas, this changes the tilt angle after a number of addressing cycles. As a result, a change in transmission in the switched areas may occur, while it remains unchanged in the unswitched areas.

It is therefore desirable for the polymerisation of the RMs to proceed as completely as possible during production of the PSA display and for the presence of unpolymerised RMs in the display to be excluded as far as possible or reduced to a minimum. To this end, materials are required which enable highly effective and complete polymerisation. In addition, controlled reaction of these residual amounts would be desirable. This would be simpler if the RM polymerised more rapidly and effectively than the materials known to date.

There is thus still a great demand for PSA displays, in particular of the VA and OCB type, and LC media and polymerisable compounds for use in such displays, which do not exhibit the disadvantages described above or only do so to a small extent and have improved properties. In particular, there is a great demand for PSA displays, and materials for use in PSA displays, which enable a high specific resistance at the same time as a large working-temperature range, short response times, even at low temperatures, and a low threshold voltage, a low pretilt angle, a multiplicity of grey shades, high contrast and a broad viewing angle, and have high values for the "voltage holding ratio" (VHR) after UV exposure.

The invention is based on the object of providing novel suitable materials, in particular RMs and LC media comprising same, for use in PSA displays, which do not have the disadvantages indicated above or do so to a reduced extent, polymerise as rapidly and completely as possible, enable a low pretilt angle to be established as quickly as possible, reduce or prevent the occurrence of "image sticking" in the display, and preferably at the same time enable very high specific resistance values, low threshold voltages and short response times.

A further object of the invention is the provision of novel RMs, in particular for optical, electro-optical and electronic applications, and of suitable processes and intermediates for the preparation thereof.

In particular, the invention is based on the object of providing polymerisable compounds which produce a greater maximum pretilt after photopolymerisation, which results in the desired pretilt being achieved more quickly and thus in significantly shortened times for production of the LC display.

This object has been achieved in accordance with the invention by materials and processes as described in the present application. In particular, it has been found, surprisingly, that the use of multireactive polymerisable compounds according to the invention, which are based on coumarine or flavone derivatives and contain two or more, preferably three or more polymerisable groups, wherein at least two polymerizable groups are attached to the same ring, in PSA displays facilitates particularly low pretilt angles and fast establishment of the desired tilt angles. This has been demonstrated in connection with an LC medium by means of pretilt measurements. In particular, a pretilt has been achieved without the addition of photoinitiator. In addition, the compounds according to the invention exhibit significantly faster generation of the pretilt angle compared with the materials known from the prior art, as has been demonstrated by exposure time-dependent measurements of the pretilt angle. In addition, the polymerisable compounds according to the invention exhibit a significantly higher polymerisation rate, causing smaller unreacted residual amounts to remain in the cell. The electro-optical properties of the cell are thus improved, and in addition controlled reaction of these residual amounts becomes simpler.

Polymerisable coumarine derivatives have been described in the prior art for other purposes. WO 2004/003103 A1 discloses luminescent polymerisable compounds which may also contain a coumarine group that is fused to a benzene ring like those of formula If1 and If2

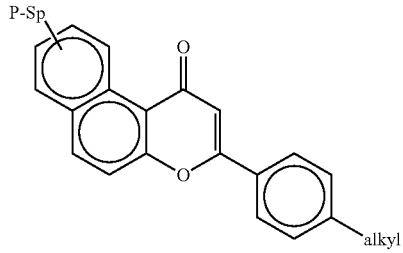

If1

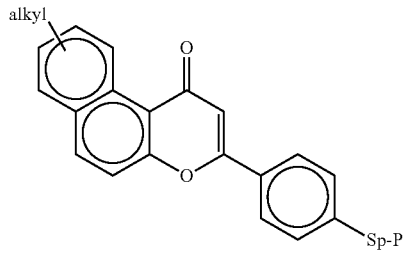

If2 wherein P is a polymerisable group and Sp is a spacer group, for use in organic light-emitting diodes. WO 2009/074520 A1 discloses coumarines of the following formula

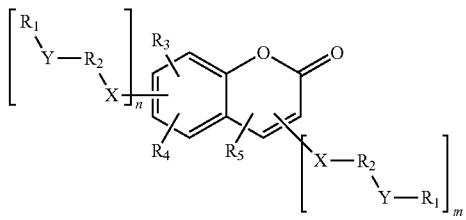

wherein $R^1$ is acrylate or methacrylate, $R^2$ is an organic straight-chain or branched alkyl or aryl substituent with up to 30 atoms selected from C, H, Si, O, N, P, S, F, Cl, Br, $R^3$-$R^5$ are H or an organic straight-chain or branched alkyl or aryl substituent with up to 30 atoms selected from C, H, Si, O, N, P, S, F, Cl, Br, X and Y are O, S, NH or NR, with R being an organic straight-chain or branched alkyl or aryl substituent with up to 30 atoms selected from C, H, Si, O, N, P, S, F, Cl, Br, n is 0, 1 or 2 and m is 0 or 1, for use as UV absorber in a copolymer for ophthalmological compositions.

However, these documents do neither disclose nor suggest the use of polymerisable coumarines in LC media of PS- or PSA-LCDs for creating a pretilt angle by in-situ polymerisation in an electric field.

WO 2010/049044 A1 discloses reactive mesogens based on coumarine or flavone for use in PSA displays, but does not explicitly disclose reactive mesogens as claimed in this invention which comprise three or more polymerizable groups or comprise two or more polymerizable groups attached to the same ring.

The compounds of the present invention are suitable for creating a high pretilt in PSA type displays. Compared to polymerizable compounds of prior art, they show a more rapid and complete polymerization reaction, and have higher solubility and enable higher VHR values in LC media.

SUMMARY OF THE INVENTION

The invention relates to the use of compounds of the formula I

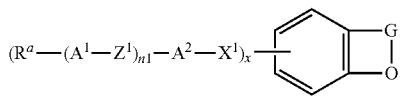

in which the individual radicals have the following meanings:

G denotes —CM=CR$^c$—CO—, —CO—CR$^c$=CM-, —CR$^c$=CM-CO— or —CO—CM=CR$^c$—,

M denotes —X$^2$-A$^4$-(Z$^2$-A$^3$)$_{n2}$-R$^b$,

A$^{1-4}$ each, independently of one another, and on each occurrence identically or differently, denote an aromatic, heteroaromatic, alicyclic or heterocyclic group, preferably having 4 to 25 C atoms, which may also contain fused rings, and which is optionally mono- or polysubstituted by L, and A$^2$ and A$^4$ may also denote a single bond, X$^1$ and X$^2$ each, independently of one another, and on each occurrence identically or differently, denote —O—, —S—, —CO—, —CO—O—, —O—CO—, —O—CO—O— or a single bond, Z$^1$ and Z$^2$ each, independently of one another, and on each occurrence identically or differently, denote —O—, —S—, —CO—, —CO—O—, —O—CO—, —O—CO—O—, —OCH$_2$—, —CH$_2$O—, —SCH$_2$—, —CH$_2$S—, —CF$_2$O—, —OCF$_2$—, —CF$_2$S—, —SCF$_2$—, —(CH$_2$)$_{n3}$—, —CF$_2$CH$_2$—, —CH$_2$CF$_2$—, —(CF$_2$)$_{n3}$—, —CH=CH—, —CF=CF—, —CH=CF—, —CF=CH—, —C≡C—, —CH=CH—CO—O—, —O—CO—CH=CH—, —CH$_2$—CH$_2$—CO—O—, —O—COCH$_2$—CH$_2$—, —CR$^0$R$^{00}$— or a single bond, R$^{a-c}$ each, independently of one another, and on each occurrence identically or differently, denote P, P-Sp-, H, OH, F, Cl, Br, I, —CN, —NO$_2$, —NCO, —NCS, —OCN, —SCN, SF$_5$ or straight-chain or branched alkyl having 1 to 25 C atoms, in which, in addition, one or more non-adjacent CH$_2$ groups may each be replaced, independently of one another, by —C(R$^{00}$)=C(R$^{000}$)—, —C≡C—, —N(R$^{00}$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I, CN or P-Sp-, wherein at least two of the radicals R$^a$ denote or contain a group P or P-Sp-, P denotes on each occurrence, identically or differently, a polymerisable group, Sp denotes on each occurrence, identically or differently, a spacer group or a single bond, R$^{00}$ and R$^{000}$ each, independently of one another, denote H or alkyl having 1 to 12 C atoms, L denotes on each occurrence, identically or differently, P-Sp-, H, OH, CH$_2$OH, halogen, SF$_5$, NO$_2$, a carbon group or hydrocarbon group, n1 and n2 each, independently of one another, denote 0, 1, 2 or 3, n3 denotes 1, 2, 3 or 4, x denotes 2, 3 or 4, in liquid-crystal (LC) media and LC displays, preferably in LC media and displays of the PS (polymer stabilised) or PSA (polymer sustained alignment) type.

The invention furthermore relates to an LC medium comprising one or more polymerisable compounds according to the invention and one or more additional compounds, which may also be mesogenic, liquid-crystalline and/or polymerisable.

The invention furthermore relates to an LC medium comprising a polymer obtainable by polymerisation of one or more polymerisable compounds according to the invention and one or more additional compounds, which may also be mesogenic, liquid-crystalline and/or polymerisable.

The invention furthermore relates to an LC medium comprising
 a polymerisable component A) comprising one or more polymerisable compounds according to the invention, and
 a liquid-crystalline component B), also referred to below as "LC host mixture", comprising one or more, preferably two or more, low-molecular-weight (monomeric and unpolymerisable) compounds as described above and below.

The invention furthermore relates to a process for the preparation of an LC medium as described above and below in which one or more low-molecular-weight liquid-crystalline compounds, or an LC host mixture as described above and below, are mixed with one or more polymerisable compounds according to the invention and optionally with further liquid-crystalline compounds and/or additives.

The invention furthermore relates to the use of polymerisable compounds according to the invention and LC media according to the invention in PS and PSA displays, in particular the use in PS and PSA displays containing an LC medium, for the production of a tilt angle in the LC medium by in-situ polymerisation of the compound(s) of the formula I in the PSA display, preferably with application of an electric or magnetic field.

The invention furthermore relates to an LC display containing one or more polymerisable compounds according to the invention or an LC medium according to the invention, in particular a PS or PSA display, particularly preferably a PSA-VA, PSA-OCB, PSA-IPS, PS-FFS, PSA-posi-VA or PSA-TN display.

The invention furthermore relates to an LC display of the PS or PSA type containing an LC cell having two substrates and two electrodes, where at least one substrate is transparent to light and at least one substrate has one or two electrodes, and a layer, located between the substrates, of an LC medium comprising a polymerised component and a low-molecular-weight component, where the polymerised component is obtainable by polymerisation of one or more polymerisable compounds between the substrates of the LC cell in the LC medium, preferably with application of an electrical voltage to the electrodes, where at least one of the polymerisable compounds is selected from polymerisable compounds according to the invention.

The invention furthermore relates to a process for the production of an LC display as described above and below in which an LC medium comprising one or more low-molecular-weight liquid-crystalline compounds or an LC host mixture as described above and below and one or more polymerisable compounds according to the invention is introduced into an LC cell having two substrates and two electrodes as described above and below, and the polymerisable compounds are polymerised, preferably with application of an electrical voltage to the electrodes.

The PS and PSA displays according to the invention have two electrodes, preferably in the form of transparent layers, which are applied to one or both of the substrates which form the LC cell. Either in each case one electrode is applied to each of the two substrates, as, for example, in PSA-VA, PSA-OCB or PSA-TN displays according to the invention, or both electrodes are applied to only one of the two substrates, while the other substrate has no electrode, as, for example, in PSA-posi-VA, PSA-IPS or PSA-FFS displays according to the invention.

The invention furthermore relates to novel compounds of the formula I in which G, $A^1$, $A^2$, $Z^1$, $X^1$, $R^a$, n1 and x have the meanings given above, and
a) $X^1$ and/or $X^2$ is a single bond, and/or
b) one of n1 and n2 is different from 0 and/or
c) one of $A^2$ and $A^4$ is not a single bond.

The invention furthermore relates to processes for the preparation of compounds of formula I, and to novel intermediates used or obtained in these processes.

Definitions of Terms

The terms "tilt" and "tilt angle" relate to a tilted alignment of the LC molecules of an LC medium relative to the surfaces of the cell in an LC display (here preferably a PS or PSA display). The tilt angle here denotes the average angle (<90°) between the longitudinal molecular axes of the LC molecules (LC director) and the surface of the plane-parallel outer plates which form the LC cell. A low value for the tilt angle (i.e. a large deviation from the 90° angle) corresponds to a large tilt here. A suitable method for measurement of the tilt angle is given in the examples. Unless indicated otherwise, tilt angle values disclosed above and below relate to this measurement method.

The term "mesogenic group" is known to the person skilled in the art and is described in the literature, and denotes a group which, due to the anisotropy of its attracting and repelling interactions, essentially contributes to causing a liquid-crystal (LC) phase in low-molecular-weight or polymeric substances. Compounds containing mesogenic groups (mesogenic compounds) do not necessarily have to have an LC phase themselves. It is also possible for mesogenic compounds to exhibit LC phase behaviour only after mixing with other compounds and/or after polymerisation. Typical mesogenic groups are, for example, rigid rod- or disc-shaped units. An overview of the terms and definitions used in connection with mesogenic or LC compounds is given in Pure Appl. Chem. 73(5), 888 (2001) and C. Tschierske, G. Pelzl, S. Diele, Angew. Chem. 2004, 116, 6340-6368.

The term "spacer group", also referred to as "Sp" above and below, is known to the person skilled in the art and is described in the literature, see, for example, Pure Appl. Chem. 73(5), 888 (2001) and C. Tschierske, G. Pelzl, S. Diele, Angew. Chem. 2004, 116, 6340-6368. Unless indicated otherwise, the term "spacer group" or "spacer" above and below denotes a flexible group which connects the mesogenic group and the polymerisable group(s) to one another in a polymerisable mesogenic compound.

The term "reactive mesogen" or "RM" denotes a compound containing one mesogenic group and one or more functional groups which are suitable for polymerisation (also referred to as polymerisable group or group P).

The terms "low-molecular-weight compound" and "unpolymerisable compound" denote compounds, usually monomeric, which contain no functional group which is suitable for polymerisation under the usual conditions known to the person skilled in the art, in particular under the conditions used for the polymerisation of RMs.

DETAILED DESCRIPTION OF THE INVENTION

Above and below "organic group" denotes a carbon or hydrocarbon group.

"Carbon group" denotes a mono- or polyvalent organic group containing at least one carbon atom, where this either contains no further atoms (such as, for example, —C≡C—) or optionally contains one or more further atoms, such as, for example, N, O, S, P, Si, Se, As, Te or Ge (for example carbonyl, etc.). The term "hydrocarbon group" denotes a carbon group which additionally contains one or more H atoms and optionally one or more heteroatoms, such as, for example, N, O, S, P, Si, Se, As, Te or Ge.

"Halogen" denotes F, Cl, Br or I.

"Conjugated radical" or "conjugated group" denotes a radical or group which contains principally $sp^2$-hybridised (or possibly also sp-hybridised) carbon atoms, which may also be replaced by corresponding heteroatoms. In the simplest case, this means the alternating presence of double and single bonds. "Principally" in this connection means that naturally (non-randomly) occurring defects which result in conjugation interruptions do not devalue the term "conjugated". Furthermore, the term "conjugated" is likewise used in this application text if, for example, arylamine units or certain heterocycles (i.e. conjugation via N, O, P or S atoms) are located in the radical or group.

A carbon or hydrocarbon group can be a saturated or unsaturated group. Unsaturated groups are, for example, aryl, alkenyl or alkynyl groups. A carbon or hydrocarbon radical having more than 3 C atoms can be straight-chain, branched and/or cyclic and may also contain spiro links or condensed rings.

The terms "alkyl", "aryl", "heteroaryl", etc., also encompass polyvalent groups, for example alkylene, arylene, heteroarylene, etc.

The term "aryl" denotes an aromatic carbon group or a group derived therefrom. The term "heteroaryl" denotes "aryl" as defined above, containing one or more heteroatoms.

Preferred carbon and hydrocarbon groups are optionally substituted alkyl, alkenyl, alkynyl, alkoxy, alkylcarbonyl, alkoxycarbonyl, alkylcarbonyloxy and alkoxycarbonyloxy having 1 to 40, preferably 1 to 25, particularly preferably 1 to 18, C atoms, optionally substituted aryl or aryloxy having 6 to 40, preferably 6 to 25, C atoms, or optionally substituted alkylaryl, arylalkyl, alkylaryloxy, arylalkyloxy, arylcarbonyl, aryloxycarbonyl, arylcarbonyloxy and aryloxycarbonyloxy having 6 to 40, preferably 6 to 25, C atoms.

Further preferred carbon and hydrocarbon groups are $C_1$-$C_{40}$ alkyl, $C_2$-$C_{40}$ alkenyl, $C_2$-$C_{40}$ alkynyl, $C_3$-$C_{40}$ allyl, $C_4$-$C_{40}$ alkyldienyl, $C_4$-$C_{40}$ polyenyl, $C_6$-$C_{40}$ aryl, $C_6$-$C_{40}$ alkylaryl, $C_6$-$C_{40}$ arylalkyl, $C_6$-$C_{40}$ alkylaryloxy, $C_6$-$C_{40}$ arylalkyloxy, $C_2$-$C_{40}$ heteroaryl, $C_4$-$C_{40}$ cycloalkyl, $C_4$-$C_{40}$ cycloalkenyl, etc. Particular preference is given to $C_1$-$C_{22}$ alkyl, $C_2$-$C_{22}$ alkenyl, $C_2$-$C_{22}$ alkynyl, $C_3$-$C_{22}$ allyl, $C_4$-$C_{22}$ alkyldienyl, $C_6$-$C_{12}$ aryl, $C_6$-$C_{20}$ arylalkyl and $C_2$-$C_{20}$ heteroaryl.

Further preferred carbon and hydrocarbon groups are straight-chain, branched or cyclic alkyl radicals having 1 to 40, preferably 1 to 25, C atoms, which are unsubstituted or mono- or polysubstituted by F, Cl, Br, I or CN and in which one or more non-adjacent $CH_2$ groups may each be replaced, independently of one another, by —C($R^x$)=C($R^x$)—, —C≡C—, —N($R^x$)—, —O—, —S—, —CO—, —CO—O—, —O—CO—, —O—CO—O— in such a way that 0 and/or S atoms are not linked directly to one another.

$R^x$ preferably denotes H, halogen, a straight-chain, branched or cyclic alkyl chain having 1 to 25 C atoms, in which, in addition, one or more non-adjacent C atoms may be replaced by —O—, —S—, —CO—, —CO—O—, —O—CO—, —O—CO—O— and in which one or more H atoms may be replaced by fluorine, an optionally substituted aryl or aryloxy group having 6 to 40 C atoms, or an optionally substituted heteroaryl or heteroaryloxy group having 2 to 40 C atoms.

Preferred alkoxy groups are, for example, methoxy, ethoxy, 2-methoxyethoxy, n-propoxy, i-propoxy, n-butoxy, i-butoxy, s-butoxy, t-butoxy, 2-methylbutoxy, n-pentoxy, n-hexoxy, n-heptoxy, n-octoxy, n-nonoxy, n-decoxy, n-undecoxy, n-dodecoxy, etc.

Preferred alkyl groups are, for example, methyl, ethyl, n-propyl, isopropyl, n-butyl, isobutyl, s-butyl, t-butyl, 2-methylbutyl, n-pentyl, s-pentyl, cyclo-pentyl, n-hexyl, cyclohexyl, 2-ethylhexyl, n-heptyl, cycloheptyl, n-octyl, cyclooctyl, n-nonyl, n-decyl, n-undecyl, n-dodecyl, dodecanyl, trifluoromethyl, perfluoro-n-butyl, 2,2,2-trifluoroethyl, perfluorooctyl, perfluorohexyl, etc.

Preferred alkenyl groups are, for example, ethenyl, propenyl, butenyl, pentenyl, cyclopentenyl, hexenyl, cyclohexenyl, heptenyl, cycloheptenyl, octenyl, cyclooctenyl, etc.

Preferred alkynyl groups are, for example, ethynyl, propynyl, butynyl, pentynyl, hexynyl, octynyl, etc.

Preferred alkoxy groups are, for example, methoxy, ethoxy, 2-methoxyethoxy, n-propoxy, i-propoxy, n-butoxy, i-butoxy, s-butoxy, t-butoxy, 2-methylbutoxy, n-pentoxy, n-hexoxy, n-heptoxy, n-octoxy, n-nonoxy, n-decoxy, n-undecoxy, n-dodecoxy, etc.

Preferred amino groups are, for example, dimethylamino, methylamino, methylphenylamino, phenylamino, etc.

Aryl and heteroaryl groups can be monocyclic or polycyclic, i.e. they can contain one ring (such as, for example, phenyl) or two or more rings, which may also be fused (such as, for example, naphthyl) or covalently bonded (such as, for example, biphenyl), or contain a combination of fused and linked rings. Heteroaryl groups contain one or more heteroatoms, preferably selected from O, N, S and Se.

Particular preference is given to mono-, bi- or tricyclic aryl groups having 6 to 25 C atoms and mono-, bi- or tricyclic heteroaryl groups having 5 to 25 ring atoms, which optionally contain fused rings and are optionally substituted. Preference is furthermore given to 5-, 6- or 7-membered aryl and heteroaryl groups, in which, in addition, one or more CH groups may be replaced by N, S or O in such a way that O atoms and/or S atoms are not linked directly to one another.

Preferred aryl groups are, for example, phenyl, biphenyl, terphenyl, [1,1':3',1"]terphenyl-2'-yl, naphthyl, anthracene, binaphthyl, phenanthrene, pyrene, dihydropyrene, chrysene, perylene, tetracene, pentacene, benzopyrene, fluorene, indene, indenofluorene, spirobifluorene, etc.

Preferred heteroaryl groups are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]-thiophene, thieno[3,2b]thiophene, dithienothiophene, isobenzothiophene, dibenzothiophene, benzothiadiazothiophene, or combinations of these groups.

The aryl and heteroaryl groups mentioned above and below may also be substituted by alkyl, alkoxy, thioalkyl, fluorine, fluoroalkyl or further aryl or heteroaryl groups.

The (non-aromatic) alicyclic and heterocyclic groups encompass both saturated rings, i.e. those containing exclusively single bonds, and also partially unsaturated rings, i.e. those which may also contain multiple bonds. Heterocyclic rings contain one or more heteroatoms, preferably selected from Si, O, N, S and Se.

The (non-aromatic) alicyclic and heterocyclic groups can be monocyclic, i.e. contain only one ring (such as, for example, cyclohexane), or polycyclic, i.e. contain a plurality of rings (such as, for example, decahydronaphthalene or bicyclooctane). Particular preference is given to saturated groups. Preference is furthermore given to mono-, bi- or tricyclic groups having 5 to 25 ring atoms, which optionally contain fused rings and are optionally substituted. Preference is furthermore given to 5-, 6-, 7- or 8-membered carbocyclic groups, in which, in addition, one or more C atoms may be replaced by Si and/or one or more CH groups may be replaced by N and/or one or more non-adjacent $CH_2$ groups may be replaced by —O— and/or —S—.

Preferred alicyclic and heterocyclic groups are, for example, 5-membered groups, such as cyclopentane, tetrahydrofuran, tetrahydrothiofuran, pyrrolidine, 6-membered groups, such as cyclohexane, silinane, cyclohexene, tetrahydropyran, tetrahydrothiopyran, 1,3-dioxane, 1,3-dithiane, piperidine, 7-membered groups, such as cycloheptane, and fused groups, such as tetrahydronaphthalene, decahydronaphthalene, indane, bicyclo[1.1.1]-pentane-1,3-diyl, bicyclo[2.2.2]octane-1,4-diyl, spiro[3.3]heptane-2,6-diyl, octahydro-4,7-methanoindane-2,5-diyl.

Preferred substituents are, for example, solubility-promoting groups, such as alkyl or alkoxy, electron-withdrawing groups, such as fluorine, nitro or nitrile, or substituents for increasing the glass transition temperature (Tg) in the polymer, in particular bulky groups, such as, for example, t-butyl or optionally substituted aryl groups.

Preferred substituents, also referred to as "L" above and below, are, for example, F, Cl, Br, I, —CN, —$NO_2$, —NCO, —NCS, —OCN, —SCN, —C(=O)N($R^x$)$_2$, —C(=O)$Y^1$, —C(=O)$R^x$, —N($R^x$)$_2$, in which $R^x$ has the meaning indicated above, and $Y^1$ denotes halogen, optionally substituted silyl or aryl having 6 to 40, preferably 6 to 20, C atoms, and straight-chain or branched alkyl, alkoxy, alkylcarbonyl, alkoxycarbonyl, alkylcarbonyloxy or alkoxycarbonyloxy having 1 to 25 C atoms, in which one or more H atoms may optionally be replaced by F or Cl.

"Substituted silyl or aryl" preferably means substituted by halogen, —CN, $R^0$, —$OR^0$, —CO—$R^0$, —CO—O—$R^0$, —O—CO—$R^0$ or —O—CO—O—$R^0$, in which $R^0$ has the meaning indicated above.

Particularly preferred substituents L are, for example, F, Cl, CN, $NO_2$, $CH_3$, $C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$, furthermore phenyl.

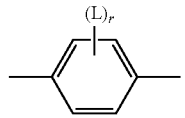

is preferably

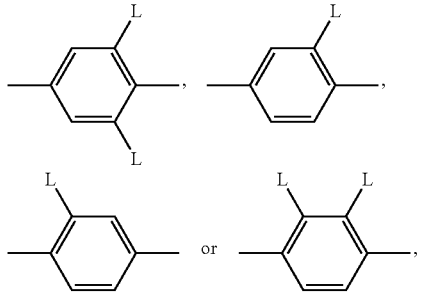

in which L has one of the meanings indicated above.

The polymerisable group P is a group which is suitable for a polymerisation reaction, such as, for example, free-radical or ionic chain polymerisation, polyaddition or polycondensation, or for a polymer-analogous reaction, for example addition or condensation onto a main polymer chain. Particular preference is given to groups for chain polymerisation, in particular those containing a C=C double bond or —C≡C— triple bond, and groups which are suitable for polymerisation with ring opening, such as, for example, oxetane or epoxide groups.

Preferred groups P are selected from the group consisting of $CH_2=CW^1—CO—O—$, $CH_2=CW^1—CO—$,

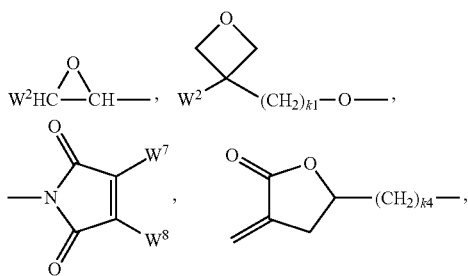

$CH_2=CW^2—(O)_{k3}—$, $CW^1=CH—CO—(O)_{k3}—$, $CW^1=CH—CO—NH—$, $CH_2=CW^1—CO—NH—$, $CH_3—CH=CH—O—$, $(CH_2=CH)_2CH—OCO—$, $(CH_2=CH—CH_2)_2CH—OCO—$, $(CH_2=CH)_2CH—O—$, $(CH_2=CH—CH_2)_2N—$, $(CH_2=CH—CH_2)_2N—CO—$, $HO—CW^2W^3—$, $HS—CW^2W^3—$, $HW^2N—$, $HO—CW^2W^3—NH—$, $CH_2=CW^1—CO—NH—$, $CH_2=CH—(COO)_{k1}$-Phe-$(O)_{k2}—$, $CH_2=CH—(CO)_{k1}$-Phe-$(O)_{k2}—$, Phe-CH=CH—, HOOC—, OCN— and $W^4W^5W^6Si—$, in which $W^1$ denotes H, F, Cl, CN, $CF_3$, phenyl or alkyl having 1 to 5 C atoms, in particular H, F, Cl or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonylalkyl having 1 to 5 C atoms, $W^7$ and $W^8$ each, independently of one another, denote H, Cl or alkyl having 1 to 5 C atoms, Phe denotes 1,4-phenylene, which is optionally substituted by one or more radicals L as defined above which are other than P-Sp-, $k_1$, $k_2$ and $k_3$ each, independently of one another, denote 0 or 1, $k_3$ preferably denotes 1, and $k_4$ denotes an integer from 1 to 10.

Particularly preferred groups P are selected from the group consisting of $CH_2=CW^1—CO—O—$, $CH_2=CW^1—CO—$,

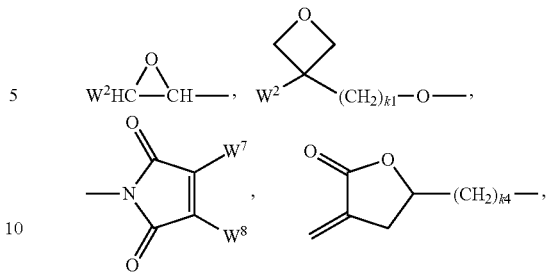

$CH_2=CW^2—O—$, $CH_2=CW^2—$, $CW^1=CH—CO—(O)_{k3}—$, $CW^1=CH—CO—NH—$, $CH_2=CW^1—CO—NH—$, $(CH_2=CH)_2CH—OCO—$, $(CH_2=CH—CH_2)_2CH—OCO—$, $(CH_2=CH)_2CH—O—$, $(CH_2=CH—CH_2)_2N—$, $(CH_2=CH—CH_2)_2N—CO—$, $CH_2=CW^1—CO—NH—$, $CH_2=CH—(COO)_{k1}$-Phe-$(O)_{k2}—$, $CH_2=CH—(CO)_{k1}$-Phe-$(O)_{k2}—$, Phe-CH=CH— and $W^4W^5W^6Si—$, in which $W^1$ denotes H, F, Cl, CN, $CF_3$, phenyl or alkyl having 1 to 5 C atoms, in particular H, F, Cl or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonylalkyl having 1 to 5 C atoms, $W^7$ and $W^8$ each, independently of one another, denote H, Cl or alkyl having 1 to 5 C atoms, Phe denotes 1,4-phenylene, $k_1$, $k_2$ and $k_3$ each, independently of one another, denote 0 or 1, $k_3$ preferably denotes 1, and $k_4$ denotes an integer from 1 to 10.

Very particularly preferred groups P are selected from the group consisting of $CH_2=CW^1—CO—O—$, in particular $CH_2=CH—CO—O—$, $CH_2=C(CH_3)—CO—O—$ and $CH_2=CF—CO—O—$, furthermore $CH_2=CH—O—$, $(CH_2=CH)_2CH—O—CO—$, $(CH_2=CH)_2CH—O—$,

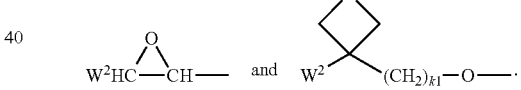

Further very particularly preferred groups P are selected from the group consisting of vinyl, vinyloxy, acrylate, methacrylate, fluoroacrylate, chloroacrylate, oxetane and epoxide groups, and particularly preferably denote an acrylate or methacrylate group.

Preferred spacer groups Sp other than a single bond are selected from the formula Sp"-X", so that the radical P-Sp- conforms to the formula P-Sp"-X"—, where Sp" denotes alkylene having 1 to 20, preferably 1 to 12, C atoms, which is optionally mono- or polysubstituted by F, Cl, Br, I or CN and in which, in addition, one or more non-adjacent $CH_2$ groups may each be replaced, independently of one another, by —O—, —S—, —NH—, —N($R^0$)—, —Si($R^{00}R^{000}$)—, —CO—, —CO—O—, —O—CO—, —O—CO—O—, —S—CO—, —CO—S—, —N($R^{00}$)—CO—O—, —O—CO—N($R^{00}$)—, —N($R^{00}$)—CO—N($R^{00}$)—, —CH=CH— or —C≡C— in such a way that O and/or S atoms are not linked directly to one another, X" denotes —O—, —S—, —CO—, —CO—O—, —O—CO—, —O—CO—O—, —CO—N($R^{00}$)—, —N($R^{00}$)—CO—, —N($R^{00}$)—CO—N($R^{00}$)—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^0$—, —CY$^2$=CY$^3$—, —C≡C—, —CH=CH—CO—O—, —O—CO—CH=CH— or a single bond, R$^{00}$ and R$^{000}$ each, independently of one another, denote H or alkyl having 1 to 12 C atoms, and Y$^2$ and Y$^3$ each, independently of one another, denote H, F, Cl or CN.

X' is preferably —O—, —S—, —CO—, —COO—, —OCO—, —O—COO—, —CO—NR$^0$—, —NR$^0$—CO—, —NR$^0$—CO—NR$^0$— or a single bond.

Typical spacer groups Sp" are, for example, —(CH$_2$)$_{p1}$—, —(CH$_2$CH$_2$O)$_{q1}$—CH$_2$CH$_2$—, —CH$_2$CH$_2$—S—CH$_2$CH$_2$—, —CH$_2$CH$_2$—NH—CH$_2$CH$_2$— or —(SiR$^{00}$R$^{000}$—O)$_{p1}$—, in which p1 is an integer from 1 to 12, q1 is an integer from 1 to 3, and R$^{00}$ and R$^{000}$ have the meanings indicated above.

Particularly preferred groups -Sp"-X"— are —(CH$_2$)$_{p1}$—, —(CH$_2$)$_{p1}$—O—, —(CH$_2$)$_{p1}$—O—CO—, —(CH$_2$)$_{p1}$—O—CO—O—, in which p1 and q1 have the meanings indicated above.

Particularly preferred groups Sp" are, for example, in each case straight-chain ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyliminoethylene, 1-methylalkylene, ethenylene, propenylene and butenylene.

In a further preferred embodiment of the invention, R$^a$ and/or R$^b$ in formula I denote a radical containing two or more polymerisable groups (multifunctional polymerisable radicals). Suitable radicals of this type and polymerisable compounds containing them and the preparation thereof are described, for example, in U.S. Pat. No. 7,060,200 B1 or US 2006/0172090 A1. Particular preference is given to multifunctional polymerisable radicals selected from the following formulae:

| | |
|---|---|
| —X-alkyl-CHP$^1$—CH$_2$—CH$_2$P$^2$ | I*a |
| —X-alkyl-C(CH$_2$P$^1$)(CH$_2$P$^2$)—CH$_2$P$^3$ | I*b |
| —X-alkyl-CHP$^1$CHP$^2$—CH$_2$P$^3$ | I*c |
| —X-alkyl-C(CH$_2$P$^1$)(CH$_2$P$^2$)—C$_{aa}$H$_{2aa+1}$ | I*d |
| —X-alkyl-CHP$^1$—CH$_2$P$^2$ | I*e |
| —X-alkyl-CHP$^1$P$^2$ | I*f |
| —X-alkyl-CP$^1$P$^2$-C$_{aa}$H$_{2aa+1}$ | I*g |
| —X-alkyl-C(CH$_2$P$^1$)(CH$_2$P$^2$)—CH$_2$OCH$_2$—C(CH$_2$P$^3$)(CH$_2$P$^4$)CH$_2$P$^5$ | I*h |
| —X-alkyl-CH((CH$_2$)$_{aa}$P$^1$)((CH$_2$)$_{bb}$P$^2$) | I*i |
| —X-alkyl-CHP$^1$CHP$^2$—C$_{aa}$H$_{2aa+1}$ | I*k |
| —X'-alkyl-C(CH$_3$)(CH$_2$P$^1$)(CH$_2$P$^2$) | I*m | in which alkyl denotes a single bond or straight-chain or branched alkylene having 1 to 12 C atoms, in which one or more non-adjacent CH$_2$ groups may each be replaced, independently of one another, by —C(R$^{00}$)=C(R$^{000}$)—, —C≡C—, —N(R$^{00}$)—, —O—, —S—, —CO—, —CO—O—, —O—CO—, —O—CO—O— in such a way that O and/or S atoms are not linked directly to one another and in which, in addition, one or more H atoms may be replaced by F, Cl or CN, where R$^{00}$ and R$^{000}$ have the meanings indicated above, aa and bb each, independently of one another, denote 0, 1, 2, 3, 4, 5 or 6, X has one of the meanings indicated for X', and P$^{1-5}$ each, independently of one another, have one of the meanings indicated for P.

Formula I covers the following compounds

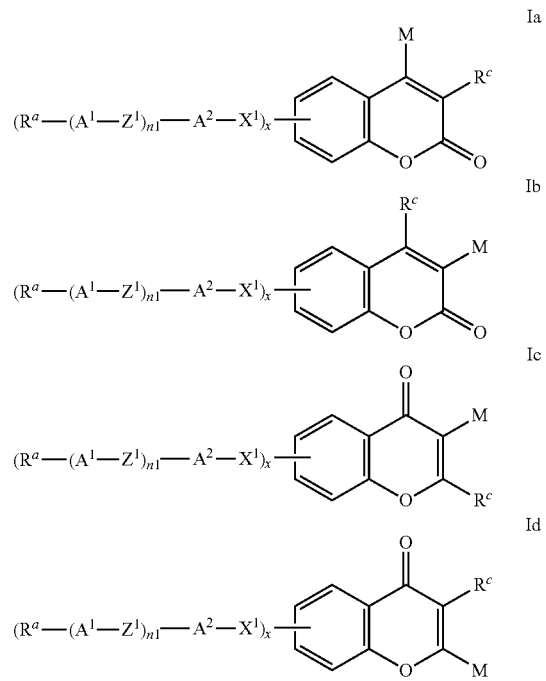

wherein R$^a$, R$^c$, A$^1$, A$^2$, Z$^1$, X$^1$, M, n1 and x are as defined in formula I. Compounds of formula Ib and Ic are especially preferred.

Particularly preferred compounds of the formula I and sub-formulae thereof indicated above and below are those which contain more than two, preferably three, four, five or six groups R$^a$ or R$^b$ which denote P or P-Sp-.

Particularly preferred compounds of the formula I and sub-formulae thereof indicated above and below are those in which A$^1$, A$^2$, A$^3$, A$^4$ each, independently of one another, when being different from a single bond, denote 1,4-phenylene, naphthalene-1,4-diyl or naphthalene-2,6-diyl, where one or more CH groups in these groups are optionally replaced by N, cyclohexane-1,4-diyl, in which, in addition, one or more non-adjacent CH$_2$ groups are optionally replaced by 0 and/or S, 1,4-cyclohexenylene, bicyclo [1.1.1]pentane-1,3-diyl, bicyclo[2.2.2]octane-1,4-diyl, spiro[3.3]heptane-2,6-diyl, piperidine-1,4-diyl, decahydronaphthalene-2,6-diyl, 1,2,3,4-tetrahydronaphthalene-2,6-diyl, indane-2,5-diyl or octahydro-4,7-methanoindane-2,5-diyl, where all these groups are unsubstituted or mono- or polysubstituted by L, L denotes P, P-Sp-, OH, CH$_2$OH, F, Cl, Br, I, —CN, —NO$_2$, —NCO, —NCS, —OCN, —SCN, —C(=O)N(R$^x$)$_2$, —C(=O)Y$^1$, —C(=O)R$^x$, —N(R$^x$)$_2$, optionally substituted silyl, optionally substituted aryl having 6 to 20 C atoms, straight-chain or branched alkyl or alkoxy having 1 to 25 C atoms, or straight-chain or branched alkenyl, alkynyl, alkylcarbonyl, alkoxycarbonyl, alkylcarbonyloxy or alkoxycarbonyloxy having 2 to 25 C atoms, in which, in addition, one or more H atoms in all these groups may be replaced by F, Cl, P or P-Sp-, $Y^1$ denotes halogen, and $R^x$ denotes P, P-Sp-, H, halogen, straight-chain, branched or cyclic alkyl having 1 to 25 C atoms, in which, in addition, one or more non-adjacent $CH_2$ groups may be replaced by —O—, —S—, —CO—, —CO—O—, —O—CO—, —O—CO—O— in such a way that O and/or S atoms are not linked directly to one another, and in which, in addition, one or more H atoms may be replaced by F, Cl or P-Sp-.

Further preferred compounds of the formula I and subformulae thereof indicated above and below are those in which x is 2 or 3, x is 2, $R^a$ and $R^b$ denote identical or different radicals P-Sp-, $R^a$ and $R^b$ denote identical or different radicals P-Sp- in which one or more radicals Sp denote a single bond, x is 2 or 3 and all radicals $R^a$ denote identical groups P-Sp-, $R^b$ denotes an unpolymerisable group, preferably selected from straight-chain or branched alkyl having 1 to 25 C atoms, in which, in addition, one or more non-adjacent $CH_2$ groups may each be replaced, independently of one another, by —C($R^{00}$)=C($R^{000}$)—, —C≡C—, —N($R^{00}$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I or CN, $R^b$ denotes P-Sp-, $R^b$ denotes P-Sp- wherein Sp denotes a single bond, $R^c$ denotes H, $C_{1-8}$-alkyl or $C_{1-8}$-alkoxy, preferably H, one or more of the radicals Sp denote a single bond, one or more of the radicals Sp denotes —$(CH_2)_{p1}$—, —$(CH_2)_{p1}$—O—, —$(CH_2)_{p1}$—OCO— or —$(CH_2)_{p1}$—OCOO—, in which p1 denotes an integer from 1 to 12 and r1 denotes an integer from 1 to 8, L does not denote or contain a polymerisable group, $A^1$ and $A^3$ are selected from the group consisting of 1,4-phenylene and naphthalene-2,6-diyl, where, in addition, one or two CH groups in these rings are optionally replaced by N, and where these rings are optionally mono- or polysubstituted by L, as described above and below, $A^2$ is a single bond, $A^4$ is a single bond, $A^2$ and $A^4$, when being different from a single bond, are selected from the group consisting of 1,4-phenylene and naphthalene-2,6-diyl, where, in addition, one or two CH groups in these rings are optionally replaced by N, and where these rings are optionally mono- or polysubstituted by L, as described above and below, n1=n2=0, and one of $A^2$ and $A^4$ is a single bond and the other is not a single bond, and is preferably 1,4-phenylene or naphthalene-2,6-diyl, where, in addition, one or two CH groups in these rings are optionally replaced by N, and where these rings are optionally mono- or polysubstituted by L, as described above and below $Z^1$ and $Z^2$ are selected from the group consisting of —O—, —CO—O—, —OCO—, —OCH$_2$—, —CH$_2$O—, —CF$_2$O—, —OCF$_2$—, —CH$_2$CH$_2$—, —CH=CH—, —CF=CF—, —CH=CF—, —CF=CH—, —C≡C—, single bond, n1 is 0 or 1, preferably 0 and $A^2$ is a single bond, n2 is 0 and $A^4$ is a single bond, n2 is 0 and $A^4$ is not a single bond, n2 is not 0 and is preferably 1 or 2, very preferably 1, and $A^4$ is a single bond, —$X^2$-$A^4$-($Z^2$-$A^3$)$_{n2}$- does not denote —CO—C$_6$H$_4$— (where C$_6$H$_4$ stands for 1,4-phenylene), $X^2$-$A^4$-($Z^2$-$A^3$)$_{n2}$-$R^b$ does not denote —CO—C$_6$H$_5$, L is an unpolymerisable group, preferably selected from F, Cl, —CN and straight-chain or branched alkyl having 1 to 25, particularly preferably 1 to 10, C atoms, in which, in addition, one or more non-adjacent $CH_2$ groups may each be replaced, independently of one another, by —C($R^{00}$)=C($R^{000}$)—, —C≡C—, —N($R^{00}$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I or CN.

Particularly preferred compounds of the formula I are selected from the group consisting of the following subformulae:

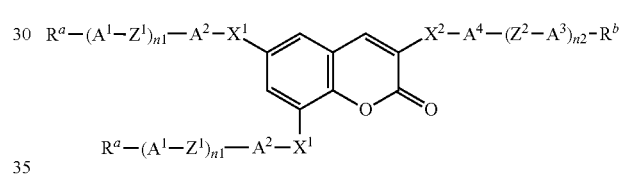

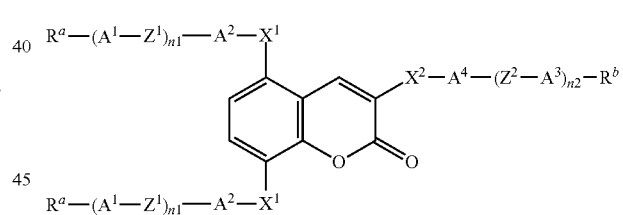

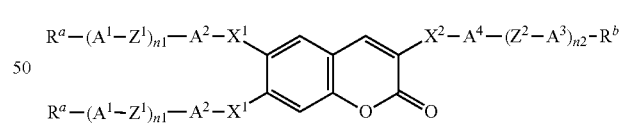

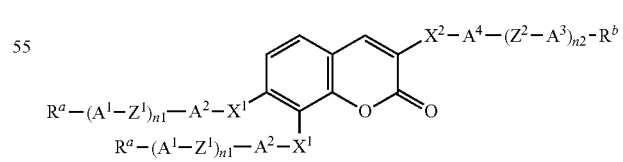

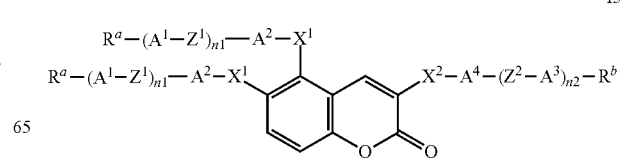

-continued

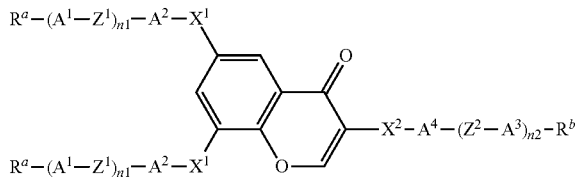

I6

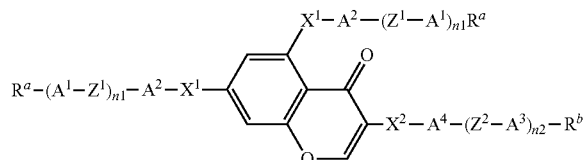

I7

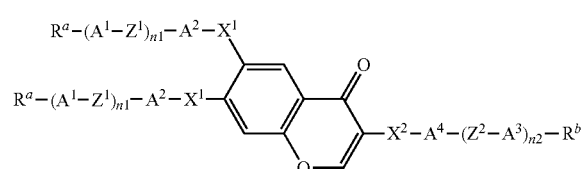

I8

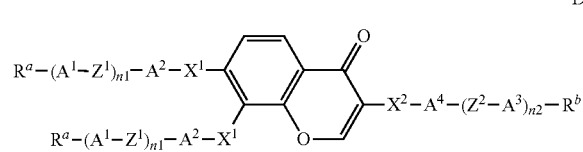

I9

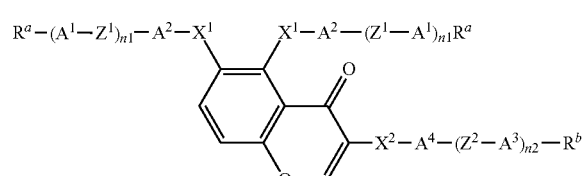

I10

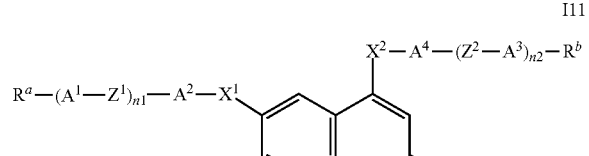

I11

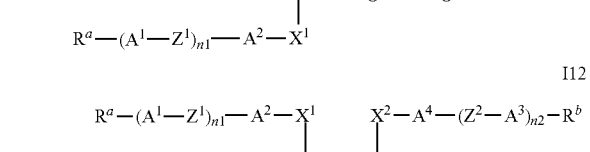

I12

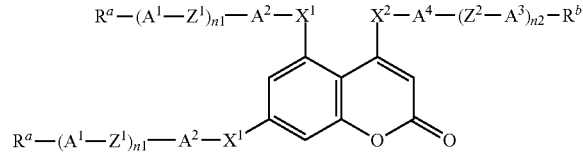

I13

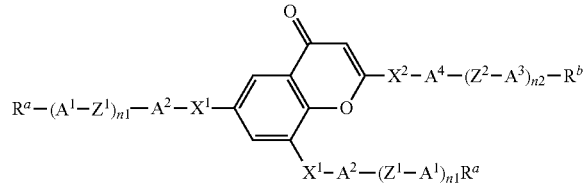

-continued

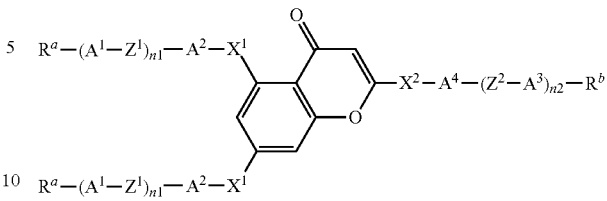

I14 in which $R^a$, $R^b$, $A^{1-4}$, $Z^{1,2}$, $X^{1,2}$, n1 and n2 each, independently of one another, have one of the meanings indicated in formula I or as indicated above and below.

Especially preferred are compounds of formulae I1-I14, in which $R^a$ is P-Sp-, and P, Sp, $R^b$, $A^{1-4}$, $Z^{1,2}$, $X^{1,2}$, n1 and n2 each, independently of one another, have one of the meanings indicated in formula I or as indicated above and below.

In case n1 or n2, respectively, is different from 0, the group -$(A^1$-$Z^1)_{n1}$-$A^2$-$X^1$— and $X^2$-$A^4$-$(Z^2$-$A^2)_{n2}$-, respectively, in the compounds of the formulae I and I1-I14 preferably denotes 1,4-phenylene or naphthalene-2,6-diyl, where, in addition, one or two CH groups in these rings are optionally replaced by N, and where, in addition, these rings are optionally mono- or polysubstituted by L, as described above and below.

Very preferred compounds of formulae I1 to I14 are those wherein n1 is 0 and $A^2$ is a single bond.

Further preferred compounds of formulae I1 to I14 are those wherein n2 is 1 and $A^4$ is a single bond.

Further preferred compounds of formulae I1 to I14 are those wherein $R^b$ denotes P-Sp-.

Further preferred compounds of formulae I1 to I14 are those wherein $R^b$ denotes an unpolymerisable group, preferably selected from straight-chain or branched alkyl having 1 to 25 C atoms, in which, in addition, one or more non-adjacent $CH_2$ groups may each be replaced, independently of one another, by —C($R^{00}$)=C($R^{000}$)—, —C≡C—, N($R^{00}$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I or CN.

Very preferred compounds of formulae I1 to I14 are those wherein $R^a$ is P-Sp- and Sp is different from a single bond.

Further preferred compounds of formulae I1 to I14 are those wherein $R^a$ is P-Sp- and one or both groups Sp denote a single bond.

Further preferred compounds of formulae I1 to I14 are those wherein $R^b$ is P-Sp- and Sp denotes a single bond.

Further preferred compounds of formulae I1 to I14 are those wherein $R^b$ is P-Sp- and Sp is different from a single bond.

Very particularly preferred compounds of the formulae I1 to I14 are selected from the group consisting of the following sub-formulae:

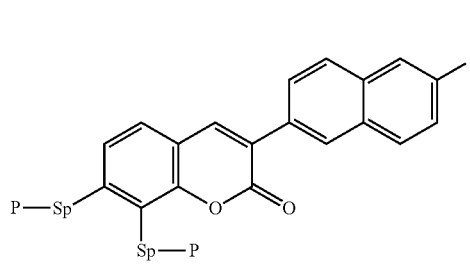
I4c
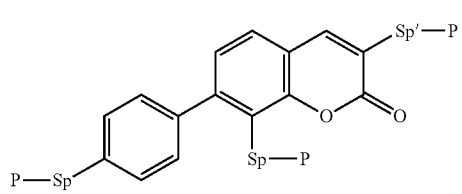
I4d
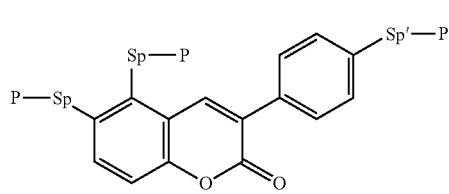
I5a
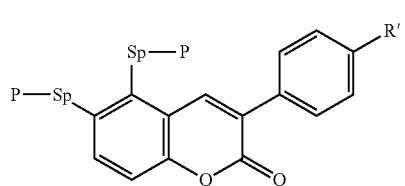
I5b
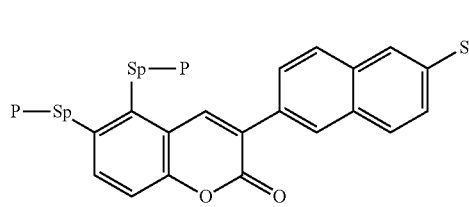
I5c
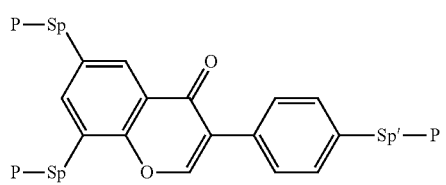
I6a
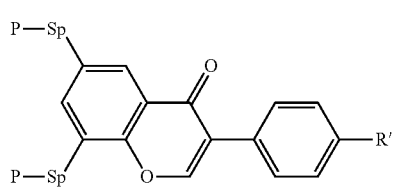
I6b
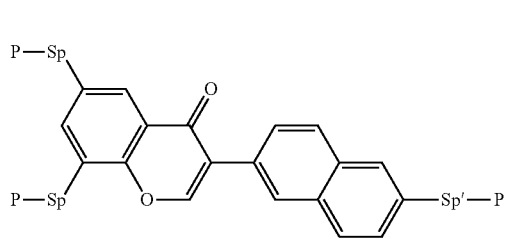
I6c
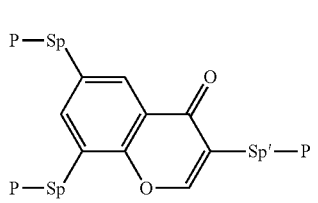
I6d
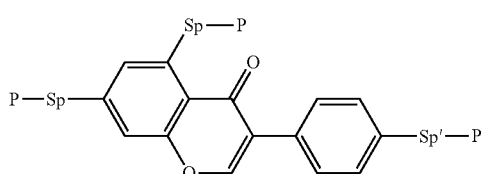
I7a
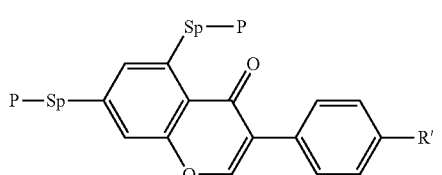
I7b
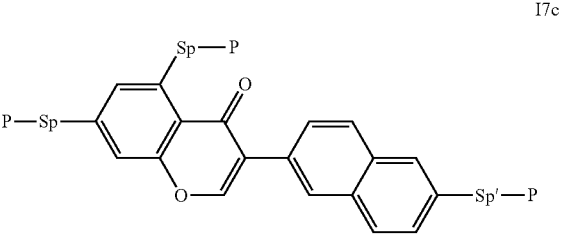
I7c
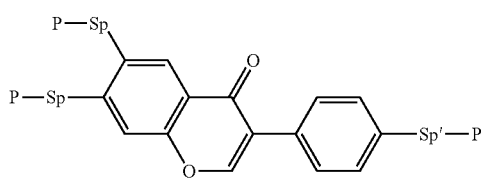
I8a
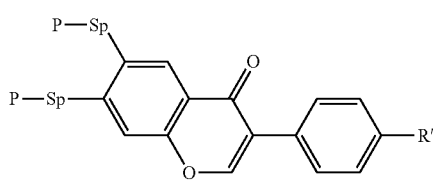
I8b
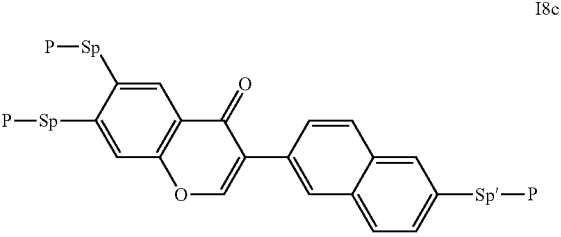
I8c
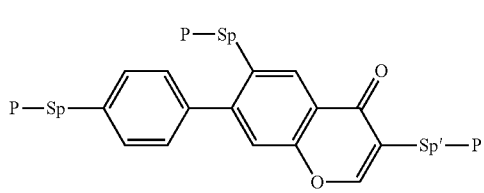
I8d -continued -continued

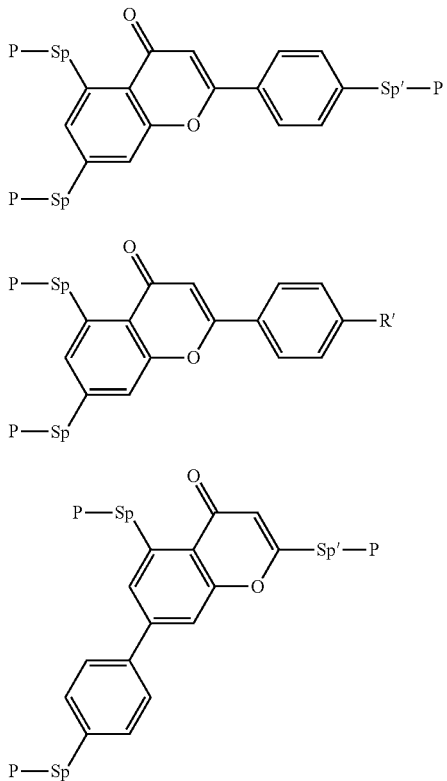

I4a

I4b

I4c in which P and Sp have one of the meanings indicated in formula I or above and below, Sp' has one of the meanings given for Sp, and is identical to or different from Sp, and R' has one of the meanings indicated for $R^b$ in formula I or above and below which is different from H, P— and P-Sp-, and wherein the phenylene and naphthalene groups are optionally substituted with one, two, three of four F atoms.

P in the compounds of the formulae I, I1 to I14 and I1a to I14c preferably denote an acrylate, fluoroacrylate or methacrylate group.

Sp in the compounds of the formulae I, I1 to I14 and I1a to I14c preferably denote —$(CH_2)_{p1}$—, —O—$(CH_2)_{p1}$—, —$(CH_2)_{p1}$—O—, —OCO—$(CH_2)_{p1}$—, —$(CH_2)_{p1}$—OCO—, —OCOO—$(CH_2)_{p1}$— or —$(CH_2)_{p1}$—OCOO—, in which p1 denotes an integer from 1 to 12, preferably from 1 to 6, and r1 denotes an integer from 1 to 8, preferably 1, 2 or 3, where these groups are linked to P in such a way that 0 atoms are not linked directly to one another.

Preference is given to compounds of the formulae I, I1 to I14 and I1a to I14c wherein P denotes an acrylate, fluoroacrylate or methacrylate group, and Sp denotes —$(CH_2)_{p1}$—, —O—$(CH_2)_{p1}$—, —$(CH_2)_{p1}$—O—, —OCO—$(CH_2)_{p1}$—, —$(CH_2)_{p1}$—OCO—, —OCOO—$(CH_2)_{p1}$— or —$(CH_2)_{p1}$—OCOO—, in which p1 denotes an integer from 1 to 12, preferably from 1 to 6, and r1 denotes an integer from 1 to 8, preferably 1, 2 or 3, where these groups are linked to P in such a way that O atoms are not linked directly to one another.

Preference is furthermore given to compounds of the sub-formulae I1a-I14c in which one or more of the radicals Sp denote a single bond and one or more of the radicals Sp are not a single bond.

Preference is furthermore given to compounds of the sub-formulae I1a-I14c in which one or more of the radicals Sp denote a single bond and one or more of the radicals Sp are not a single bond, and P denotes an acrylate, fluoroacrylate or methacrylate group.

The invention furthermore relates to novel compounds of the formula I and sub-formulae I1 to I14 in which the individual radicals have the meaning indicated in formula I or as given above and below, and wherein a) $X^1$ and/or $X^2$ is a single bond, and/or
b) one of n1 and n2 is different from 0 and/or
c) one of $A^2$ and $A^4$ is not a single bond.

Particular preference is given to novel compounds of the formula I and sub-formulae I1 to I14 as defined above, in which n2 is not 0 and preferably denotes 1 or 2.

Particular preference is furthermore given to novel compounds selected from the sub-formulae I1a to I14c as defined above.

The invention furthermore relates to novel intermediates for the preparation of compounds of the formula I, selected from the following formula:

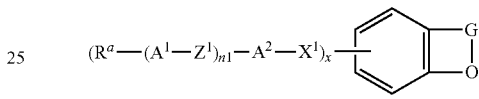

I* in which G, $A^{1,2}$, $Z^1$, $X^1$, x and n1 have the meaning indicated in formula I or above and below, and the radicals $R^a$ and $R^b$ each, independently of one another, denote -Sp-O—Sg, where Sp has the meaning indicated in formula I or above and below, and Sg denotes an H atom or a protecting group, and wherein preferably a) $X^1$ and/or $X^2$ is a single bond, and/or
b) one of n1 and n2 is different from 0 and/or
c) one of $A^2$ and $A^4$ is not a single bond.

Suitable protecting groups Sg are known to the person skilled in the art. Preferred protecting groups are alkyl, acyl and alkyl- or arylsilyl groups, 2-tetrahydropyranyl or methoxymethyl.

Particularly preferred intermediates are selected from the sub-formulae I1 to I14 as indicated above, where $R^a$ and $R^b$ are as defined in formula I*.

Very particularly preferred intermediates are selected from the group consisting of the following sub-formulae:

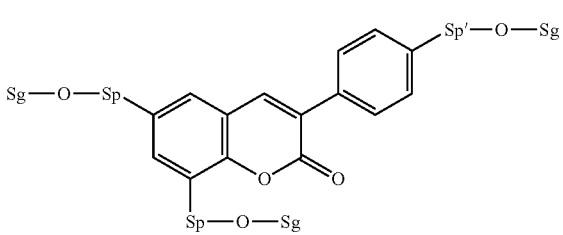

I*1a

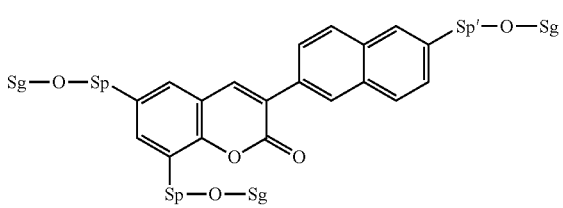

I*1b

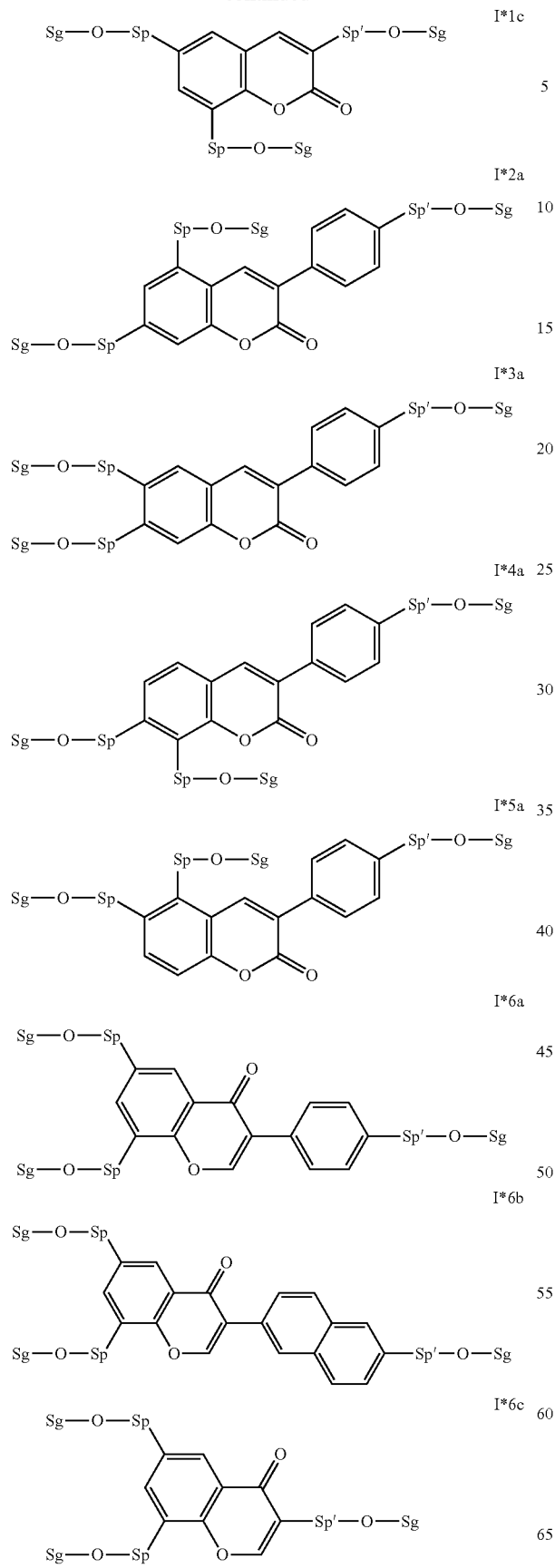
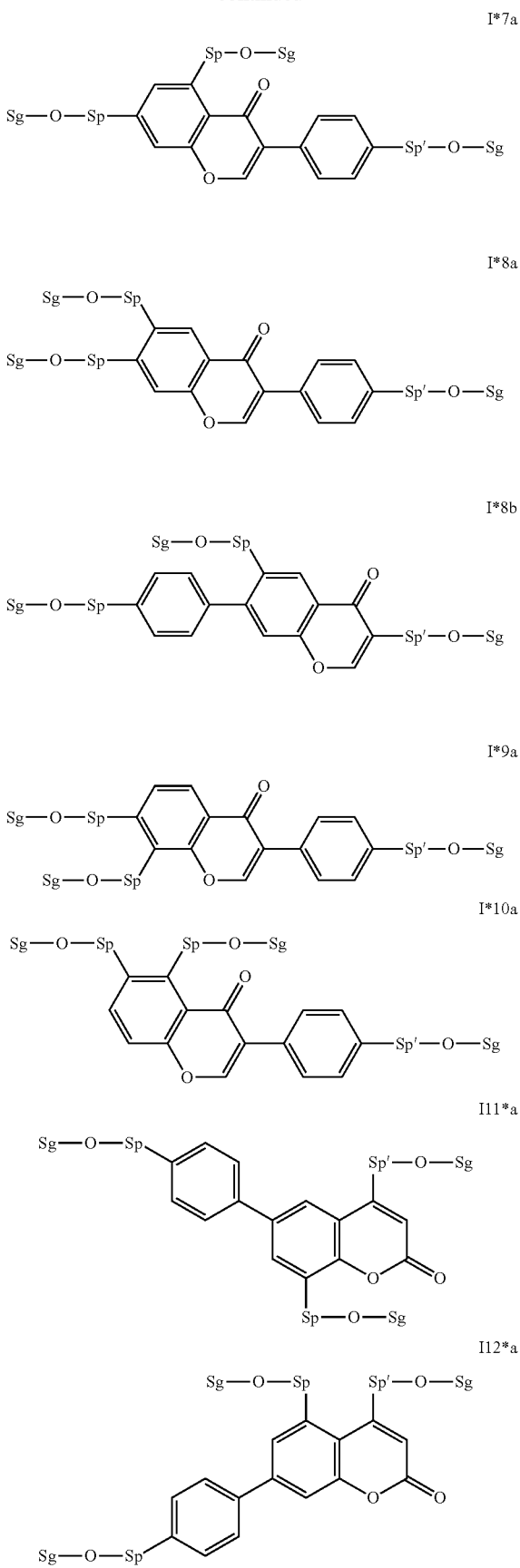

-continued

I13*a

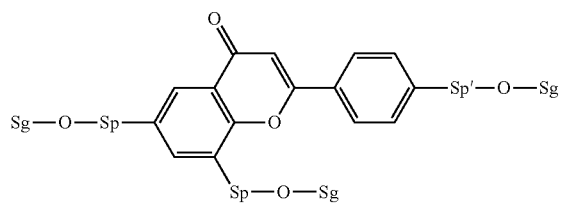

I14*a

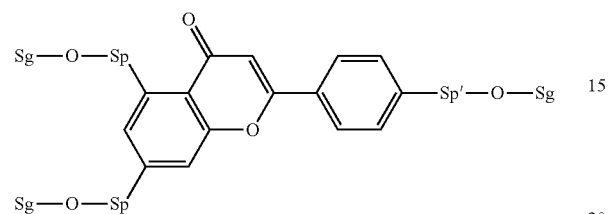

in which Sp and Sg have the meanings indicated above, and Sp' has one of the meanings given for Sp, and is identical to or different from Sp. Sg particularly preferably denotes H. Particular preference is given to compounds of the formulae shown above in which one of the radicals Sp and Sp' denotes —$(CH_2)_{p1}$— or a single bond and the other denotes a single bond, where p1 is as defined above.

The compounds and intermediates of the formulae I and I* and sub-formulae thereof can be prepared analogously to processes known to the person skilled in the art and described in standard works of organic chemistry, such as, for example, in Houben-Weyl, Methoden der organischen Chemie [Methods of Organic Chemistry], Thieme-Verlag, Stuttgart. For example, compounds of the formula I are synthesised by esterification or etherification of the intermediates of the formula I using corresponding acids, acid derivatives, or halogenated compounds containing a group P, such as, for example, (meth)acryloyl chloride or methacrylic anhydride in the presence of a base, or (meth)acrylic acid in the presence of a dehydrating reagent, such as, for example, DCC (dicyclohexylcarbodiimide).

Particularly suitable and preferred processes for the preparation of compounds and intermediates of the formulae I and I* are depicted by way of example in the following schemes and preferably comprise one or more of the steps described below.

General access to coumarines is provided, for example, by condensation of salicylic aldehydes with phenylacetic acid derivatives in the sense of a Perkin reaction [cf. e.g. M. J. Matos et al., Bioorg. Med. Chem. Lett. 20 (2010) 5157-5160 and literature cited therein], or from salicylic aldehydes and benzonitriles (N. P. Buu-Hoï, N. Hoán, M. R. Khenissi, J. Chem. Soc. 1951, 2307) in accordance with scheme 1 for M=H (Formula 1). For substituents M other than H the aldehyde group is simply replaced by the corresponding ketone.

Scheme 1

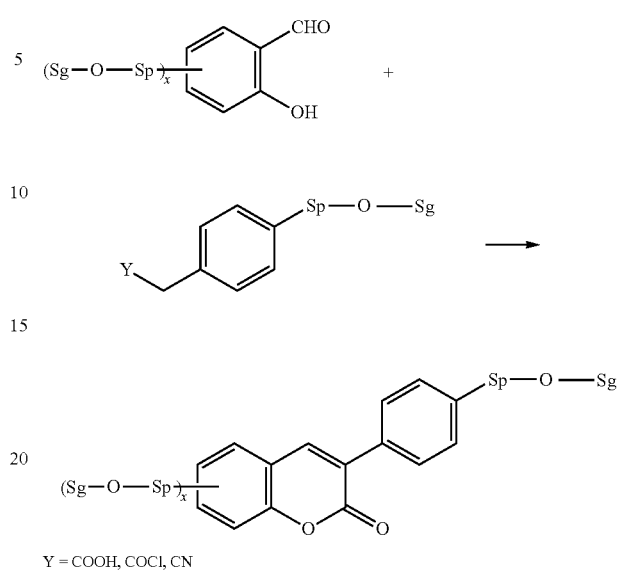

Y = COOH, COCl, CN

An alternative approach especially for non-aromatic acetic acid derivatives goes via a Wittig reaction as published by R. S. Mali, S. G. Tilve, S. N. Yeola, A. R. Manekar, Heterocycles (1987), 26(1), 121-7 (scheme 2).

Scheme 2

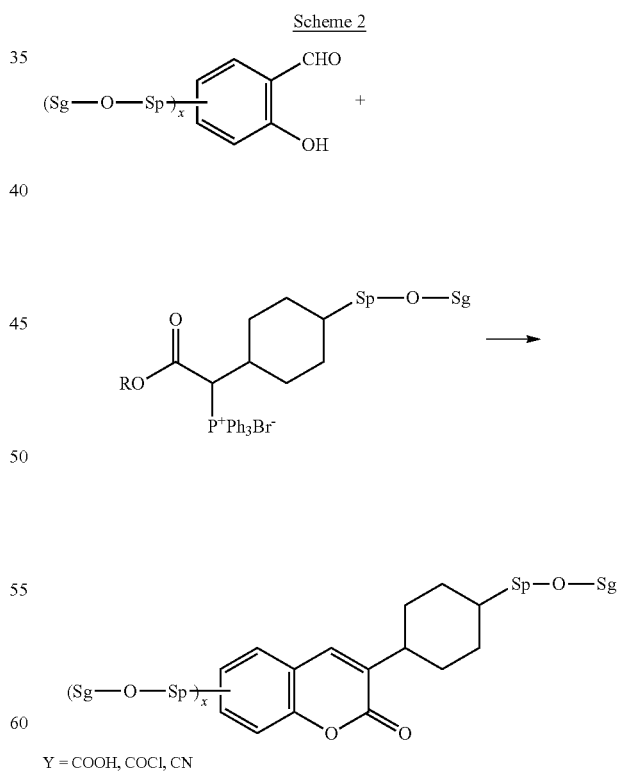

Y = COOH, COCl, CN

Spacer groups can be introduced e.g. by Sonogashira coupling of hydroxy alkynes and subsequent hydrogenation either before or after the Perkin reaction (scheme 3 and 4).

Scheme 3

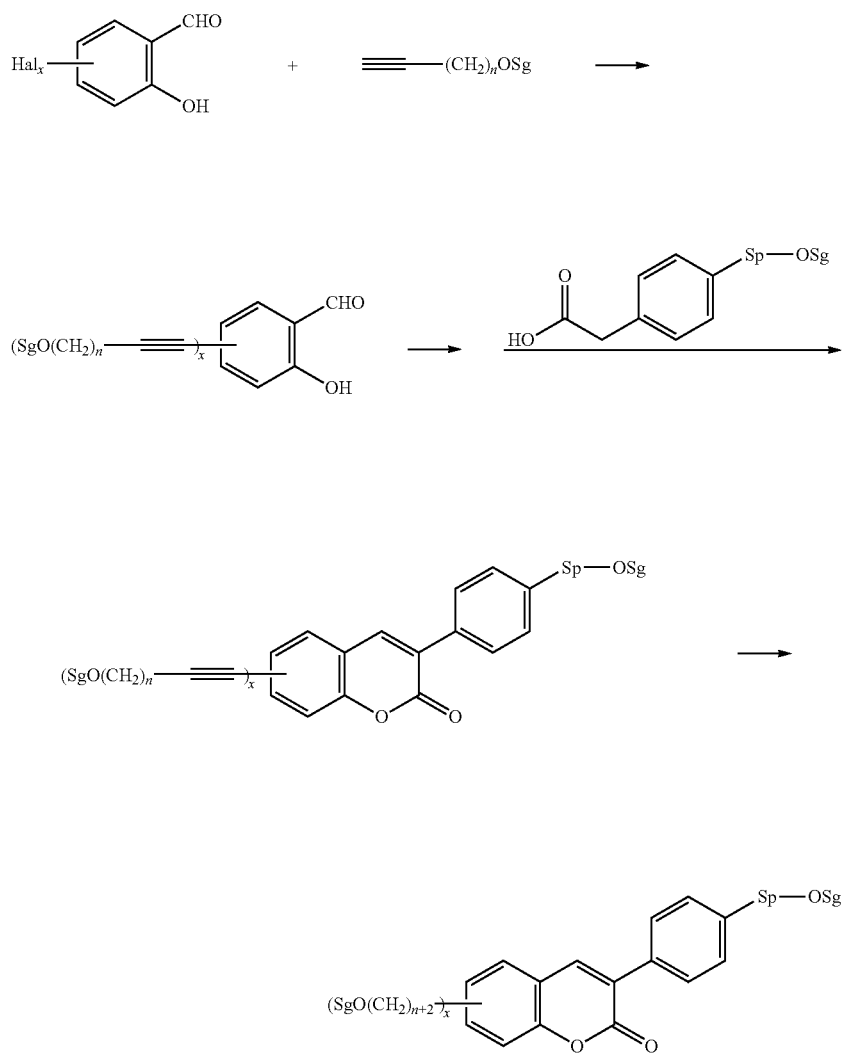

Scheme 4

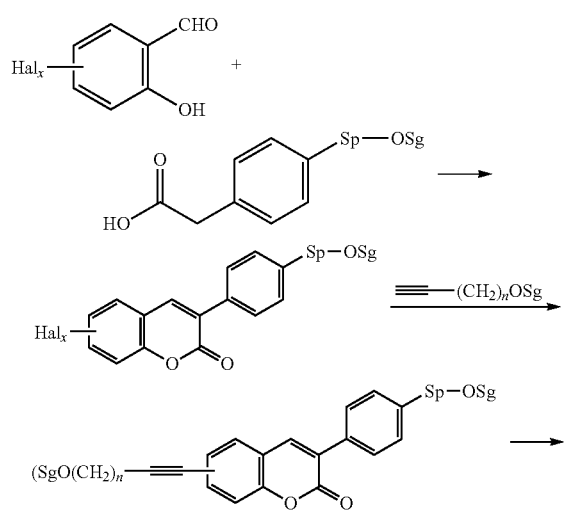

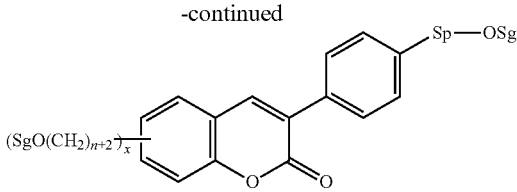

Introduction of a hydroxypropyl group by Stille coupling and subsequent hydroboration is described in B. S. Moon et al., Bioorg. Med. Chem. 2009, 17(9), 3479-3488. For a Heck reaction with allyl alcohol cf. R. A. Lerner et al., J. Am. Chem. Soc. 1996, 118, 11720-11724. Another general approach is given by in situ hydroboration of terminally unsaturated alcohols and Suzuki coupling as described e.g. in A. R. de Lera, Tetrahedron 2001, 57, 3125-3130. These reactions are exemplified by reactions to give the propyl homologue starting from a dibromosalicylic aldehyde (scheme 5) but are generally applicable to other isomers or congeners of salicylic aldehydes.

Scheme 5

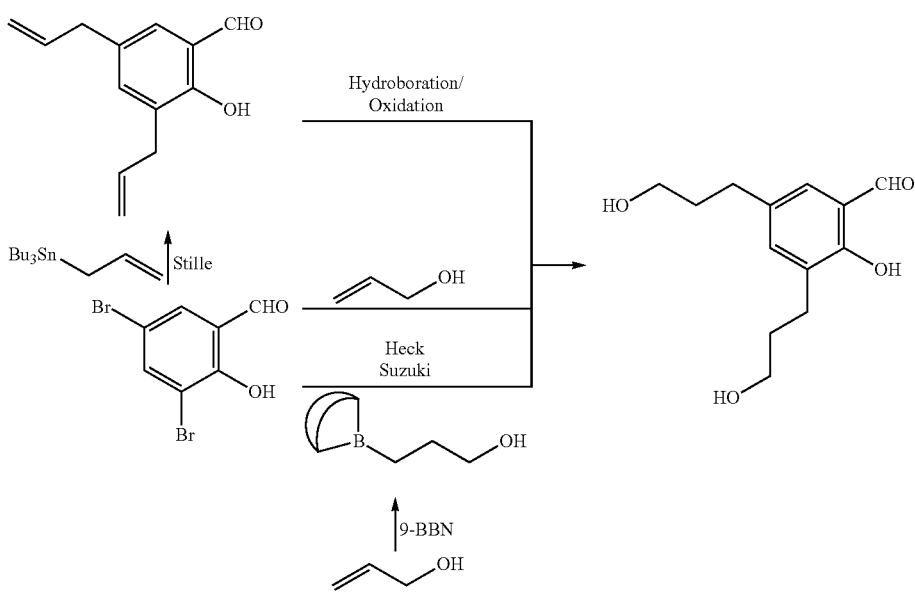

In the above scheme it can be advantageous to protect the salicylic aldehyde, esp. the aldehyde function, e.g. as an acetal. A method of protecting both the aldehyde and the hydroxyl group together is described in A. Hadfield, Synth. Comm. 1994, 24(7), 1025-1028 (Scheme 6).

Scheme 6

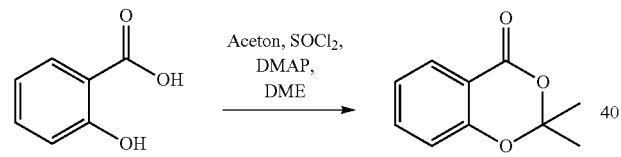

Isoflavones are accessible by the method of R. J. Bass, Chem. Comm. 1976, 78, by treatment of benzyl aryl ketones with boron trifluoride etherate in the presence of mesyl chloride in dimethylformamide. The ketones themselves can be prepared in a simple manner by carbonylating Suzuki reaction by the method of A. Suzuki et al., J. Org. Chem. 1998, 63, 4762, as shown by way of example in scheme 7:

Scheme 7

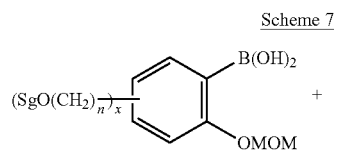

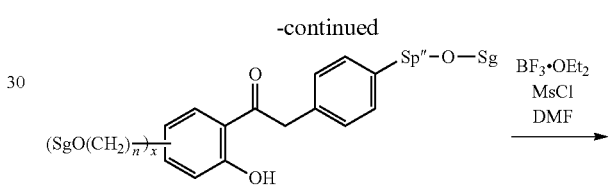

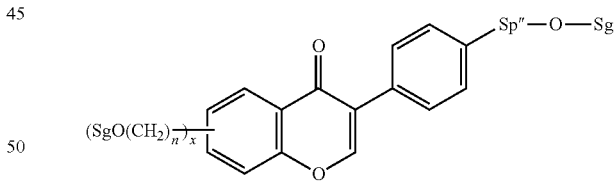

Alternatively, isoflavones can also be obtained by the method of K. M. Dawood, Tetrahedron 2007, 63, 9642, from chromanones via the corresponding bromoisoflavones by Suzuki reaction, as shown by way of example in scheme 8:

Scheme 8

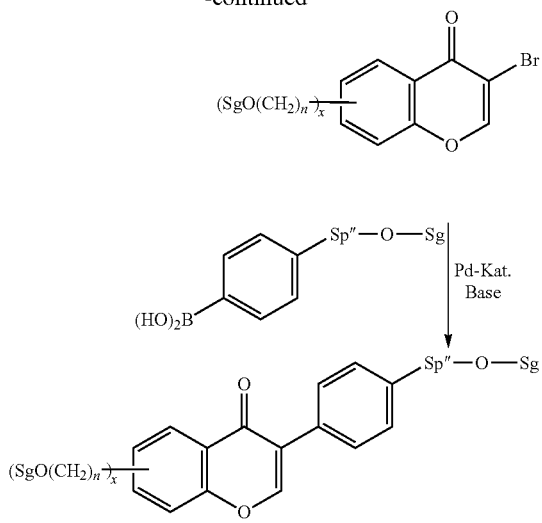

The flavones according to the invention are prepared, for example, by Baker-Venkataraman rearrangement (W. Baker, Nature 1952, 169, 706) or they can be prepared by the method of E. U. Mughal et al., Bioorg. Med. Chem. 2006, 14, 4704, from o-acylphenols by aldol condensation with aromatic aldehydes and subsequent oxidative cyclisation, as shown by way of example in Scheme 9:

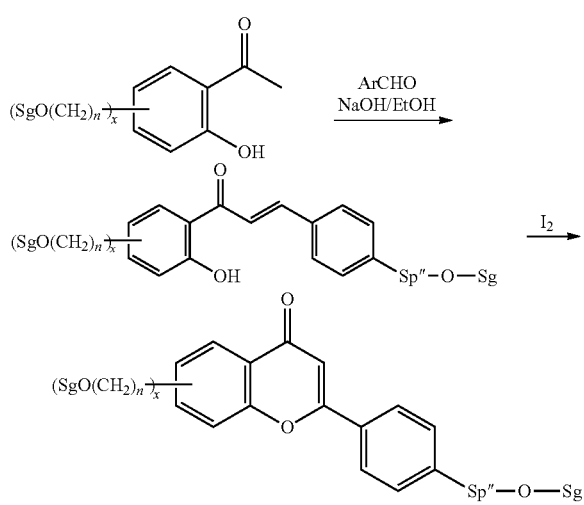

For the production of PSA displays, the polymerisable compounds are polymerised or crosslinked (if one compound contains two or more polymerisable groups) by in-situ polymerisation in the LC medium between the substrates of the LC display with application of a voltage. The polymerisation can be carried out in one step. It is also possible firstly to carry out the polymerisation with application of a voltage in a first step in order to produce a pretilt angle, and subsequently, in a second polymerisation step without an applied voltage, to polymerise or crosslink the compounds which have not reacted in the first step ("end curing").

Suitable and preferred polymerisation methods are, for example, thermal or photopolymerisation, preferably photopolymerisation, in particular UV photopolymerisation. One or more initiators can optionally also be added here. Suitable conditions for the polymerisation and suitable types and amounts of initiators are known to the person skilled in the art and are described in the literature. Suitable for free-radical polymerisation are, for example, the commercially available photoinitiators Irgacure651®, Irgacure184®, Irgacure907®, Irgacure369® or Darocure1173® (Ciba AG). If an initiator is employed, its proportion is preferably 0.001 to 5% by weight, particularly preferably 0.001 to 1% by weight.

The polymerisable compounds according to the invention are also suitable for polymerisation without an initiator, which is accompanied by considerable advantages, such, for example, lower material costs and in particular less contamination of the LC medium by possible residual amounts of the initiator or degradation products thereof. The polymerisation can thus also be carried out without the addition of an initiator. In a preferred embodiment, the LC medium thus comprises no polymerisation initiator.

The polymerisable component A) or the LC medium may also comprise one or more stabilisers in order to prevent undesired spontaneous polymerisation of the RMs, for example during storage or transport. Suitable types and amounts of stabilisers are known to the person skilled in the art and are described in the literature. Particularly suitable are, for example, the commercially available stabilisers from the Irganox® series (Ciba AG), such as, for example, Irganox® 1076. If stabilisers are employed, their proportion, based on the total amount of RMs or the polymerisable component A), is preferably 10-500,000 ppm, particularly preferably 50-50,000 ppm.

The LC media according to the invention for use in PSA displays preferably comprise from >0 to <5% by weight, particularly preferably from >0 to <1% by weight, very particularly preferably from 0.01 to 0.5% by weight, of polymerisable compounds, in particular polymerisable compounds of the formulae indicated above.

Particular preference is given to LC media comprising one, two or three polymerisable compounds according to the invention.

Preference is furthermore given to LC media in which the polymerisable component (component A) comprises exclusively polymerisable compounds according to the invention.

Preference is furthermore given to LC media in which component B) is an LC compound or an LC mixture which has a nematic liquid-crystal phase.

Preference is furthermore given to achiral polymerisable compounds according to the invention and LC media in which the compounds of component A) and/or B) are selected exclusively from the group consisting of achiral compounds.

Preference is furthermore given to LC media in which the polymerisable component or component A) comprises one or more polymerisable compounds according to the invention containing one polymerisable group (monoreactive) and one or more polymerisable compounds according to the invention containing two or more, preferably two, polymerisable groups (di- or multireactive).

Preference is furthermore given to PSA displays and LC media in which the polymerisable component or component A) comprises exclusively polymerisable compounds according to the invention containing two polymerisable groups (direactive).

The proportion of the polymerisable component or component A) in the LC media according to the invention is preferably from >0 to <5%, particularly preferably from >0 to <1%, very particularly preferably from 0.01 to 0.5%.

The proportion of the liquid-crystalline component or component B) in the LC media according to the invention is preferably from 95 to <100%, particularly preferably from 99 to <100%.

The polymerisable compounds according to the invention can be polymerised individually, but it is also possible to polymerise mixtures which comprise two or more polymerisable compounds according to the invention, or mixtures comprising one or more polymerisable compounds according to the invention and one or more further polymerisable compounds (comonomers), which are preferably mesogenic or liquid-crystalline. In the case of polymerisation of such mixtures, copolymers form. The invention furthermore relates to the polymerisable mixtures mentioned above and below. The polymerisable compounds and comonomers are mesogenic or non-mesogenic, preferably mesogenic or liquid-crystalline.

Suitable and preferred mesogenic comonomers, particularly for use in PSA displays, are selected, for example, from the following formulae:

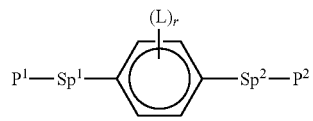
M1

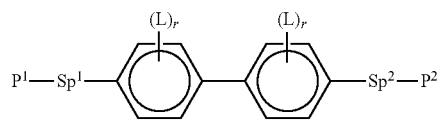
M2

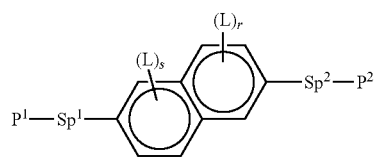
M3

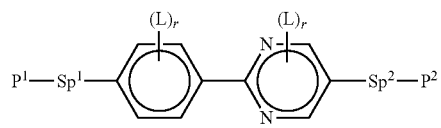
M4

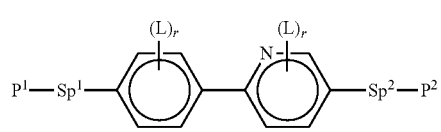
M5

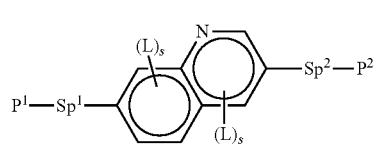
M6

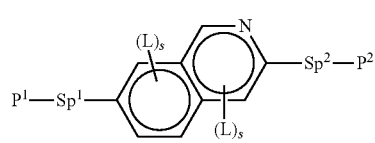
M7

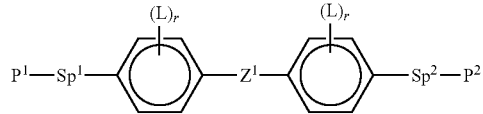
M8

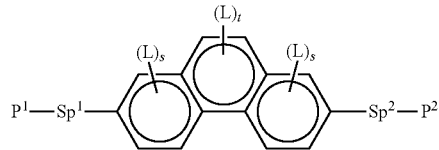
M9

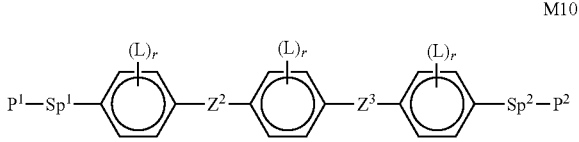
M10

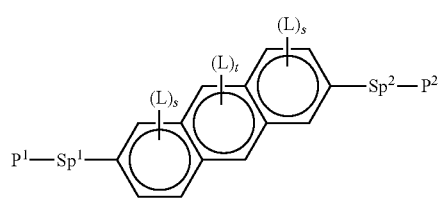
M11

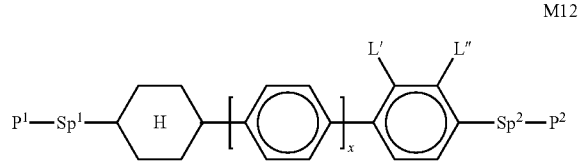
M12

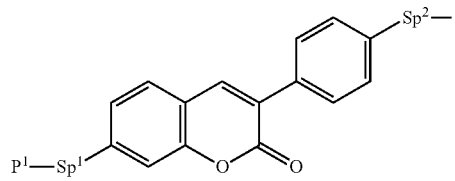
M13

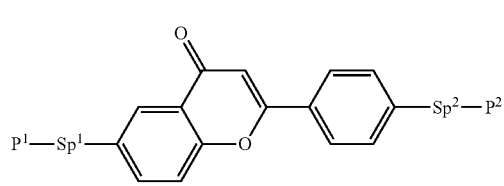
M14

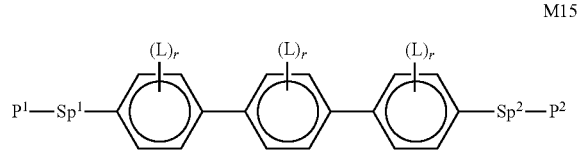
M15

M16

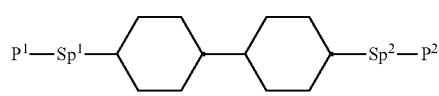
M17

-continued

M18 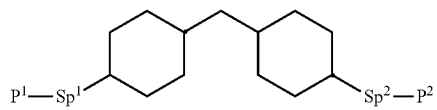

M19 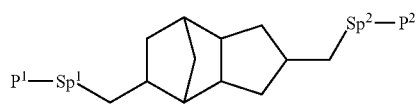

M20 

M21 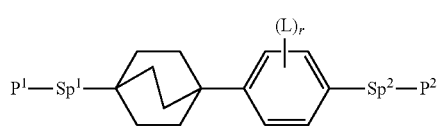

M22 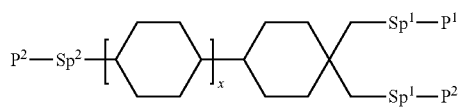

M23 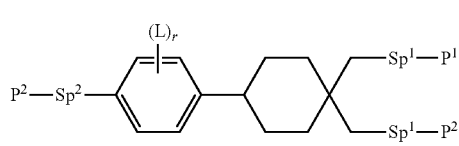

M24 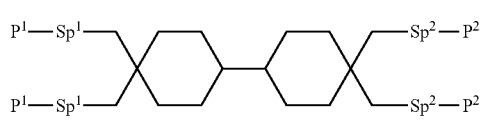

M25 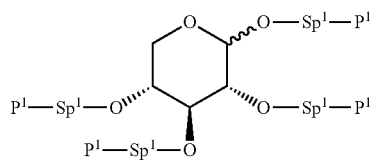

M26 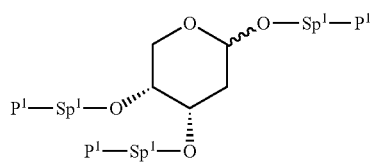

M27 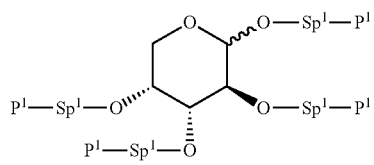

M28 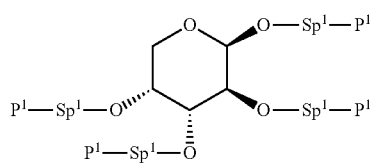

-continued

M29 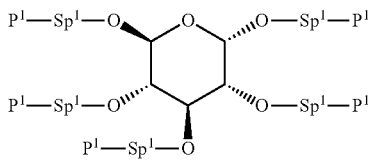

in which the individual radicals have the following meanings:

$P^1$ and $P^2$ each, independently of one another, denote a polymerisable group, preferably having one of the meanings indicated above and below for P, particularly preferably an acrylate, methacrylate, fluoroacrylate, oxetane, vinyl, vinyloxy or epoxide group, $Sp^1$ and $Sp^2$ each, independently of one another, denote a single bond or a spacer group, preferably having one of the meanings indicated above and below for Sp, and particularly preferably denote $-(CH_2)_{p1}-$, $-(CH_2)_{p1}-O-$, $-(CH_2)_{p1}-CO-O-$ or $-(CH_2)_{p1}-O-CO-O-$, in which p1 is an integer from 1 to 12, and where the linking to the adjacent ring in the last-mentioned groups takes place via the O atom, where, in addition, one or more of the radicals $P^1$-$Sp^1$- and $P^2$-$Sp^2$- may denote $R^{aa}$, with the proviso that at least one of the radicals $P^1$-$Sp^1$- and $P^2$-$Sp^2$- present does not denote $R^{aa}$, $R^{aa}$ denotes H, F, Cl, CN or straight-chain or branched alkyl having 1 to 25 C atoms, in which, in addition, one or more non-adjacent $CH_2$ groups may each be replaced, independently of one another, by $C(R^0)=C(R^{00})-$, $-C\equiv C-$, $-N(R^0)-$, $-O-$, $-S-$, $-CO-$, $-CO-O-$, $-O-CO-$, $-O-CO-O-$ in such a way that O and/or S atoms are not linked directly to one another, and in which, in addition, one or more H atoms may be replaced by F, Cl, CN or $P^1-Sp^1-$, particularly preferably straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms (where the alkenyl and alkynyl radicals have at least two C atoms and the branched radicals have at least three C atoms), $R^0$, $R^{00}$ each, independently of one another and identically or differently on each occurrence, denote H or alkyl having 1 to 12 C atoms, $R^y$ and $R^z$ each, independently of one another, denote H, F, $CH_3$ or $CF_3$, $Z^1$ denotes $-O-$, $-CO-$, $-C(R^yR^z)-$ or $-CF_2CF_2-$, $Z^2$ and $Z^3$ each, independently of one another, denote $-CO-O-$, $-O-CO-$, $-CH_2O-$, $-OCH_2-$, $-CF_2O-$, $-OCF_2-$ or $-(CH_2)_n-$, where n is 2, 3 or 4, L on each occurrence, identically or differently, denotes F, Cl, CN or straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms, preferably F, L' and L" each, independently of one another, denote H, F or Cl, r denotes 0, 1, 2, 3 or 4, s denotes 0, 1, 2 or 3, t denotes 0, 1 or 2, x denotes 0 or 1.

In the compounds of formulae M1 to M29

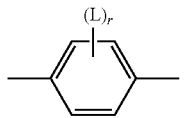

is preferably

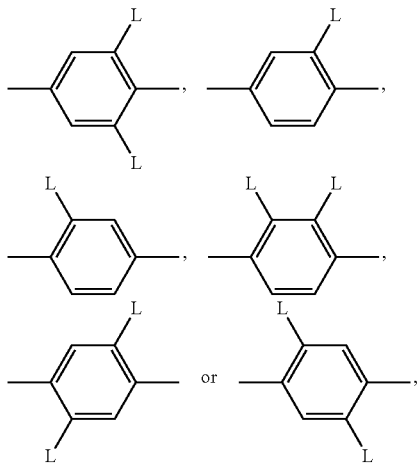

wherein L on each occurrence, identically or differently, has one of the meanings given above or below, and is preferably F, Cl, CN, NO$_2$, CH$_3$, C$_2$H$_5$, C(CH$_3$)$_3$, CH(CH$_3$)$_2$, CH$_2$CH (CH$_3$)C$_2$H$_5$, OCH$_3$, OC$_2$H$_5$, COCH$_3$, COC$_2$H$_5$, COOCH$_3$, COOC$_2$H$_5$, CF$_3$, OCF$_3$, OCHF$_2$, OC$_2$F$_5$ or P-Sp-, very preferably F, Cl, CN, CH$_3$, C$_2$H$_5$, OCH$_3$, COCH$_3$, OCF$_3$ or P-Sp-, more preferably F, Cl, CH$_3$, OCH$_3$, COCH$_3$ oder OCF$_3$, especially F or CH$_3$. Besides the polymerisable compounds described above, the LC media for use in the LC displays according to the invention comprise an LC mixture ("host mixture") comprising one or more, preferably two or more, low-molecular-weight (i.e. monomeric or unpolymerised) compounds. The latter are stable or unreactive to a polymerisation reaction under the conditions used for polymerisation of the polymerisable compounds. In principle, any LC mixture which is suitable for use in conventional VA and OCB displays is suitable as host mixture. Suitable LC mixtures are known to the person skilled in the art and are described in the literature, for example mixtures in VA displays in EP 1 378 557 A1 and mixtures for OCB displays in EP 1 306 418 A1 and DE 102 24 046 A1.

The polymerisable compounds of formula I are especially suitable for use in an LC host mixture that comprises one or more compounds having a terminal alkenyl group, where they show improved properties, like solubility, reactivity or capability of generating a tilt angle, compared to reactive mesogens known from prior art.

In a first preferred embodiment the LC medium contains an LC host mixture based on compounds with negative dielectric anisotropy. Such LC media are especially suitable for use in PSA-VA displays. Particularly preferred embodiments of such an LC medium are those of sections a)-x) below:

a) LC medium which comprises one or more compounds of the formulae CY and/or PY:

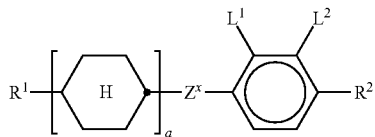

CY

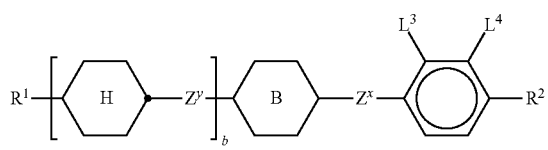

PY wherein
a denotes 1 or 2,
b denotes 0 or 1.

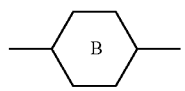

denotes

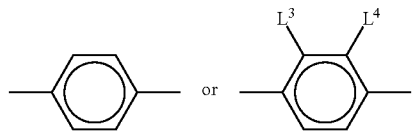

R$^1$ and R$^2$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another, preferably alkyl or alkoxy having 1 to 6 C atoms, Z$^x$ and Z$^y$ each, independently of one another, denote —CH$_2$CH$_2$—, —CH=CH—, —CF$_2$O—, —OCF$_2$—, —CH$_2$O—, —OCH$_2$—, —CO—O—, —O—CO—, —C$_2$F$_4$—, —CF=CF—, —CH=CH—CH$_2$O— or a single bond, preferably a single bond, L$^{1-4}$ each, independently of one another, denote F, Cl, OCF$_3$, CF$_3$, CH$_3$, CH$_2$F, CHF$_2$.

Preferably, both L$^1$ and L$^2$ denote F or one of L$^1$ and L$^2$ denotes F and the other denotes Cl, or both L$^3$ and L$^4$ denote F or one of L$^3$ and L$^4$ denotes F and the other denotes Cl.

The compounds of the formula CY are preferably selected from the group consisting of the following sub-formulae:

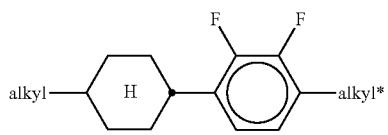

CY1

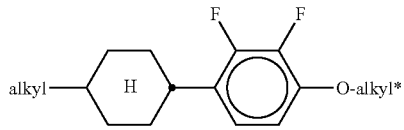

CY2

CY3
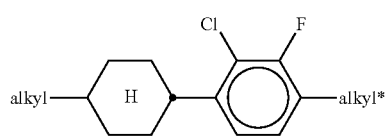
CY4
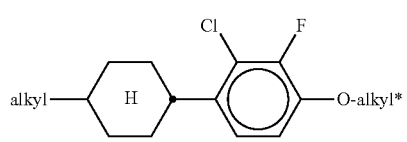
CY5
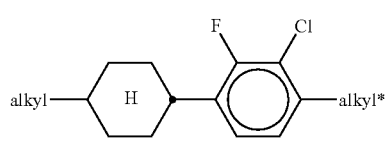
CY6
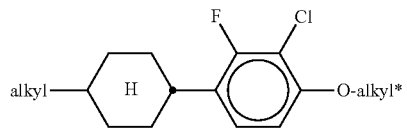
CY7
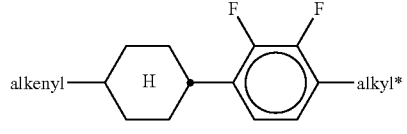
CY8
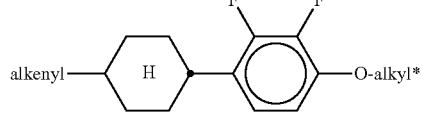
CY9
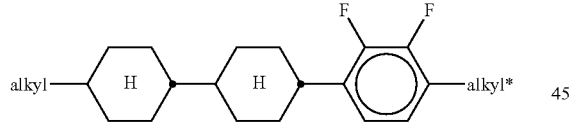
CY10
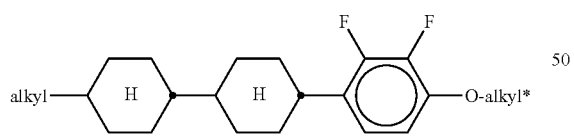
CY11
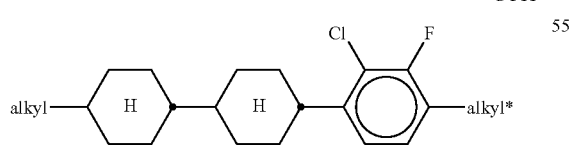
CY12
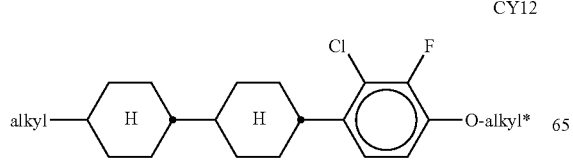
CY13
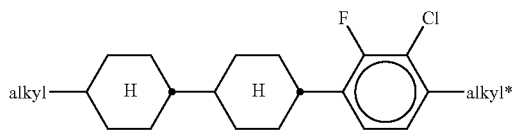
CY14
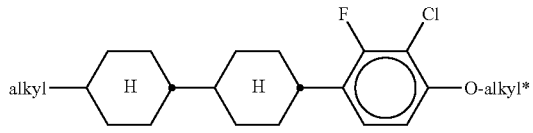
CY15
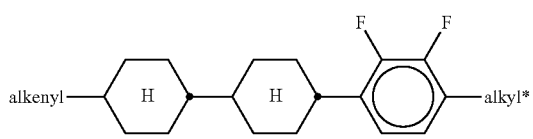
CY16
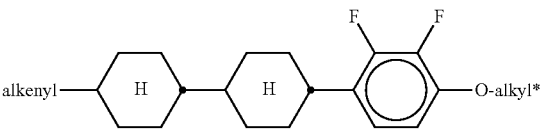
CY17
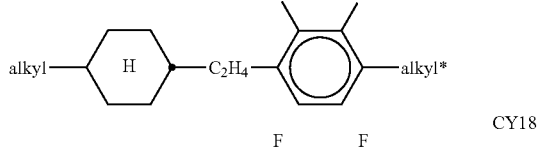
CY18
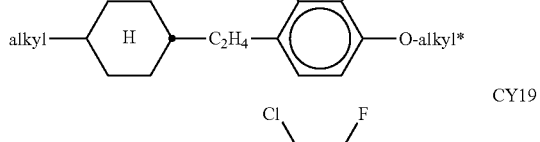
CY19
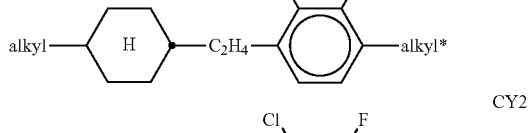
CY20
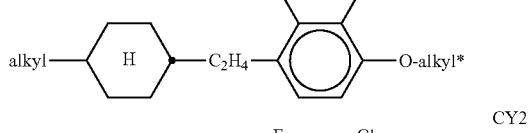
CY21
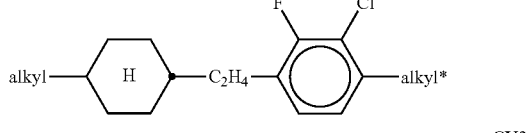
CY22
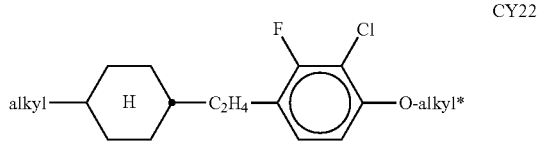
CY23
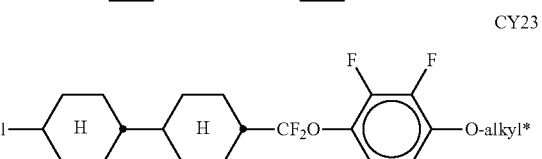

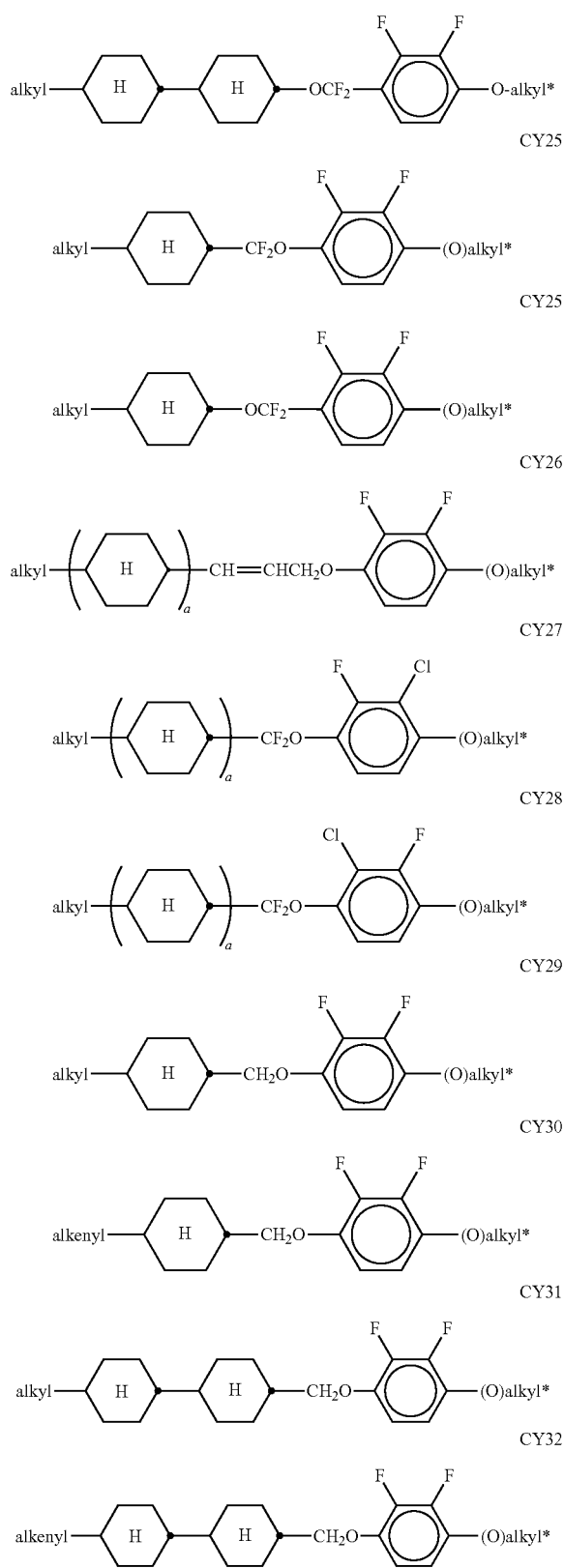

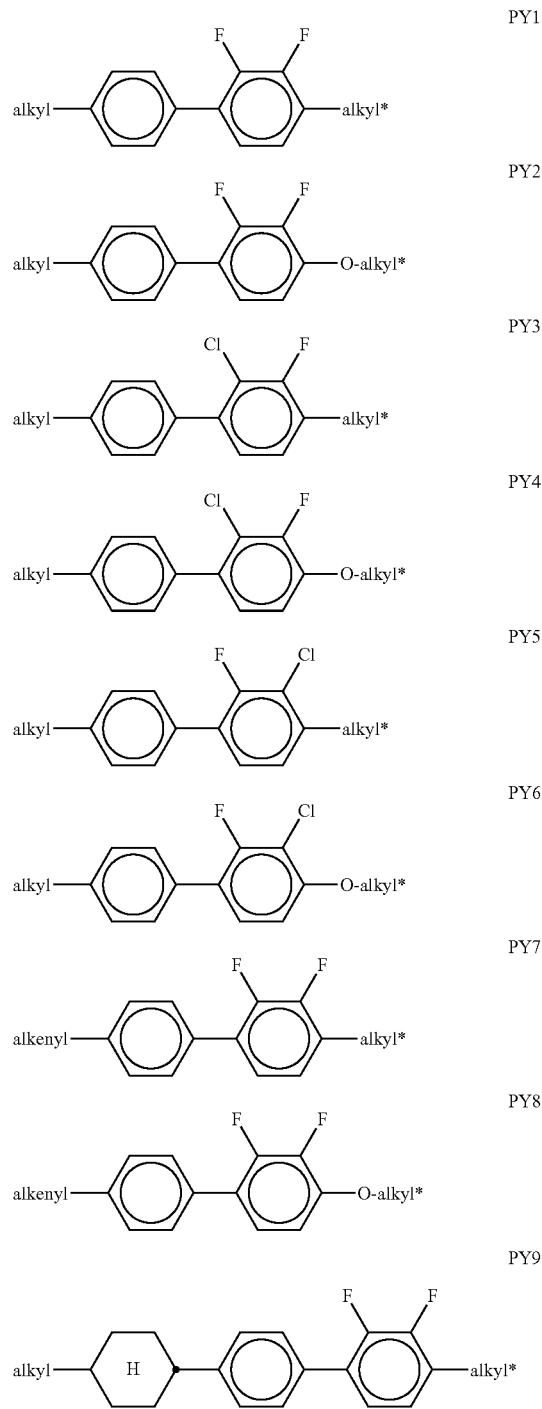

in which a denotes 1 or 2, alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

The compounds of the formula PY are preferably selected from the group consisting of the following sub-formulae:

PY10

[structure: alkyl—H—◯—◯(2,3-diF)—O-alkyl*]

PY11

[structure: alkyl—H—◯—◯(2-Cl,3-F)—alkyl*]

PY12

[structure: alkyl—H—◯—◯(2-Cl,3-F)—O-alkyl*]

PY13

[structure: alkyl—H—◯—◯(2-F,3-Cl)—alkyl*]

PY14

[structure: alkyl—H—◯—◯(2-F,3-Cl)—O-alkyl*]

PY15

[structure: alkenyl—H—◯—◯(2,3-diF)—alkyl*]

PY16

[structure: alkenyl—H—◯—◯(2,3-diF)—O-alkyl*]

PY17

[structure: alkyl—H—CH=CH—◯—◯(2,3-diF)—(O)alkyl*]

PY18

[structure: alkyl—H—C₂H₄—◯—◯(2,3-diF)—(O)alkyl*]

PY19

[structure: alkyl—H—◯—OCF₂—◯(2,3-diF)—(O)alkyl*]

PY20

[structure: alkyl—H—◯—CF₂O—◯(2,3-diF)—(O)alkyl*]

in which alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

b) LC medium which additionally comprises one or more compounds of the following formula:

ZK $$R^3-\boxed{C}-Z^y-\boxed{D}-R^4$$

in which the individual radicals have the following meanings:

$\boxed{C}$ denotes

[cyclohexane with H], [tetrahydropyran], [tetrahydropyran isomer], [cyclohexene] or $\boxed{D}$ denotes

[cyclohexane with H] or [phenyl], $R^3$ and $R^4$ each, independently of one another, denote alkyl having 1 to 12 C atoms, in which, in addition, one or two non-adjacent $CH_2$ groups may be replaced by —O—, —CH=CH—, —CO—, —O—CO— or —CO—O— in such a way that O atoms are not linked directly to one another, $Z^y$ denotes —CH$_2$CH$_2$—, —CH=CH—, —CF$_2$O—, —OCF$_2$—, —CH$_2$O—, —OCH$_2$—, —CO—O—, —O—CO—, —C$_2$F$_4$—, —CF=CF—, —CH=CH—CH$_2$O— or a single bond, preferably a single bond.

The compounds of the formula ZK are preferably selected from the group consisting of the following sub-formulae:

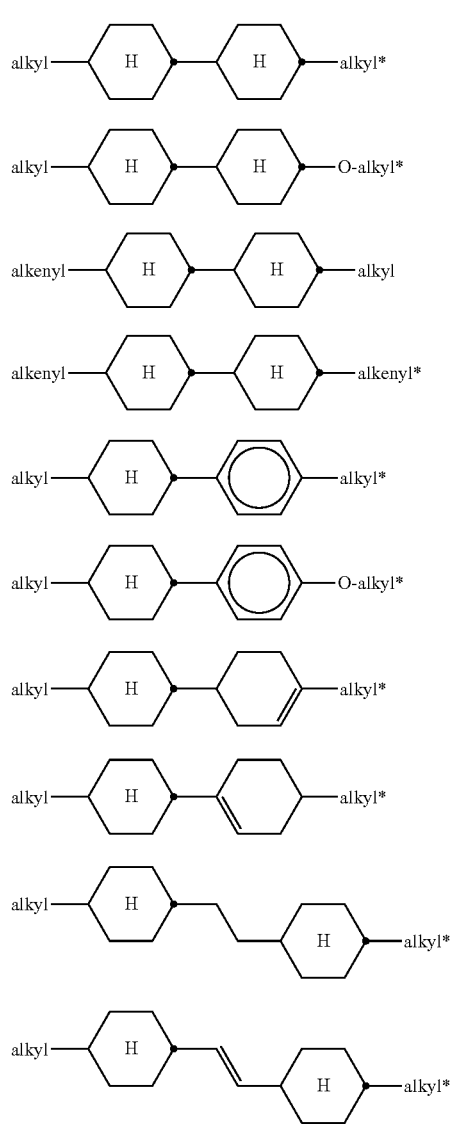

in which alkyl and alkyl* each, independently of one another, denote a straight-chain alkyl radical having 1-6 C atoms, and alkenyl denotes a straight-chain alkenyl radical having 2-6 C atoms. Alkenyl preferably denotes CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

c) LC medium which additionally comprises one or more compounds of the following formula:

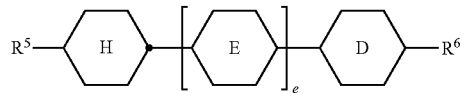

in which the individual radicals on each occurrence, identically or differently, have the following meanings:

$R^5$ and $R^6$ each, independently of one another, have one of the meanings indicated above for $R^1$,

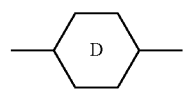

denotes

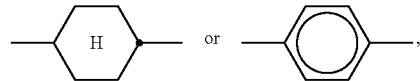

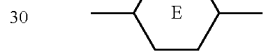

denotes

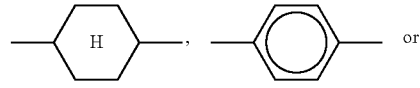

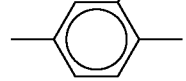

and e denotes 1 or 2.

The compounds of the formula DK are preferably selected from the group consisting of the following sub-formulae:

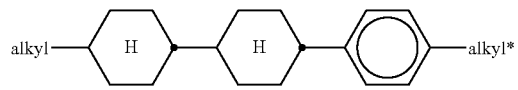

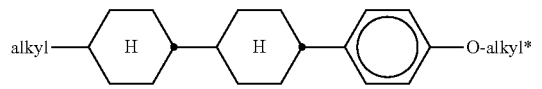

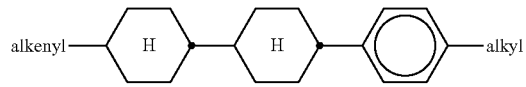

-continued

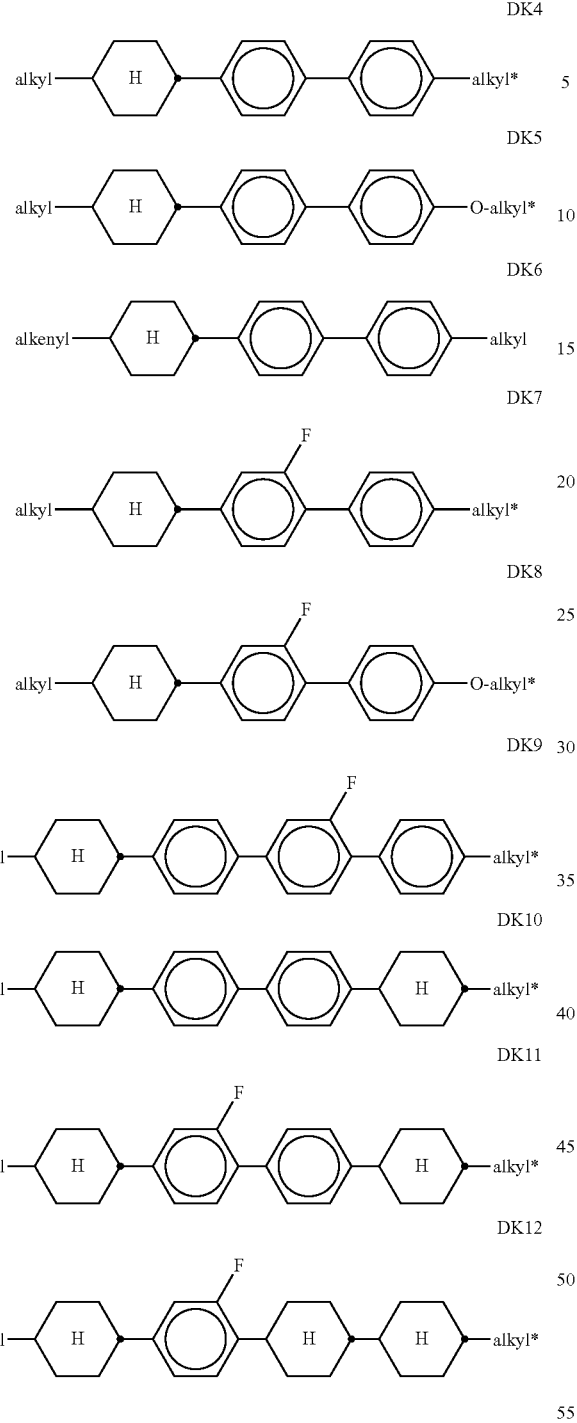

in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms. Alkenyl and alkenyl* preferably denote CH₂=CH—, CH₂=CHCH₂CH₂—, CH₃—CH=CH—, CH₃—CH₂—CH=CH—, CH₃—(CH₂)₂—CH=CH—, CH₃—(CH₂)₃—CH=CH— or CH₃—CH=CH—(CH₂)₂—.

d) LC medium which additionally comprises one or more compounds of the following formula:

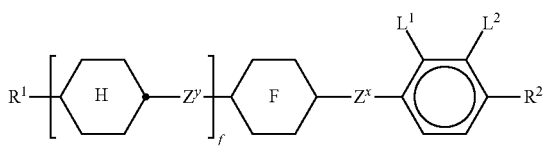

in which the individual radicals have the following meanings:

denotes

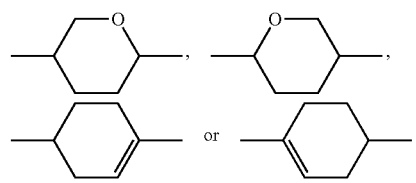

f denotes 0 or 1,
R¹ and R² each, independently of one another, denote alkyl having 1 to 12 C atoms, where, in addition, one or two non-adjacent CH₂ groups may be replaced by —O—, —CH=CH—, —CO—, —OCO— or —COO— in such a way that O atoms are not linked directly to one another,
Zˣ and Zʸ each, independently of one another, denote —CH₂CH₂—, —CH=CH—, —CF₂O—, —OCF₂—, —CH₂O—, —OCH₂—, —CO—O—, —O—CO—, —C₂F₄—, —CF=CF—, —CH=CH—CH₂O— or a single bond, preferably a single bond,
L¹ and L² each, independently of one another, denote F, Cl, OCF₃, CF₃, CH₃, CH₂F, CHF₂.

Preferably, both radicals L¹ and L² denote F or one of the radicals L¹ and L² denotes F and the other denotes Cl.

The compounds of the formula LY are preferably selected from the group consisting of the following sub-formulae:

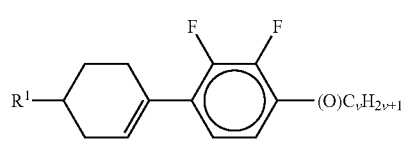

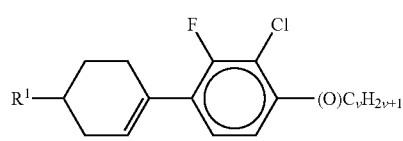

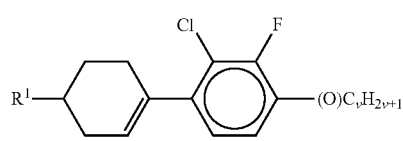

-continued

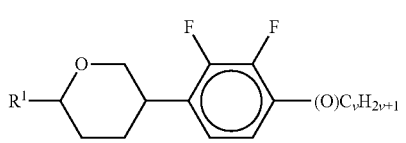
LY4

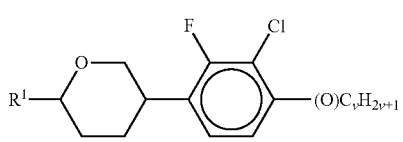
LY5

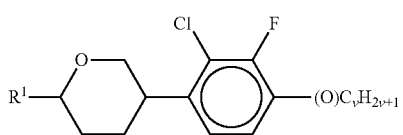
LY6

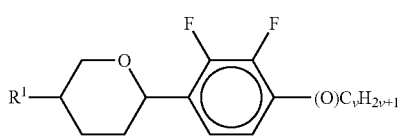
LY7

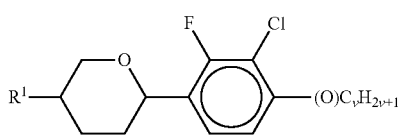
LY8

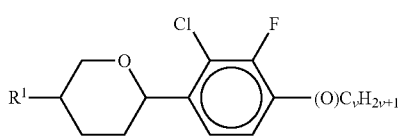
LY9

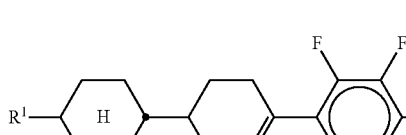
LY10

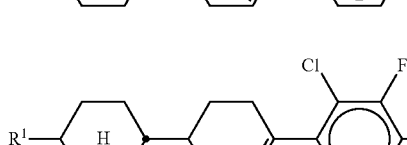
LY11

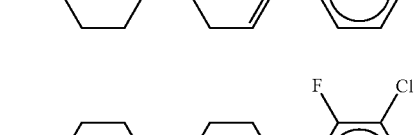
LY12

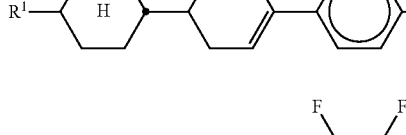
LY13

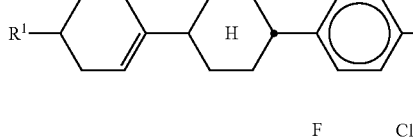
LY14

-continued

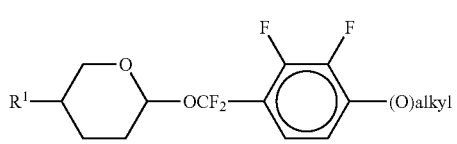
LY15

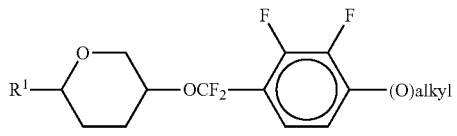
LY16

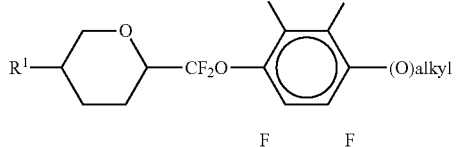
LY17

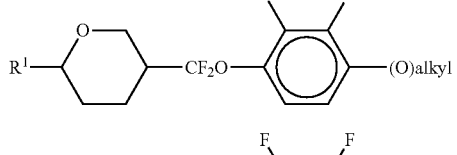
LY18

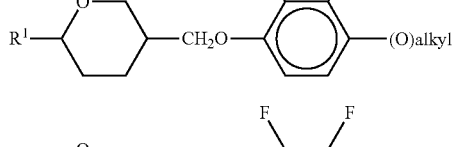
LY19

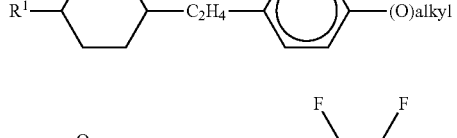
LY20

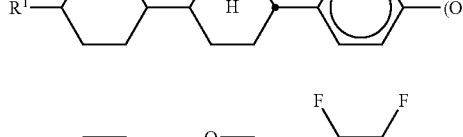
LY21

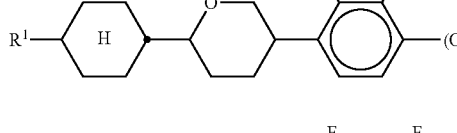
LY22

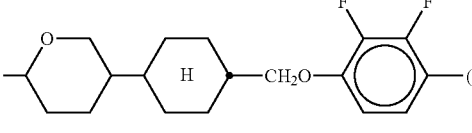
LY23

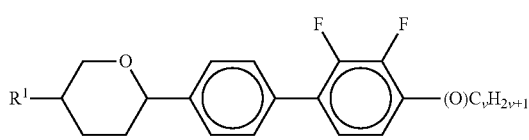
LY24 in which $R^1$ has the meaning indicated above, alkyl denotes a straight-chain alkyl radical having 1-6 C atoms, (O) denotes an oxygen atom or a single bond, and v denotes an integer from 1 to 6. $R^1$ preferably denotes straight-chain alkyl having 1 to 6 C atoms or straight-chain alkenyl having 2 to 6 C atoms, in particular CH$_3$, C$_2$H$_5$, n-C$_3$H$_7$, n-C$_4$H$_9$, n-C$_5$H$_{11}$, CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

e) LC medium which additionally comprises one or more compounds selected from the group consisting of the following formulae:

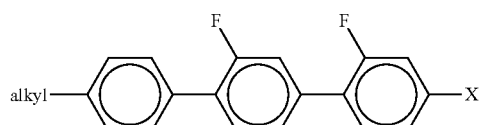
G1

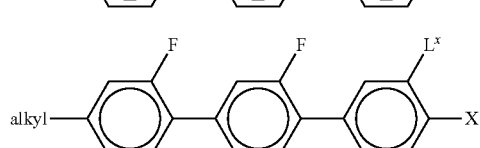
G2

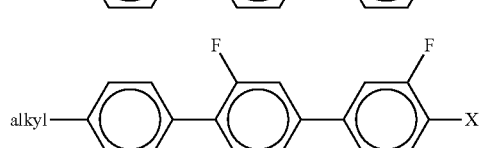
G3

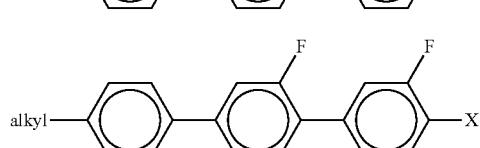
G4 in which alkyl denotes C$_{1-6}$-alkyl, L$^x$ denotes H or F, and X denotes F, Cl, OCF$_3$, OCHF$_2$ or OCH=CF$_2$. Particular preference is given to compounds of the formula G1 in which X denotes F.

f) LC medium which additionally comprises one or more compounds selected from the group consisting of the following formulae:

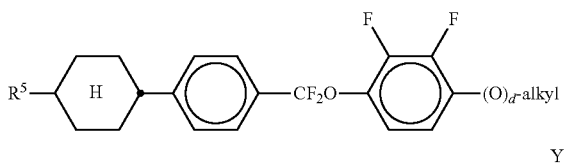
Y1

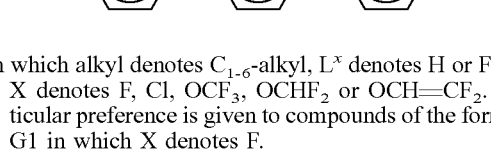
Y2

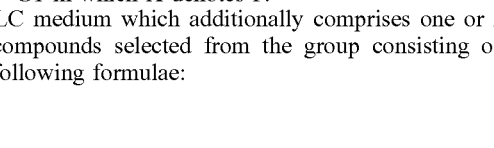
Y3

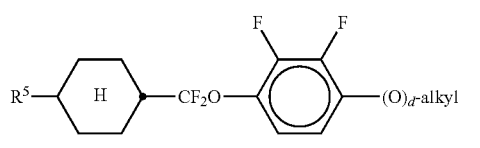
Y4

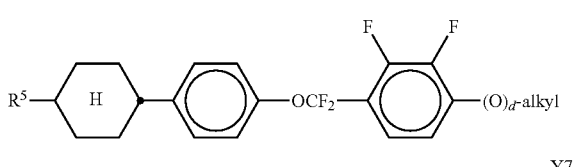
Y5

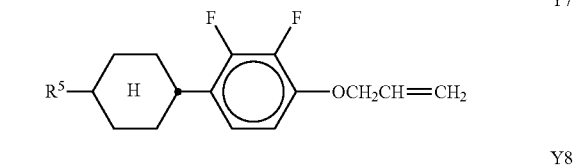
Y6

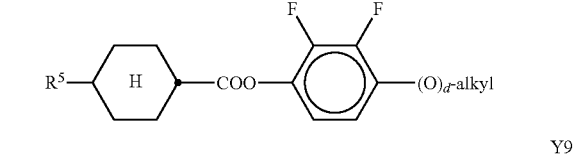
Y7

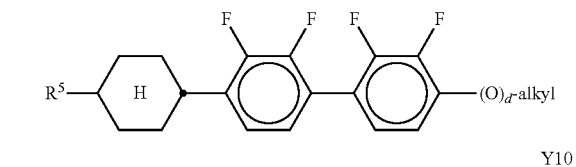
Y8

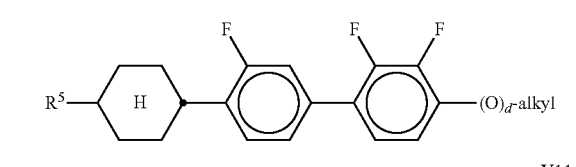
Y9

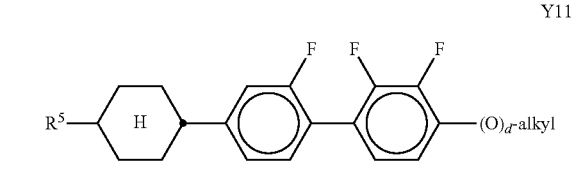
Y10

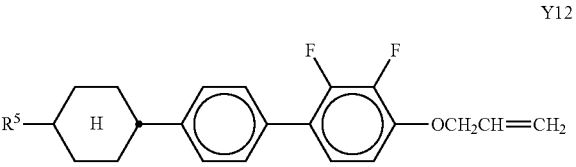
Y11

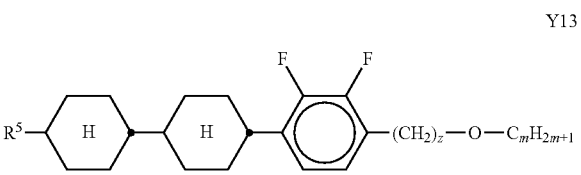
Y12

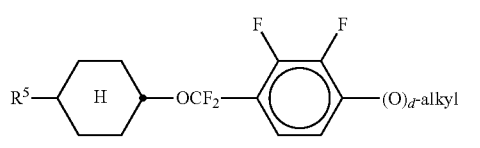
Y13

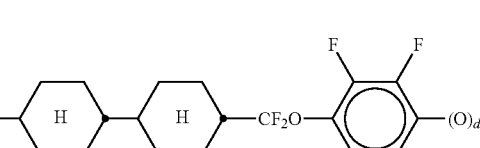

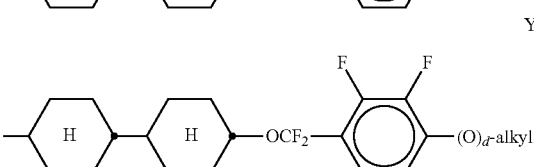
Y14

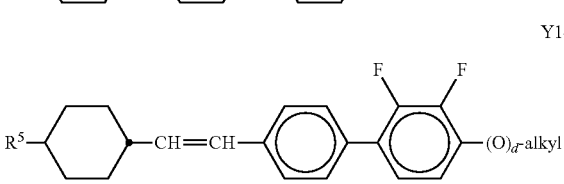

-continued

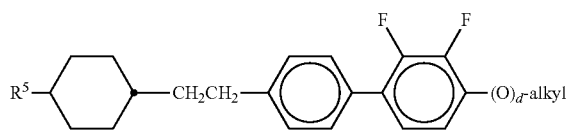

Y15

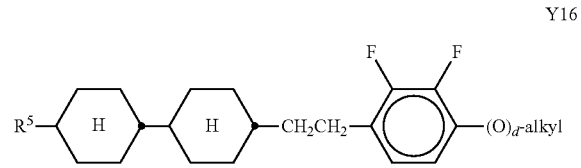

Y16 in which $R^5$ has one of the meanings indicated above for $R^1$, alkyl denotes $C_{1-6}$-alkyl, d denotes 0 or 1, and z and m each, independently of one another, denote an integer from 1 to 6. $R^5$ in these compounds is particularly preferably $C_{1-6}$-alkyl or -alkoxy or $C_{2-6}$-alkenyl, d is preferably 1. The LC medium according to the invention preferably comprises one or more compounds of the above-mentioned formulae in amounts of ≥5% by weight.

g) LC medium which additionally comprises one or more biphenyl compounds selected from the group consisting of the following formulae:

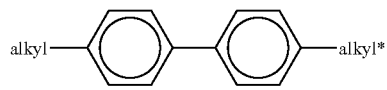

B1

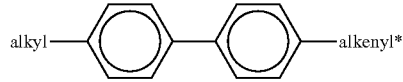

B2

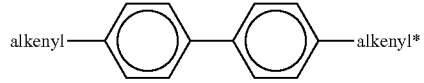

B3 in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms. Alkenyl and alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

The proportion of the biphenyls of the formulae B1 to B3 in the LC mixture is preferably at least 3% by weight, in particular ≥5% by weight.

The compounds of the formula B2 are particularly preferred.

The compounds of the formulae B1 to B3 are preferably selected from the group consisting of the following sub-formulae:

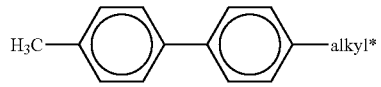

B1a

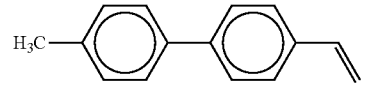

B2a

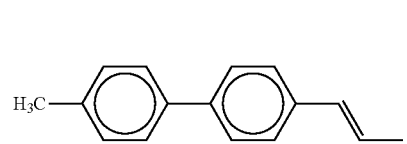

B2b

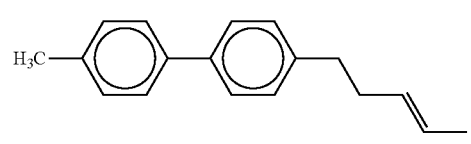

B2c in which alkyl* denotes an alkyl radical having 1-6 C atoms. The medium according to the invention particularly preferably comprises one or more compounds of the formulae B1a and/or B2c.

h) LC medium which additionally comprises one or more terphenyl compounds of the following formula:

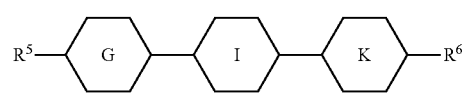

T in which $R^5$ and $R^6$ each, independently of one another, have one of the meanings indicated above for $R^1$, and

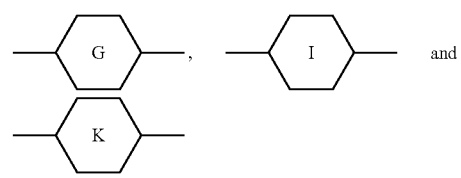

each, independently of one another, denote

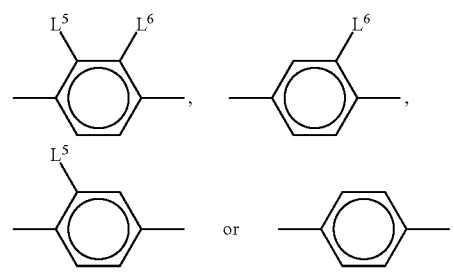

in which $L^5$ denotes F or Cl, preferably F, and $L^6$ denotes F, Cl, $OCF_3$, $CF_3$, $CH_3$, $CH_2F$ or $CHF_2$, preferably F.

The compounds of the formula T are preferably selected from the group consisting of the following sub-formulae:

T1
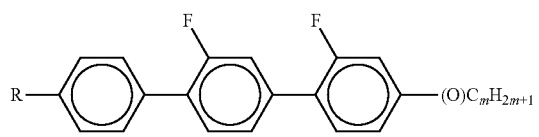
T2
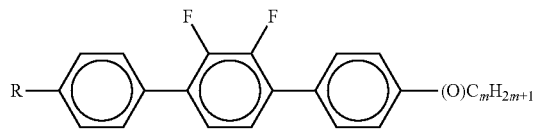
T3
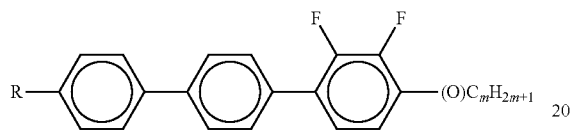
T4
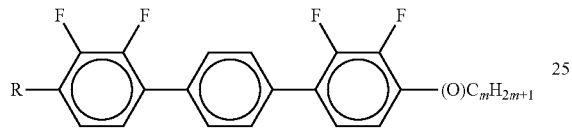
T5
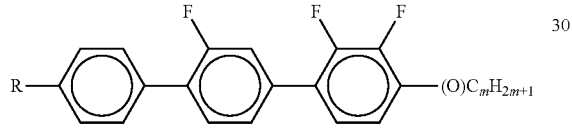
T6
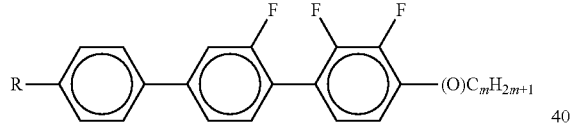
T7
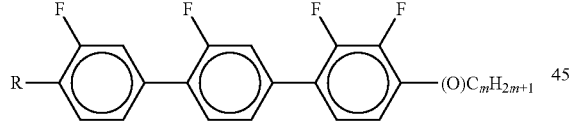
T8
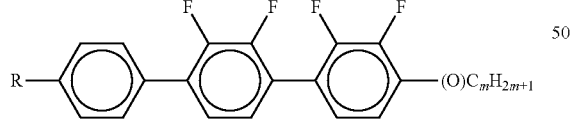
T9
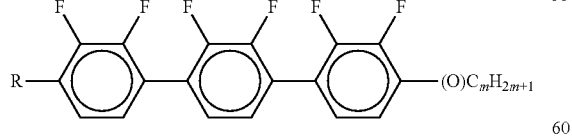
T10
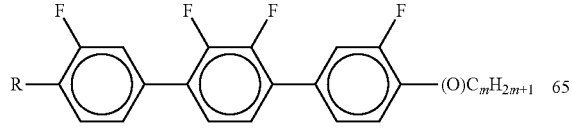
-continued
T11
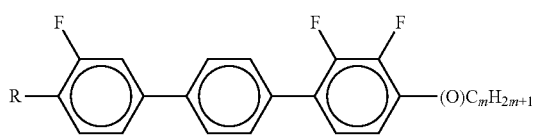
T12
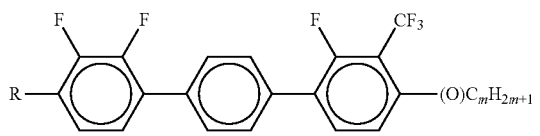
T13
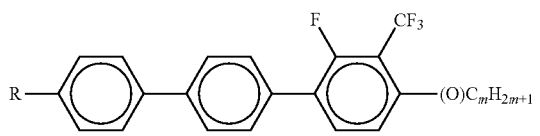
T14
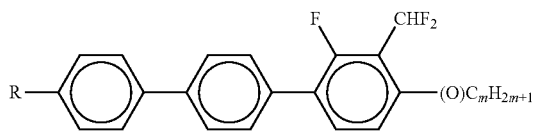
T15
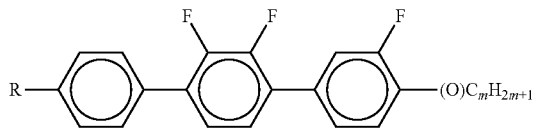
T16
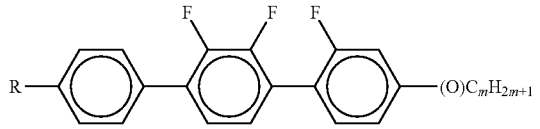
T17
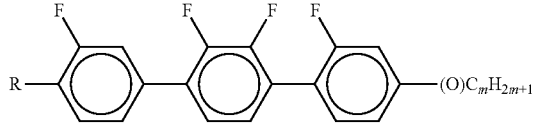
T18
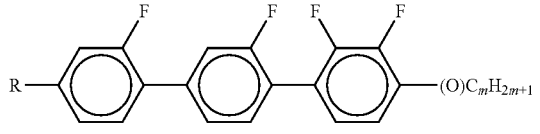
T19
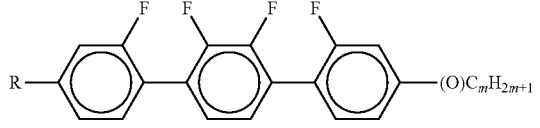
T20
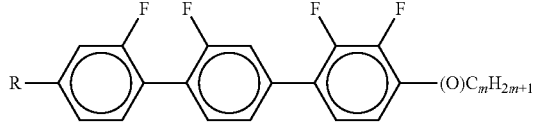

-continued

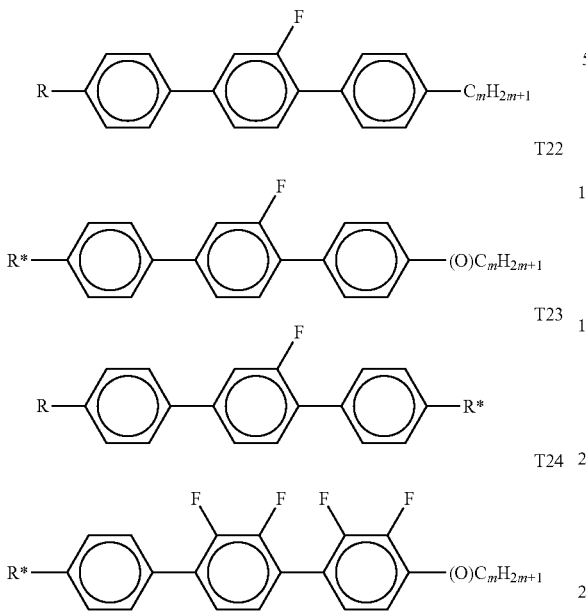

in which R denotes a straight-chain alkyl or alkoxy radical having 1-7 C atoms, R* denotes a straight-chain alkenyl radical having 2-7 C atoms, (O) denotes an oxygen atom or a single bond, and m denotes an integer from 1 to 6. R* preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

R preferably denotes methyl, ethyl, propyl, butyl, pentyl, hexyl, methoxy, ethoxy, propoxy, butoxy or pentoxy.

The LC medium according to the invention preferably comprises the terphenyls of the formula T and the preferred sub-formulae thereof in an amount of 0.5-30% by weight, in particular 1-20% by weight.

Particular preference is given to compounds of the formulae T1, T2, T3 and T21. In these compounds, R preferably denotes alkyl, furthermore alkoxy, each having 1-5 C atoms.

The terphenyls are preferably employed in mixtures according to the invention if the Δn value of the mixture is to be ≥0.1. Preferred mixtures comprise 2-20% by weight of one or more terphenyl compounds of the formula T, preferably selected from the group of compounds T1 to T22.

i) LC medium which additionally comprises one or more compounds selected from the group consisting of the following formulae:

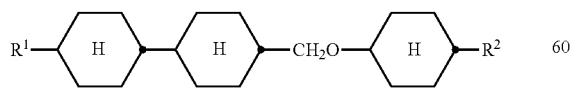

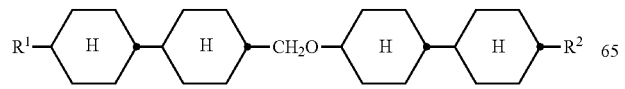

-continued

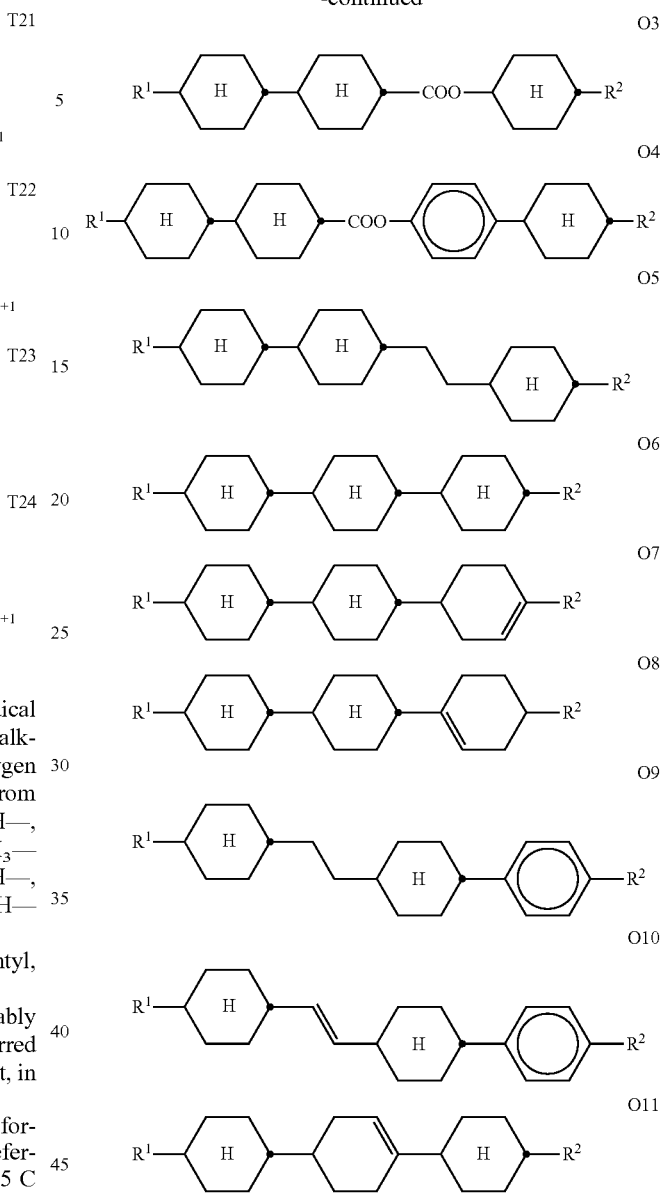

in which $R^1$ and $R^2$ have the meanings indicated above and preferably each, independently of one another, denote straight-chain alkyl having 1 to 6 C atoms or straight-chain alkenyl having 2 to 6 C atoms.

Preferred media comprise one or more compounds selected from the formulae O1, O3 and O4.

k) LC medium which additionally comprises one or more compounds of the following formula:

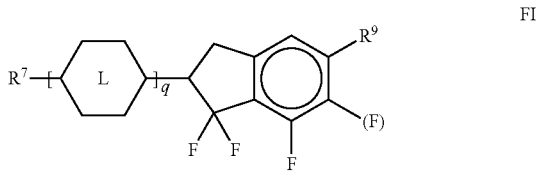

in which

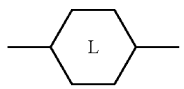

denotes

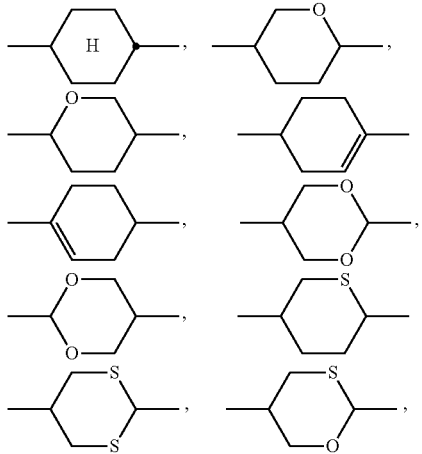

R⁹ denotes H, CH₃, C₂H₅ or n-C₃H₇, (F) denotes an optional fluorine substituent, and q denotes 1, 2 or 3, and R⁷ has one of the meanings indicated for R¹, preferably in amounts of >3% by weight, in particular ≥5% by weight and very particularly preferably 5-30% by weight.

Particularly preferred compounds of the formula FI are selected from the group consisting of the following sub-formulae:

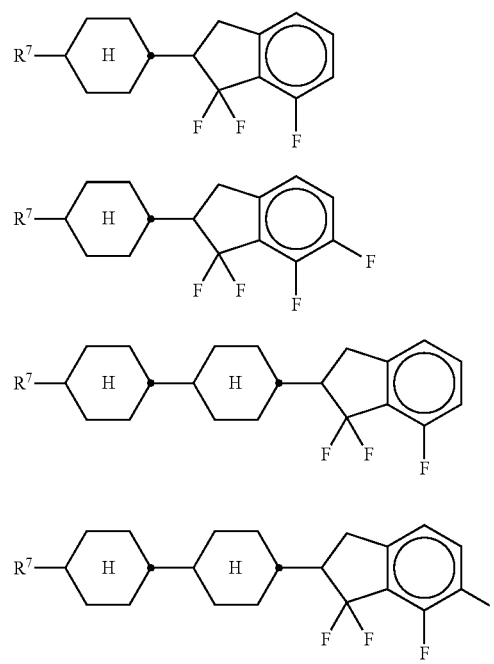

FI1

FI2

FI3

FI4

-continued

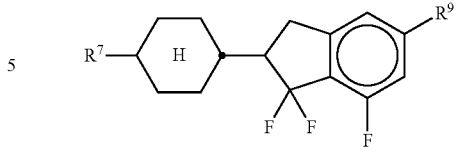

FI5

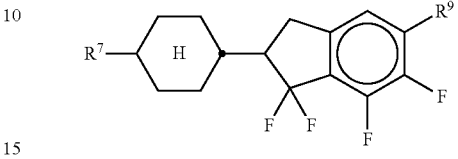

FI6

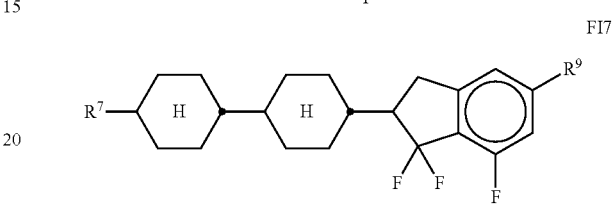

FI7

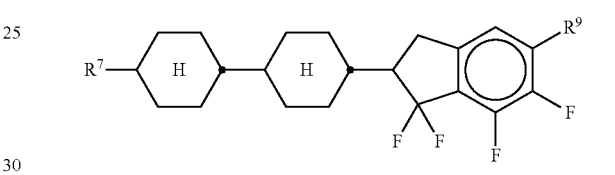

FI8 in which R⁷ preferably denotes straight-chain alkyl, and R⁹ denotes CH₃, C₂H₅ or n-C₃H₇. Particular preference is given to the compounds of the formulae FI1, FI2 and FI3.

m) LC medium which additionally comprises one or more compounds selected from the group consisting of the following formulae:

VK1

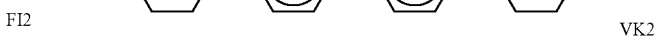

VK2

VK3

VK4 in which $R^8$ has the meaning indicated for $R^1$, and alkyl denotes a straight-chain alkyl radical having 1-6 C atoms.

n) LC medium which additionally comprises one or more compounds which contain a tetrahydronaphthyl or naphthyl unit, such as, for example, the compounds selected from the group consisting of the following formulae:

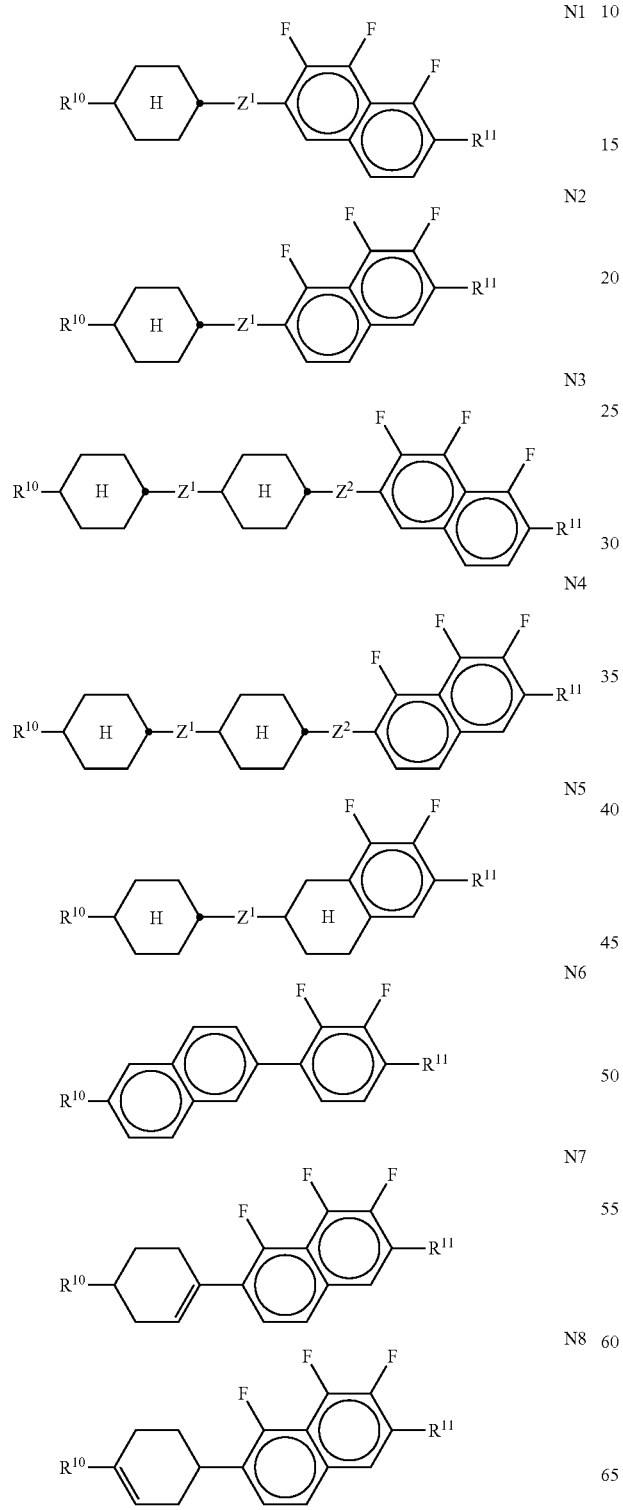

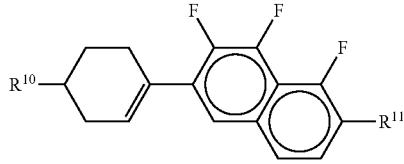

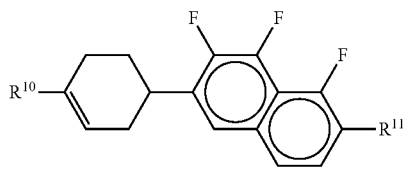

in which $R^{10}$ and $R^{11}$ each, independently of one another, have one of the meanings indicated for $R^1$, preferably denote straight-chain alkyl or alkoxy having 1 to 6 C atoms or straight-chain alkenyl having 2 to 6 C atoms, and $Z^1$ and $Z^2$ each, independently of one another, denote —$C_2H_4$—, —CH=CH—, —$(CH_2)_4$—, —$(CH_2)_3O$—, —$O(CH_2)_3$—, —CH=CH—$CH_2CH_2$—, —$CH_2CH_2$CH=CH—, —$CH_2O$—, —$OCH_2$—, —CO—O—, —O—CO—, —$C_2F_4$—, —CF=CF—, —CF=CH—, —CH=CF—, —$CH_2$— or a single bond.

o) LC medium which additionally comprises one or more difluoro-dibenzochromans and/or chromans of the following formulae:

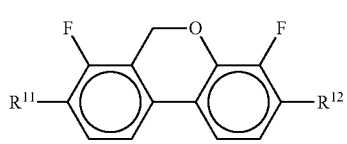

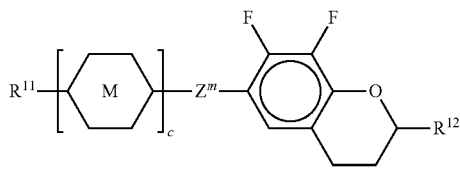

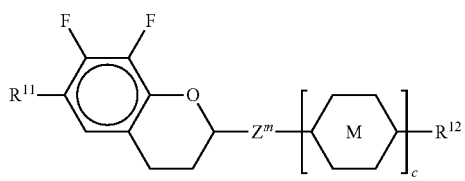

in which
$R^{11}$ and $R^{12}$ each, independently of one another, have the meanings indicated above,
ring M is trans-1,4-cyclohexylene or 1,4-phenylene,
$Z^m$ —$C_2H_4$—, —$CH_2O$—, —$OCH_2$—, —CO—O— or —O—CO—,
c is 0 or 1,
preferably in amounts of 3 to 20% by weight, in particular in amounts of 3 to 15% by weight.

Particularly preferred compounds of the formulae BC, CR and RC are selected from the group consisting of the following sub-formulae:

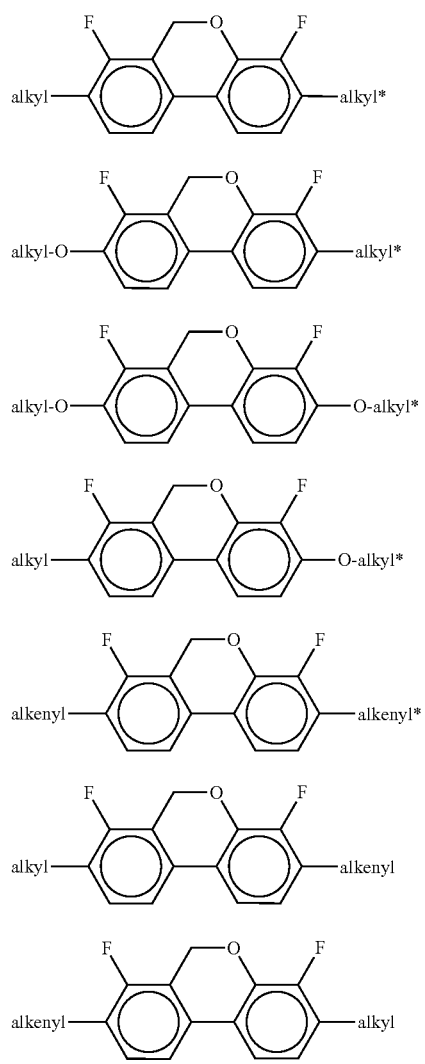
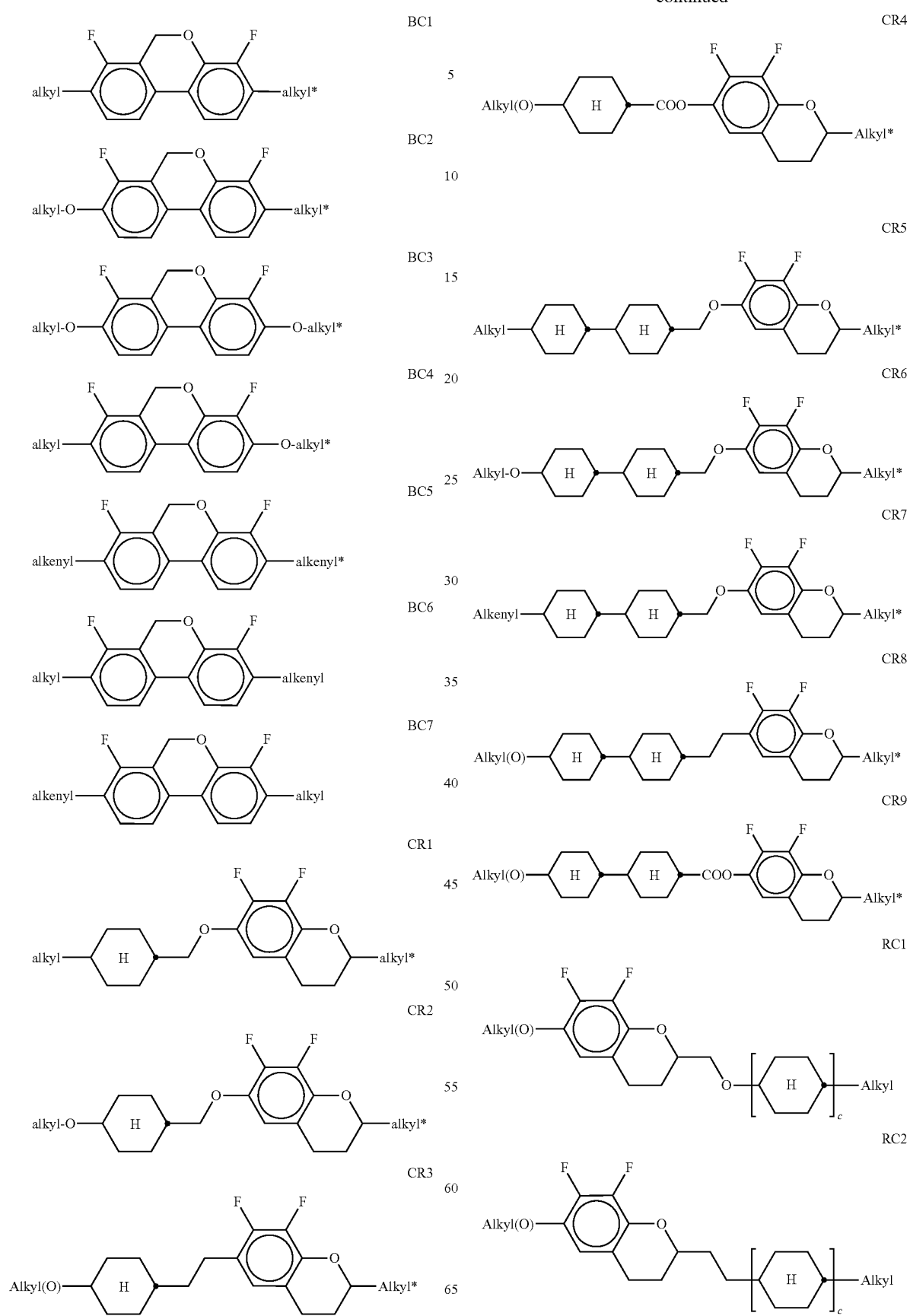

-continued

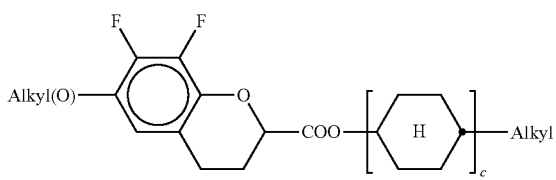
RC3 in which alkyl and alkyl* each, independently of one another, denote a straight-chain alkyl radical having 1-6 C atoms, (O) denotes an oxygen atom or a single bond, c is 1 or 2, and alkenyl and alkenyl* each, independently of one another, denote a straight-chain alkenyl radical having 2-6 C atoms. Alkenyl and alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

Very particular preference is given to mixtures comprising one, two or three compounds of the formula BC-2.

p) LC medium which additionally comprises one or more fluorinated phenanthrenes and/or dibenzofurans of the following formulae:

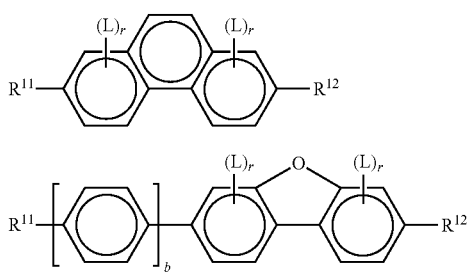
PH

BF in which $R^{11}$ and $R^{12}$ each, independently of one another, have the meanings indicated above, b denotes 0 or 1, L denotes F, and r denotes 1, 2 or 3.

Particularly preferred compounds of the formulae PH and BF are selected from the group consisting of the following sub-formulae:

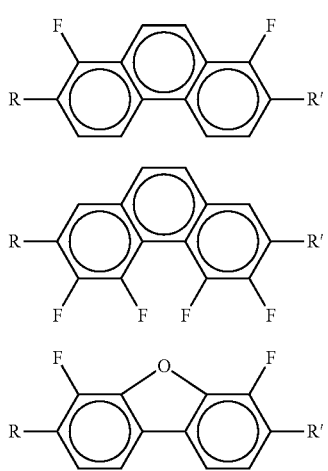
PH1

PH2

BF1

-continued

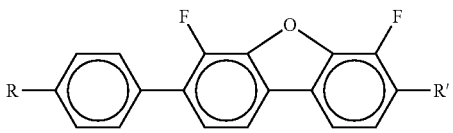
BF2 in which R and R' each, independently of one another, denote a straight-chain alkyl or alkoxy radical having 1-7 C atoms.

q) LC medium which, apart from the polymerisable compounds according to the invention, in particular of the formula I or sub-formulae thereof and the comonomers, comprises no compounds which contain a terminal vinyloxy group ($-O-CH=CH_2$).

r) LC medium which comprises 1 to 5, preferably 1, 2 or 3, polymerisable compounds, preferably selected from polymerisable compounds according to the invention, in particular of the formula I or sub-formulae thereof.

s) LC medium in which the proportion of polymerisable compounds, in particular of the formula I or sub-formulae thereof, in the mixture as a whole is 0.05 to 5%, preferably 0.1 to 1%.

t) LC medium which comprises 1 to 8, preferably 1 to 5, compounds of the formulae CY1, CY2, PY1 and/or PY2. The proportion of these compounds in the mixture as a whole is preferably 5 to 60%, particularly preferably 10 to 35%. The content of these individual compounds is preferably in each case 2 to 20%.

u) LC medium which comprises 1 to 8, preferably 1 to 5, compounds of the formulae CY9, CY10, PY9 and/or PY10. The proportion of these compounds in the mixture as a whole is preferably 5 to 60%, particularly preferably 10 to 35%. The content of these individual compounds is preferably in each case 2 to 20%.

v) LC medium which comprises 1 to 10, preferably 1 to 8, compounds of the formula ZK, in particular compounds of the formulae ZK1, ZK2 and/or ZK6. The proportion of these compounds in the mixture as a whole is preferably 3 to 25%, particularly preferably 5 to 45%. The content of these individual compounds is preferably in each case 2 to 20%.

w) LC medium in which the proportion of compounds of the formulae CY, PY and ZK in the mixture as a whole is greater than 70%, preferably greater than 80%.

x) LC medium in which the LC host mixture contains one or more compounds containing an alkenyl group, preferably selected from the group consisting of formula CY, PY and LY, wherein one or both of $R^1$ and $R^2$ denote straight-chain alkenyl having 2-6 C atoms, formula ZK and DK, wherein one or both of, $R^3$ and $R^4$ denote straight-chain alkenyl having 2-6 C atoms, and formula B2 and B3, very preferably selected from formulae CY15, CY16, CY34, CY32, PY15, PY16, ZK3, ZK4, DK3, DK6, B2 and B3, most preferably selected from formulae ZK3, ZK4, B2 and B3. The concentration of these compounds in the LC host mixture is preferably from 2 to 70%, very preferably from 3 to 55%.

y) PSA-VA display in which the pretilt angle is preferably ≤85°, particularly preferably ≤80°.

In a second preferred embodiment the LC medium contains an LC host mixture based on compounds with positive dielectric anisotropy. Such LC media are especially suitable for use in PSA-OCB-, PSA-TN-, PSA-Posi-VA-, PSA-IPS- oder PSA-FFS-displays.

Particularly preferred is an LC medium of this second preferred embodiment, which contains one or more compounds selected from the group consisting of compounds of formula AA and BB

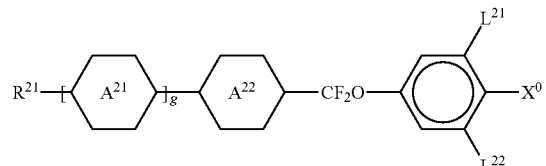

AA

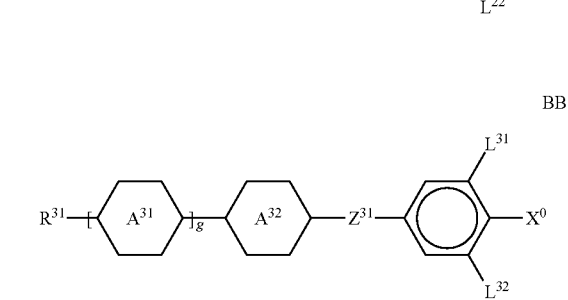

BB and optionally contains, in addition to the compounds of formula AA and/or BB, one or more compounds of formula CC

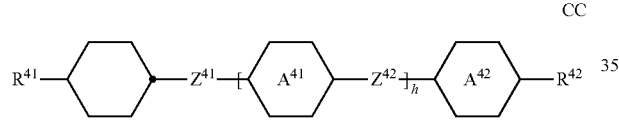

CC in which the individual radicals have the following meanings:

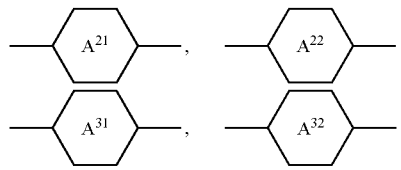

each, independently of one another, and on each occurrence, identically or differently

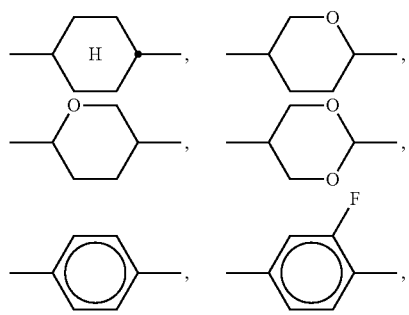

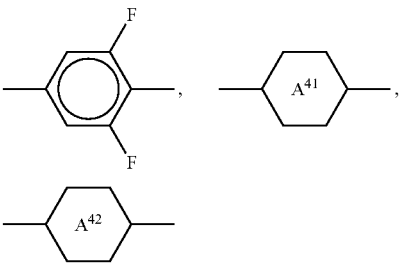

each, independently of one another, and on each occurrence, identically or differently

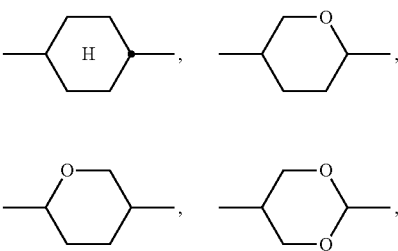

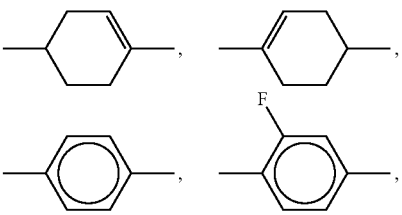

$R^{21}$, $R^{31}$, $R^{41}$, $R^{42}$ each, independently of one another, alkyl, alkoxy, oxaalkyl or fluoroalkyl having 1 to 9 C atoms or alkenyl having 2 to 9 C atoms, $X^0$ F, Cl, halogenated alkyl or alkoxy having 1 to 6 C atoms or halogenated alkenyl or alkenyloxy having 2 to 6 C atoms, $Z^{31}$ —$CH_2CH_2$—, —$CF_2CF_2$—, —COO—, trans-CH=CH—, trans-CF=CF—, —$CH_2O$— or a single bond, preferably —$CH_2CH_2$—, —COO—, trans-CH=CH— or a single bond, particularly preferably —COO—, trans-CH=CH— or a single bond, $Z^{41}$, $Z^{42}$ —$CH_2CH_2$—, —COO—, trans-CH=CH—, trans-CF=CF—, —$CH_2O$—, —$CF_2O$—, —C≡C— or a single bond, preferably a single bond, $L^{21}$, $L^{22}$, $L^{31}$, $L^{32}$ H or F, g 1, 2 or 3, h 0, 1, 2 or 3.

$X^0$ is preferably F, Cl, $CF_3$, $CHF_2$, $OCF_3$, $OCHF_2$, $OCFHCF_3$, $OCFHCHF_2$, $OCFHCHF_2$, $OCF_2CH_3$, $OCF_2CHF_2$, $OCF_2CHF_2$, $OCF_2CF_2CHF_2$, $OCF_2CF_2CHF_2$, $OCFHCF_2CF_3$, $OCFHCF_2CHF_2$, $OCF_2CF_2CF_3$, $OCF_2CF_2CClF_2$, $OCClFCF_2CF_3$ or CH=$CF_2$, very preferably F or $OCF_3$ The compounds of formula AA are preferably selected from the group consisting of the following formulae:

AA1
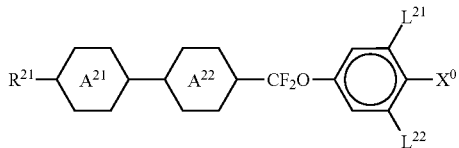

AA2
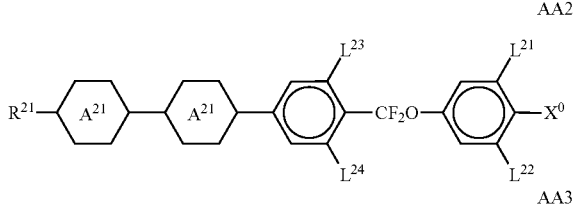

AA3
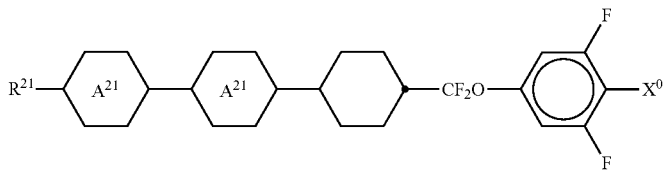

AA4
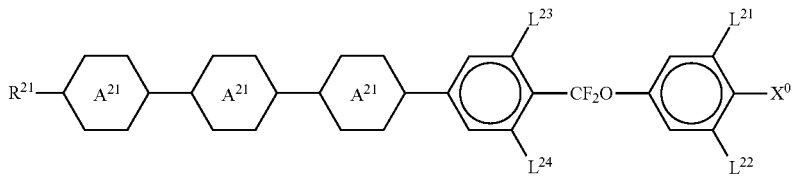

in which $A^{21}$, $R^{21}$, $X^0$, $L^{21}$ and $L^{22}$ have the meanings given in formula AA, $L^{23}$ and $L^{24}$ each, independently of one another, are H or F, and $X^0$ is preferably F. Particularly preferred are compounds of formulae AA1 and AA2.

Particularly preferred compounds of formula AA1 are selected from the group consisting of the following subformulae AA1a
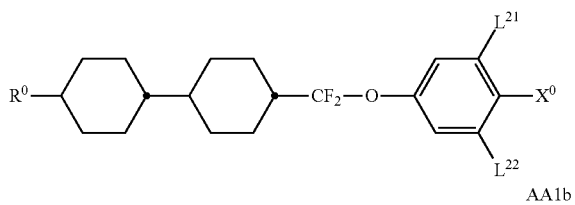

AA1b
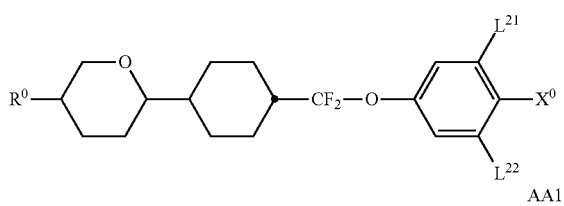

AA1c
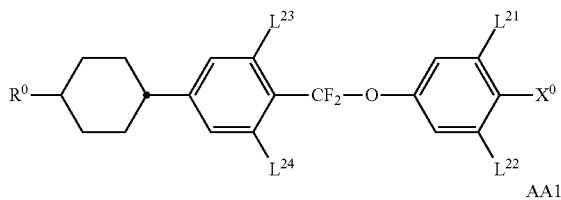

AA1d
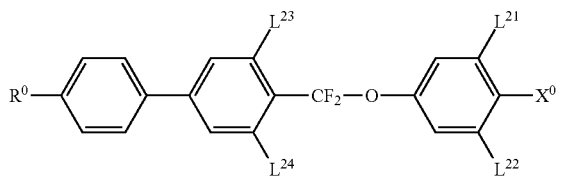

-continued

AA1e
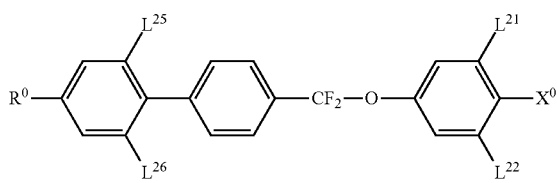

in which $R^0$ has one of the meanings given for $R^{21}$ in formula AA1, $X^0$, $L^{21}$ and $L^{22}$ have the meaning given in formula AA1, $L^{23}$, $L^{24}$, $L^{25}$ and $L^{26}$ are each, independently of one another, H or F, and $X^0$ is preferably F.

Very particularly preferred compounds of formula AA1 are selected from the group consisting of the following subformulae:

AA1a1
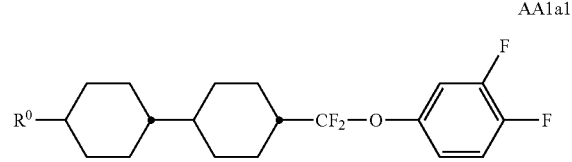

AA1a2
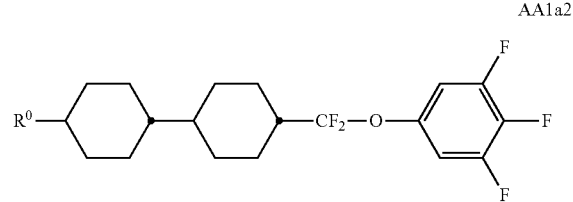

AA1b1

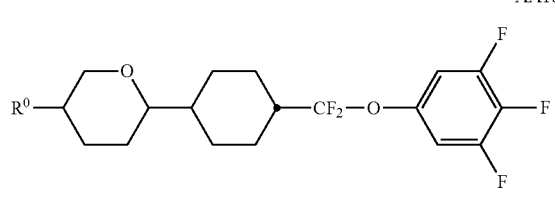

AA2e

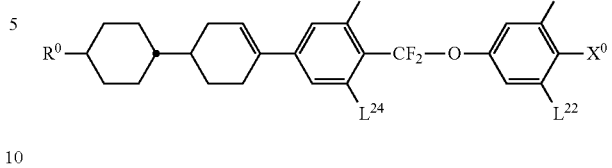

AA1c1

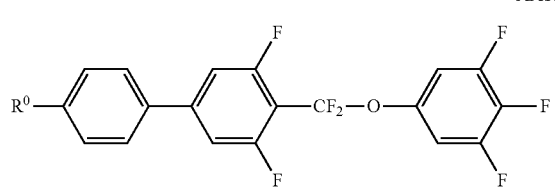

AA2f

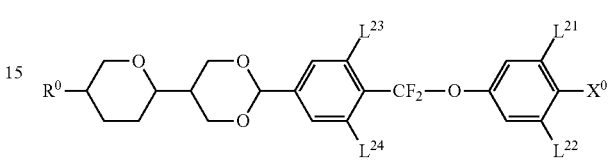

AA1e2

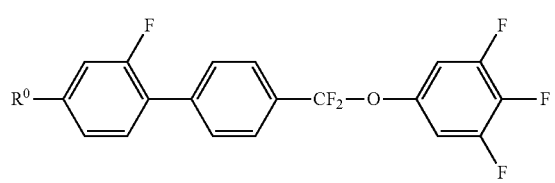

AA2g

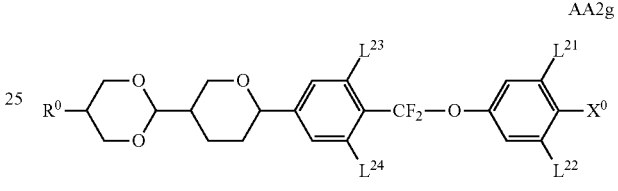

In which $R^0$ has the meaning given for $R^{21}$ in formula AA1.

Very preferred compounds of formula AA2 are selected from the group consisting of the following subformulae AA2h

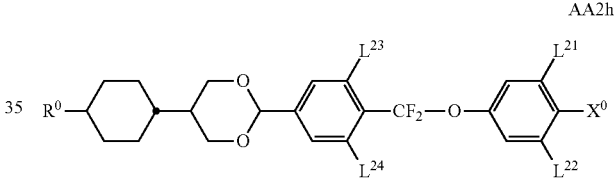

AA2a

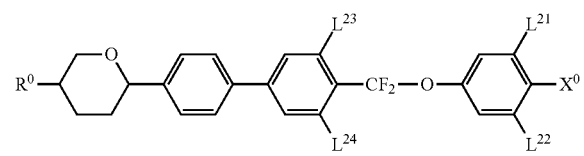

AA2i

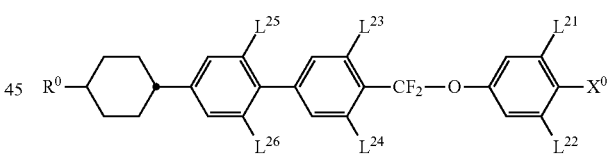

AA2b

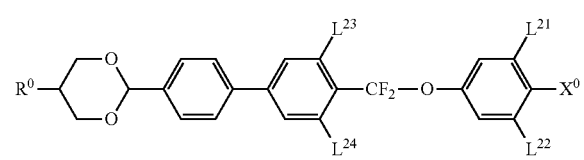

AA2j

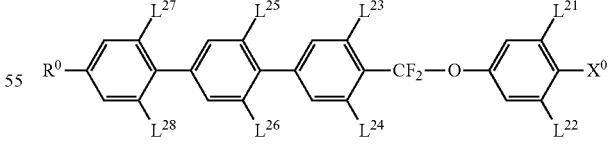

AA2c

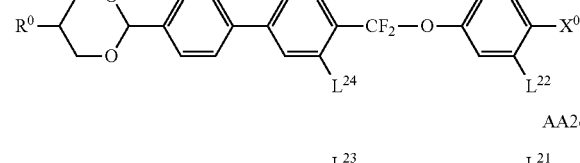

AA2d

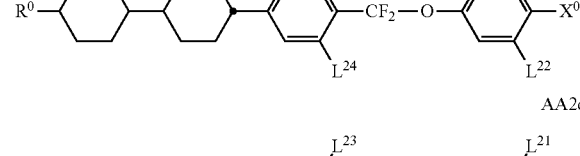

in which $R^0$ has the meaning given for $R^{21}$ in formula AA1, $X^0$, $L^{21}$ and $L^{22}$ have the meaning given in formula AA, $L^{23}$, $L^{24}$, $L^{25}$ and $L^{26}$ each, independently of one another, are H or F, and $X^0$ is preferably F.

Very particularly preferred compounds of formula AA2 are selected from the group consisting of the following subformulae AA2a1
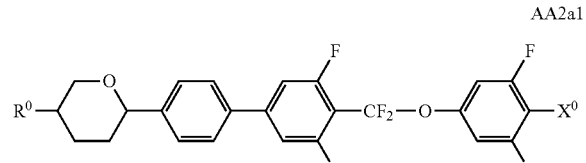

AA2c1
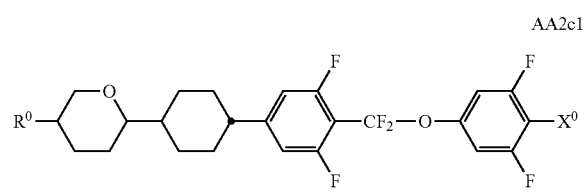

AA2d1
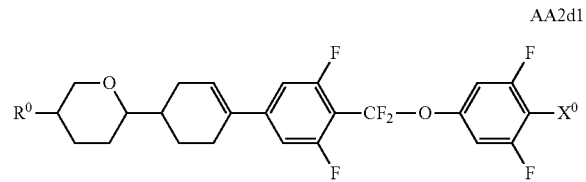

AA2e1
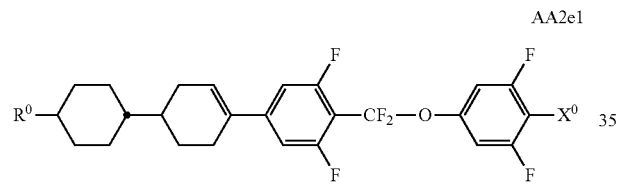

AA2f1
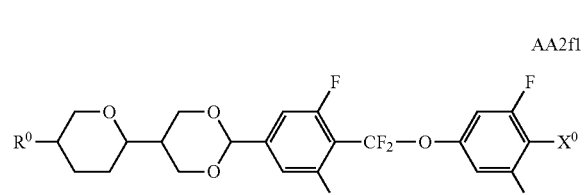

AA2h1
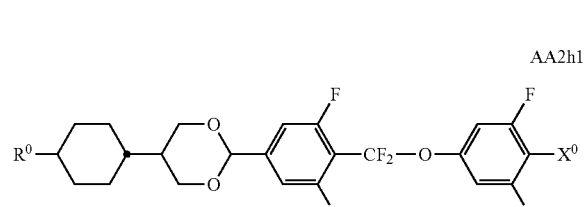

AA2i1
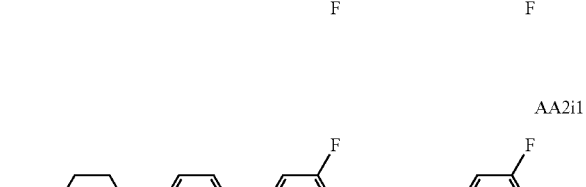

AA2i2
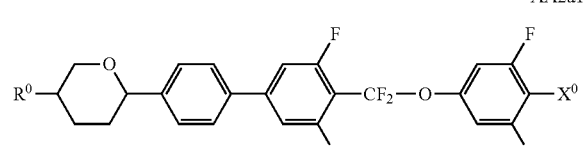

AA2j1
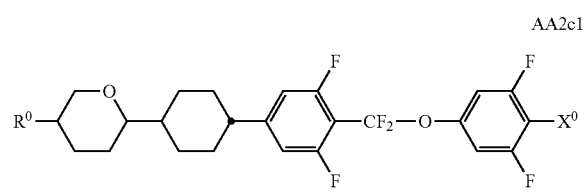

AA2j2
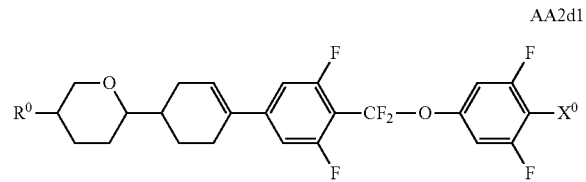

in which $R^0$ has the meaning given for $R^{21}$ in formula AA1.

Particularly preferred compounds of formula AA3 are selected from the group consisting of the following subformulae AA3a
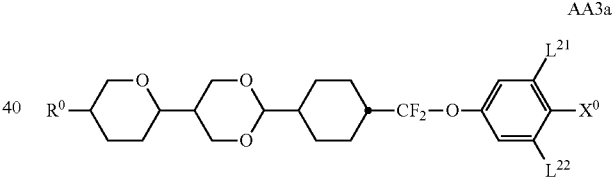

AA3b
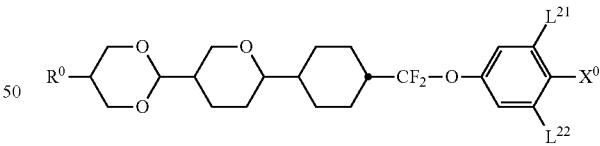

AA3c
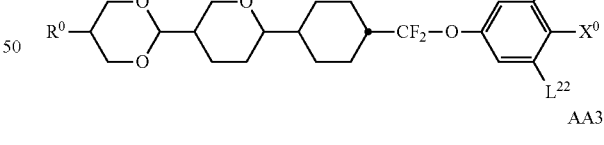

in which $R^0$ has the meaning given for $R^{21}$ in formula AA1, $X^0$, $L^{21}$ and $L^{22}$ have the meaning given in formula AA3, and $X^0$ is preferably F.

Particularly preferred compounds of formula AA4 are selected from the group consisting of the following subformulae

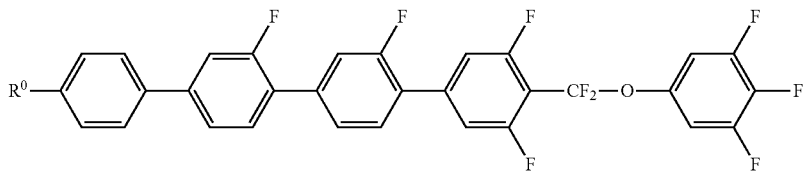
AA4a in which R⁰ has the meaning given for $R^{21}$ in formula AA1.

The compounds of formula BB are preferably selected from the group consisting of the following formulae:

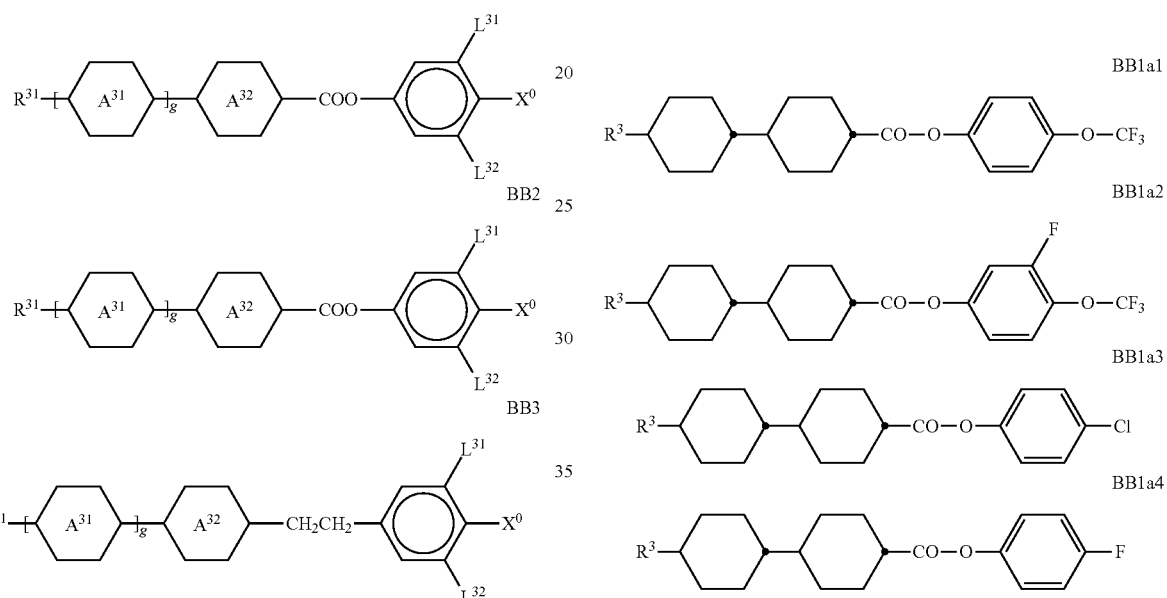

in which $A^{31}$, $A^{32}$, $R^{31}$, $X^0$, $L^{31}$ and $L^{32}$ have the meanings given in formula BB, and $X^0$ is preferably F. Particularly preferred are compounds of formulae BB1 and BB2.

Particularly preferred compounds of formula BB1 are selected from the group consisting of the following subformulae in which $R^3$ has the meaning given for $R^{31}$ in formula BB1, $X^0$, $L^{31}$ and $L^{32}$ have the meaning given in formula BB1, and $X^0$ is preferably F.

Very particularly preferred compounds of formula BB1a are selected from the group consisting of the following subformulae

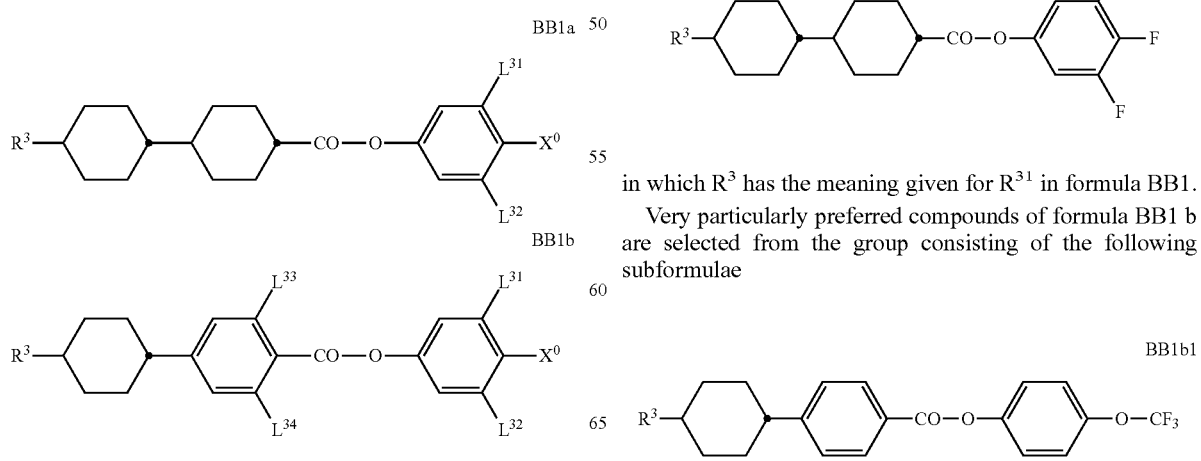

in which $R^3$ has the meaning given for $R^{31}$ in formula BB1.

Very particularly preferred compounds of formula BB1 b are selected from the group consisting of the following subformulae BB1b2
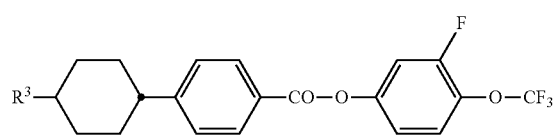

BB1b3
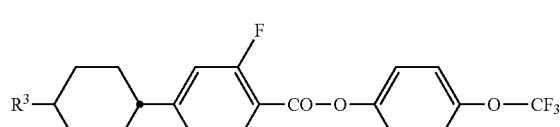

BB1b4
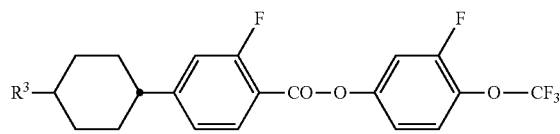

in which R³ has the meaning given for R³¹ in formula BB1.

Particularly preferred compounds of formula BB2 are selected from the group consisting of the following subformulae BB2a
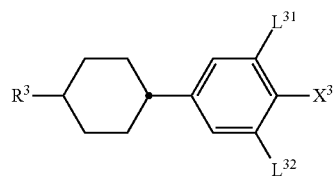

BB2b
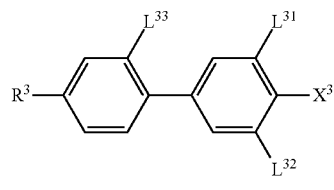

BB2c
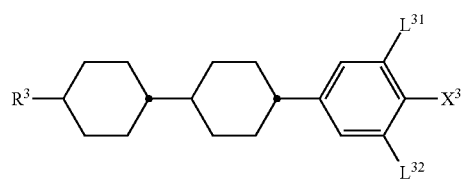

BB2d
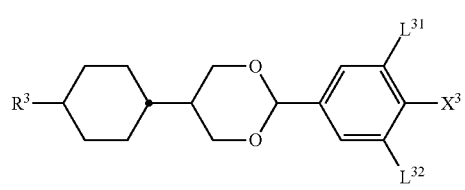

BB2e
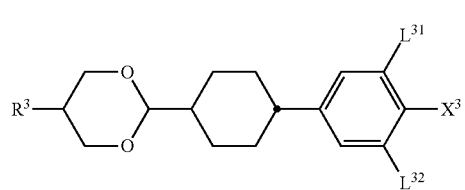

BB2f
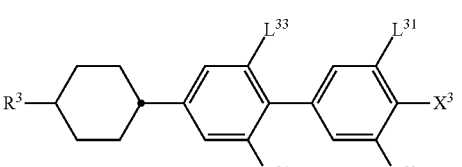

BB2g
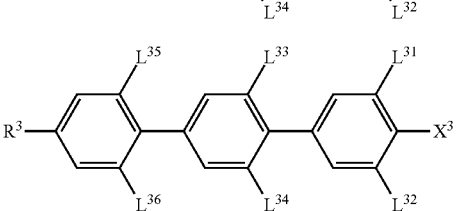

BB2h
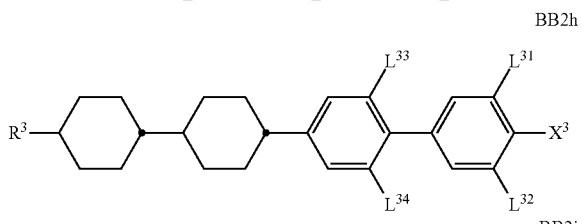

BB2i
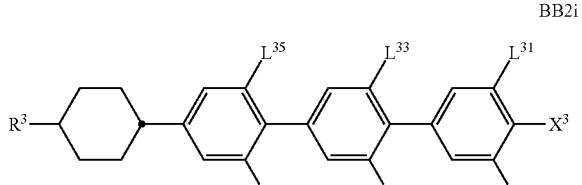

BB2k
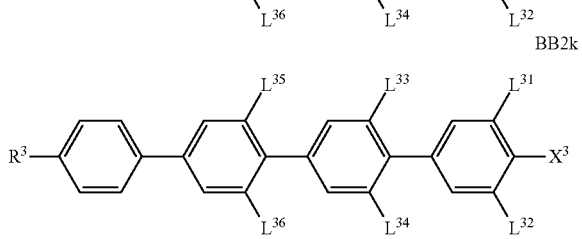

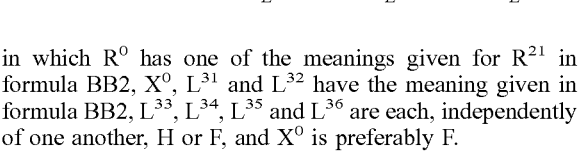

in which $R^0$ has one of the meanings given for $R^{21}$ in formula BB2, $X^0$, $L^{31}$ and $L^{32}$ have the meaning given in formula BB2, $L^{33}$, $L^{34}$, $L^{35}$ and $L^{36}$ are each, independently of one another, H or F, and $X^0$ is preferably F.

Very particularly preferred compounds of formula BB2 are selected from the group consisting of the following subformulae:

BB2a1
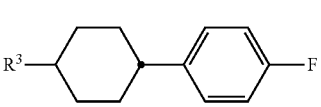

BB2a2

BB2a3
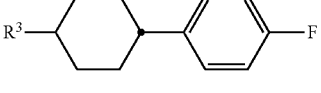

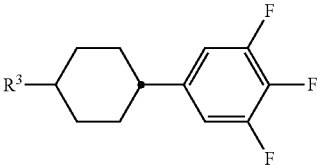

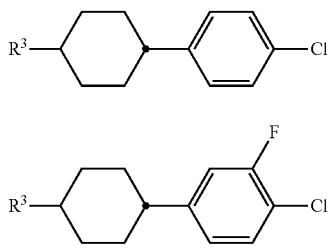
BB2a4

BB2a5 in which R³ has the meaning given for R³¹ in formula BB2.

Very particularly preferred compounds of formula BB2b are selected from the group consisting of the following subformulae

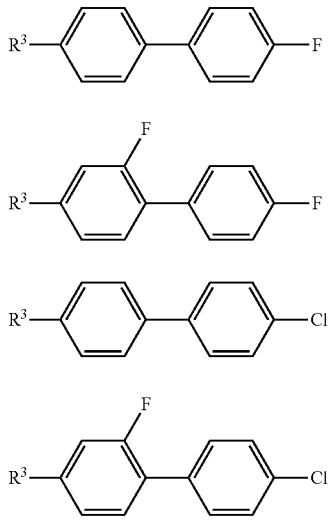
BB2b1

BB2b2

BB2b3

BB2b4 in which R³ has the meaning given for R³¹ in formula BB2.

Very particularly preferred compounds of formula BB2c are selected from the group consisting of the following subformulae

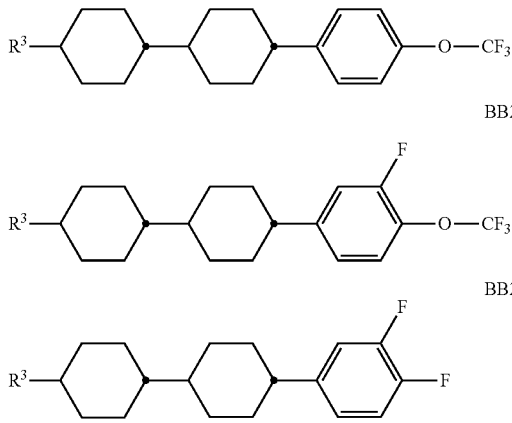
BB2c1

BB2c1

BB2c3

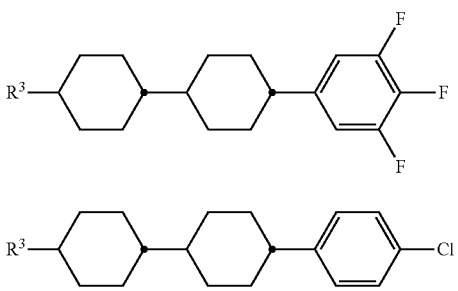
BB2c4

BB2c4 in which R³ has the meaning given for R³¹ in formula BB2.

Very particularly preferred compounds of formula BB2d and BB2e are selected from the group consisting of the following subformulae

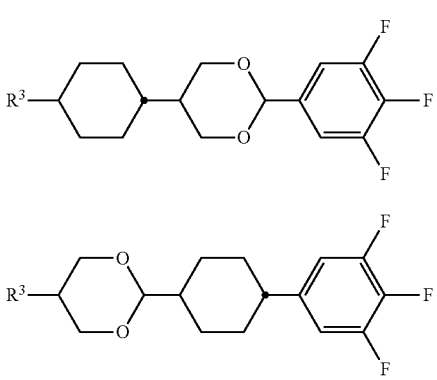
BB2d1

BB2e1 in which R³ has the meaning given for R³¹ in formula BB2.

Very particularly preferred compounds of formula BB2f are selected from the group consisting of the following subformulae

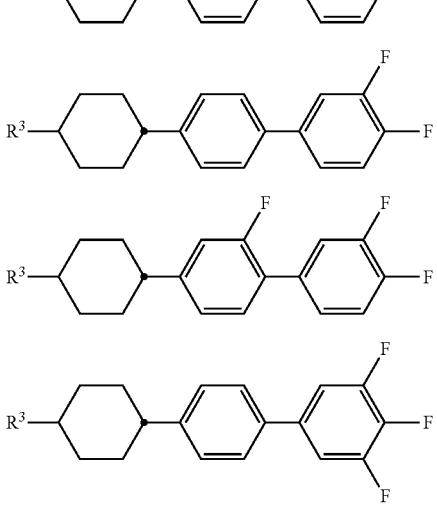
BB2f1

BB2f2

BB2f3

BB2f4

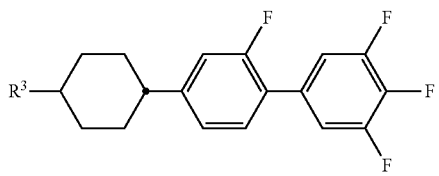
BB2f4 in which R³ has the meaning given for R³¹ in formula BB2.

Very particularly preferred compounds of formula BB2g are selected from the group consisting of the following subformulae

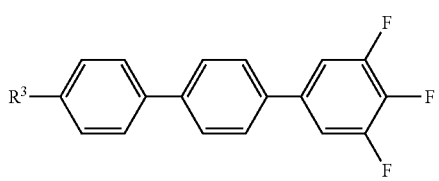
BB2g1

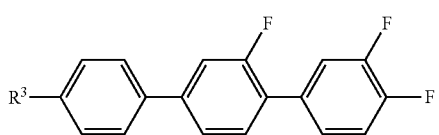
BB2g2

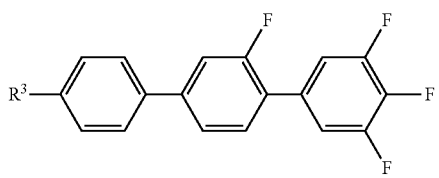
BB2g3

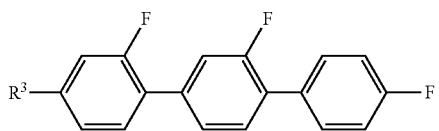
BB2g4

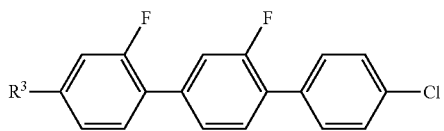
BB2g5 in which R³ has the meaning given for R³¹ in formula BB2.

Very particularly preferred compounds of formula BB2h are selected from the group consisting of the following subformulae

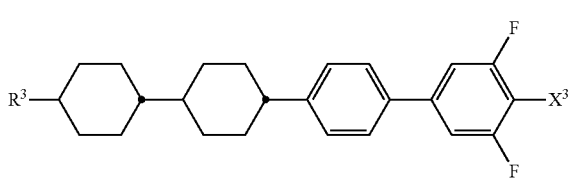
BB2h1

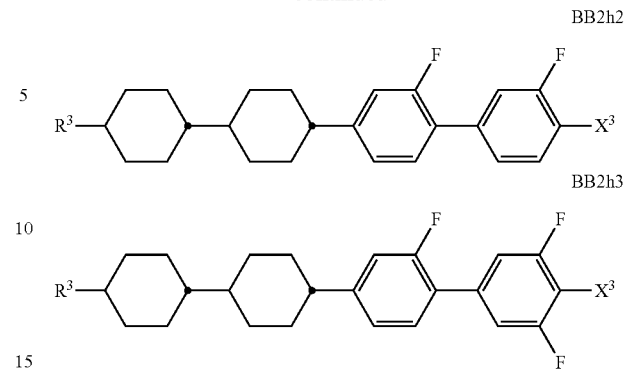
BB2h2

BB2h3 in which R³ has the meaning given for R³¹ in formula BB2.

Very particularly preferred compounds of formula BB2i are selected from the group consisting of the following subformulae

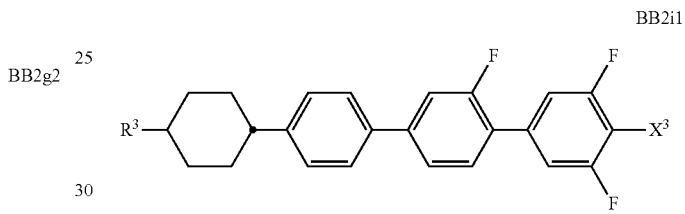
BB2i1

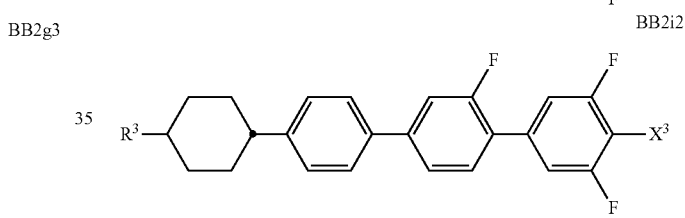
BB2i2 in which R³ has the meaning given for R³¹ in formula BB2.

Very particularly preferred compounds of formula BB2k are selected from the group consisting of the following subformulae

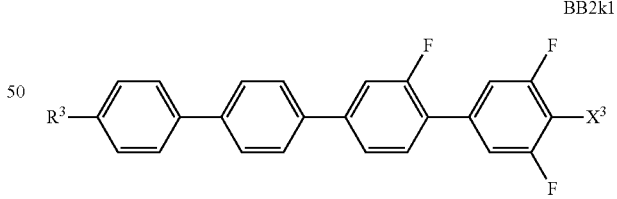
BB2k1

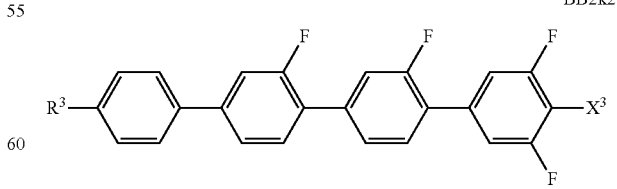
BB2k2 in which R³ has the meaning given for R³¹ in formula BB2.

Alternatively to, or in addition to, the compounds of formula BB1 and/or BB2 the LC media may also comprise one or more compounds of formula BB3 as defined above.

Particularly preferred compounds of formula BB3 are selected from the group consisting of the following subformulae BB3a

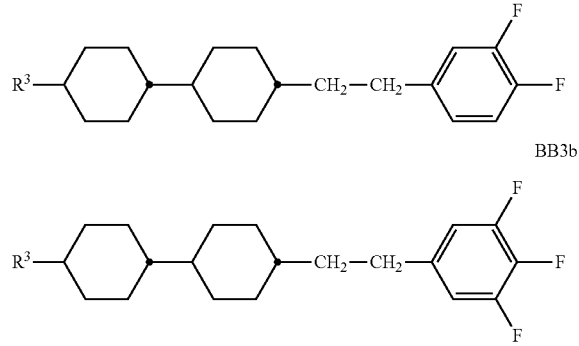

BB3b in which R³ has the meaning given for R³¹ in formula BB3.

Preferably the LC media according to this second preferred embodiment comprise, in addition to the compounds of formula AA and/or BB, one or more dielectrically neutral compounds having a dielectric anisotropy in the range from −1.5 to +3, preferably selected from the group of compounds of formula CC as defined above.

Particularly preferred compounds of formula CC are selected from the group consisting of the following subformulae CC1
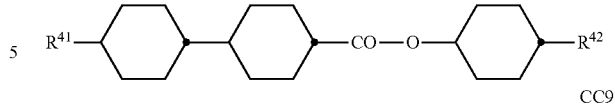

CC2

CC3
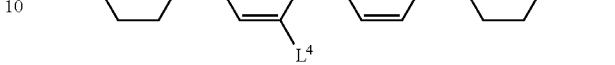

CC4
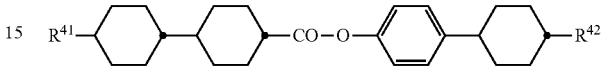

CC5
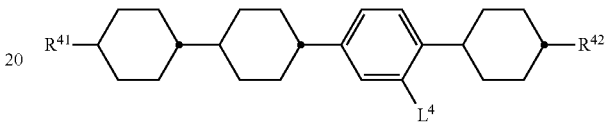

CC6
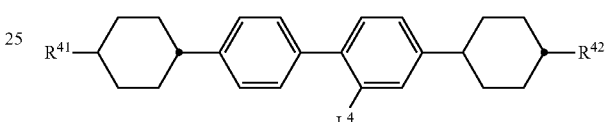

CC7
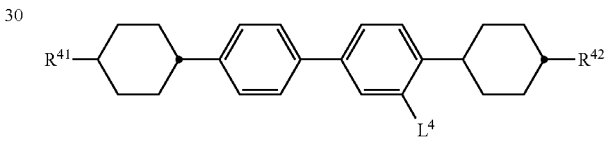

CC8

CC9
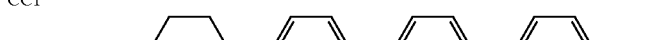

CC10

CC11

CC12
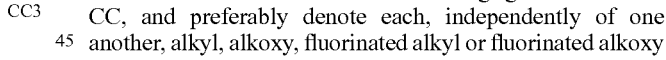

CC13
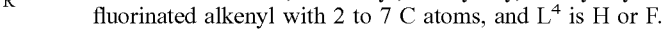

CC14
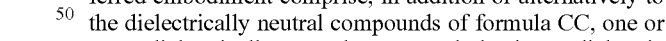

In which $R^{41}$ and $R^{42}$ have the meanings given in formula CC, and preferably denote each, independently of one another, alkyl, alkoxy, fluorinated alkyl or fluorinated alkoxy with 1 to 7 C atoms, or alkenyl, alkenyloxy, alkoxyalkyl or fluorinated alkenyl with 2 to 7 C atoms, and $L^4$ is H or F.

Preferably the LC media according to this second preferred embodiment comprise, in addition or alternatively to the dielectrically neutral compounds of formula CC, one or more dielectrically neutral compounds having a dielectric anisotropy in the range from −1.5 to +3, selected from the group of compounds of formula DD.

DD
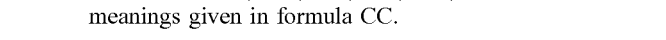

In which $A^{41}$, $A^{42}$, $Z^{41}$, $Z^{42}$, $R^{41}$, $R^{42}$ and h have the meanings given in formula CC.

Particularly preferred compounds of formula DD are selected from the group consisting of the following subformulae

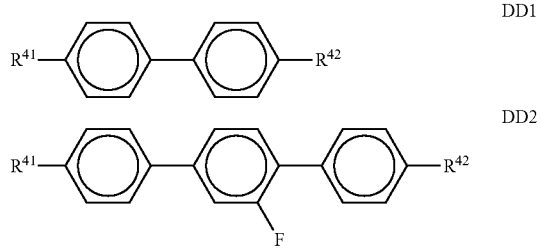

in which $R^{41}$ and $R^{42}$ have the meanings given in formula DD and $R^{41}$ preferably denotes alkyl bedeutet, and in formula DD1 $R^{42}$ preferably denotes alkenyl, particularly preferably vorzugsweise $-(CH_2)_2-CH=CH-CH_3$, and in formula DD2 $R^{42}$ preferably denotes alkyl, $-(CH_2)_2-CH=CH_2$ or $-(CH_2)_2-CH=CH-CH_3$.

The compounds of formula AA and BB are preferably used in the LC medium according to the invention in a concentration from 2% to 60%, more preferably from 3% to 35%, and very particularly preferably from 4% to 30% in the mixture as a whole.

The compounds of formula CC and DD are preferably used in the LC medium according to the invention in a concentration from 2% to 70%, more preferably from 5% to 65%, even more preferably from 10% to 60%, and very particularly preferably from 10%, preferably 15%, to 55% in the mixture as a whole.

The combination of compounds of the preferred embodiments a)-y) mentioned above with the polymerised compounds described above causes low threshold voltages, low rotational viscosities and very good low-temperature stabilities in the LC media according to the invention at the same time as constantly high clearing points and high HR values, and allows the rapid establishment of a particularly low pretilt angle in PSA displays. In particular, the LC media exhibit significantly shortened response times, in particular also the grey-shade response times, in PSA displays compared with the media from the prior art.

The liquid-crystal mixture preferably has a nematic phase range of at least 80 K, particularly preferably at least 100 K, and a rotational viscosity of not greater than 250 mPa·s, preferably not greater than 200 mPa·s, at 20° C.

In the VA-type displays according to the invention, the molecules in the layer of the LC medium in the switched-off state are aligned perpendicular to the electrode surfaces (homeotropically) or have a a tilted homeotropic alignment. On application of an electrical voltage to the electrodes, a realignment of the LC molecules takes place with the longitudinal molecular axes parallel to the electrode surfaces.

LC media according to the invention based on compounds with negative dielectric anisotropy according to the first preferred embodiment, in particular for use in displays of the PSA-VA type, have a negative dielectric anisotropy Δε, preferably from −0.5 to −10, in particular from −2.5 to −7.5, at 20° C. and 1 kHz.

The birefringence Δn in LC media according to the invention for use in displays of the PSA-VA type is preferably below 0.16, particularly preferably from 0.06 to 0.14, very particularly preferably from 0.07 to 0.12.

In the OCB-type displays according to the invention, the molecules in the layer of the LC medium have a "bend" alignment. On application of an electrical voltage, a realignment of the LC molecules takes place with the longitudinal molecular axes perpendicular to the electrode surfaces.

LC media according to the invention for use in displays of the PSA-OCB type are preferably those based on compounds with positive dielectric anisotropy according to the second preferred embodiment, and preferably have a positive dielectric anisotropy Δε from +4 to +17 at 20° C. and 1 kHz. The birefringence Δn in LC media according to the invention for use in displays of the PSA-OCB type is preferably from 0.14 to 0.22, particularly preferably from 0.16 to 0.22.

LC media according to the invention, based on compounds with positive dielectric anisotropy according to the second preferred embodiment, for use in displays of the PSA-TN-, PSA-posi-VA-, PSA-IPS- oder PSA-FFS-type, preferably have a positive dielectric anisotropy Δε from +2 to +30, particularly preferably from +3 to +20, at 20° C. and 1 kHz.

The birefringence Δn in LC media according to the invention for use in displays of the PSA-TN-, PSA-posi-VA-, PSA-IPS- oder PSA-FFS-type is preferably from 0.07 to 0.15, particularly preferably from 0.08 to 0.13.

The LC media according to the invention may also comprise further additives which are known to the person skilled in the art and are described in the literature, such as, for example, polymerisation initiators, inhibitors, stabilisers, surface-active substances or chiral dopants. These may be polymerisable or non-polymerisable. Polymerisable additives are accordingly ascribed to the polymerisable component or component A). Non-polymerisable additives are accordingly ascribed to the non-polymerisable component or component B).

In a preferred embodiment the LC media contain one or more chiral dopants, preferably in a concentration from 0.01 to 1%, very preferably from 0.05 to 0.5%. The chiral dopants are preferably selected from the group consisting of compounds from Table B below, very preferably from the group consisting of R- or S-1011, R- or S-2011, R- or S-3011, R- or S4011, and R- or S-5011.

In another preferred embodiment the LC media contain a racemate of one or more chiral dopants, which are preferably selected from the chiral dopants mentioned in the previous paragraph.

Furthermore, it is possible to add to the LC media, for example, 0 to 15% by weight of pleochroic dyes, furthermore nanoparticles, conductive salts, preferably ethyldimethyldodecylammonium 4-hexoxybenzoate, tetrabutylammonium tetraphenylborate or complex salts of crown ethers (cf., for example, Haller et al., Mol. Cryst. Liq. Cryst. 24, 249-258 (1973)), for improving the conductivity, or substances for modifying the dielectric anisotropy, the viscosity and/or the alignment of the nematic phases. Substances of this type are described, for example, in DE-A 22 09 127, 22 40 864, 23 21 632, 23 38 281, 24 50 088, 26 37 430 and 28 53 728.

The individual components of the preferred embodiments a)-z) of the LC media according to the invention are either known or methods for the preparation thereof can readily be derived from the prior art by the person skilled in the relevant art, since they are based on standard methods described in the literature. Corresponding compounds of the formula CY are described, for example, in EP-A-0 364 538. Corresponding compounds of the formula ZK are described, for example, in DE-A-26 36 684 and DE-A-33 21 373.

The LC media which can be used in accordance with the invention are prepared in a manner conventional per se, for example by mixing one or more of the above-mentioned compounds with one or more polymerisable compounds as defined above, and optionally with further liquid-crystalline compounds and/or additives. In general, the desired amount of the components used in lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing. The invention furthermore relates to the process for the preparation of the LC media according to the invention.

It goes without saying to the person skilled in the art that the LC media according to the invention may also comprise compounds in which, for example, H, N, O, Cl, F have been replaced by the corresponding isotopes.

The structure of the LC displays according to the invention corresponds to the usual geometry for PSA displays, as described in the prior art cited at the outset. Geometries without protrusions are preferred, in particular those in which, in addition, the electrode on the colour filter side is unstructured and only the electrode on the TFT side has slots. Particularly suitable and preferred electrode structures for PSA-VA displays are described, for example, in US 2006/0066793 A1.

The following examples explain the present invention without restricting it. However, they show the person skilled in the art preferred mixture concepts with compounds preferably to be employed and the respective concentrations thereof and combinations thereof with one another. In addition, the examples illustrate which properties and property combinations are accessible.

The following abbreviations are used:

(n, m, z: in each case, independently of one another, 1, 2, 3, 4, 5 or 6)

TABLE A

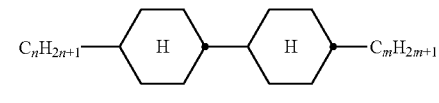

CCH-nm

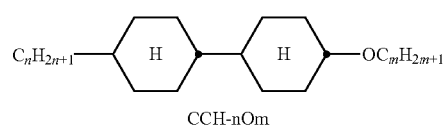

CCH-nOm

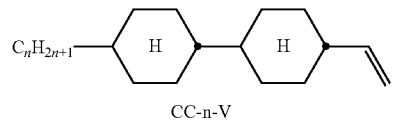

CC-n-V

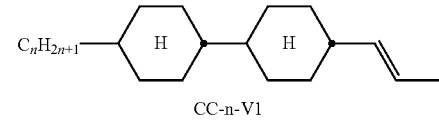

CC-n-V1

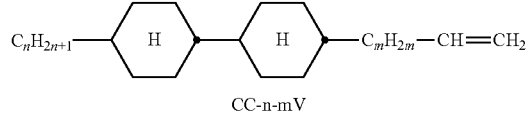

CC-n-mV

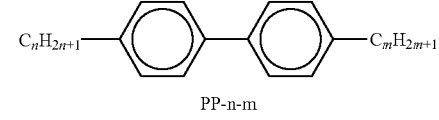

PP-n-m

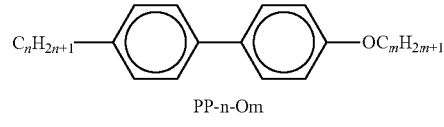

PP-n-Om

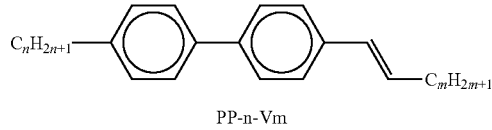

PP-n-Vm

TABLE A-continued
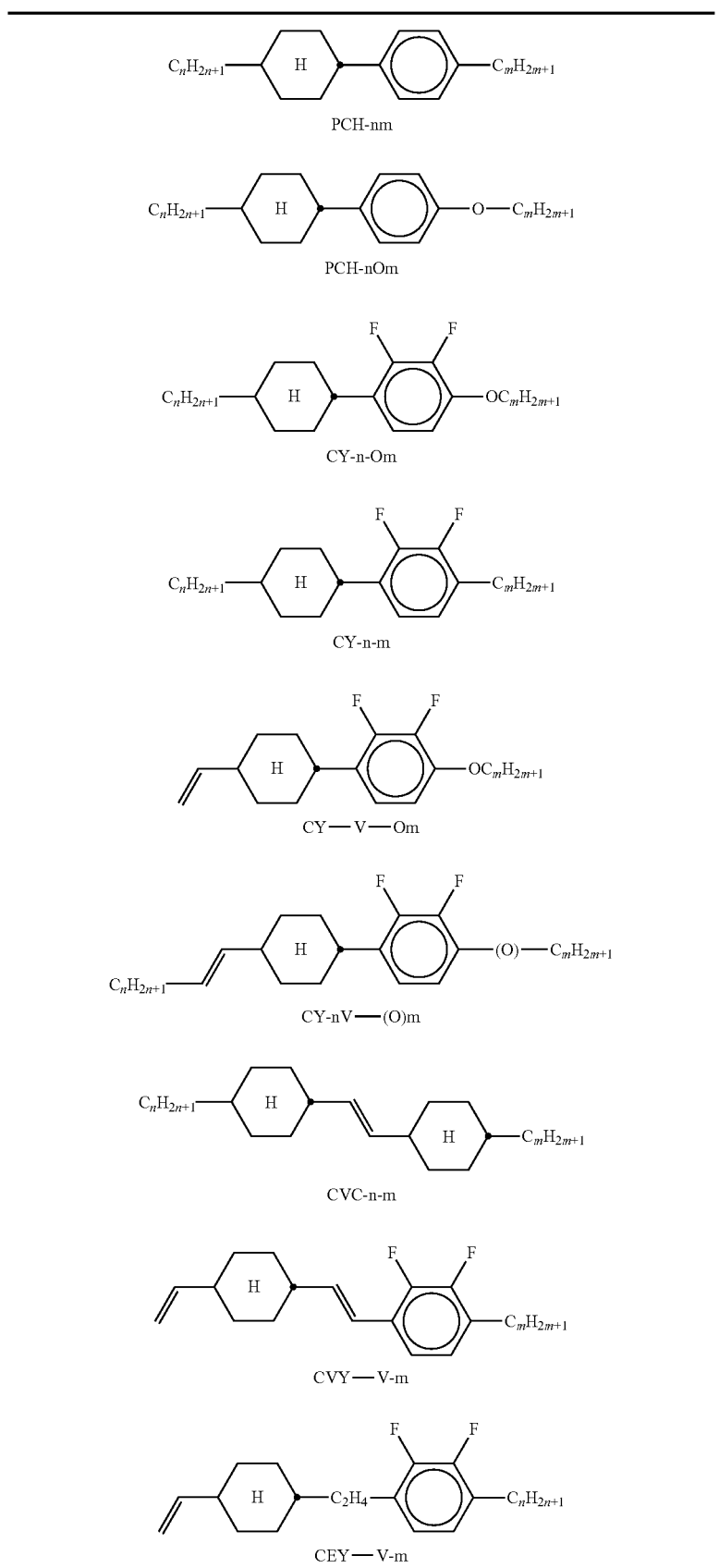

TABLE A-continued
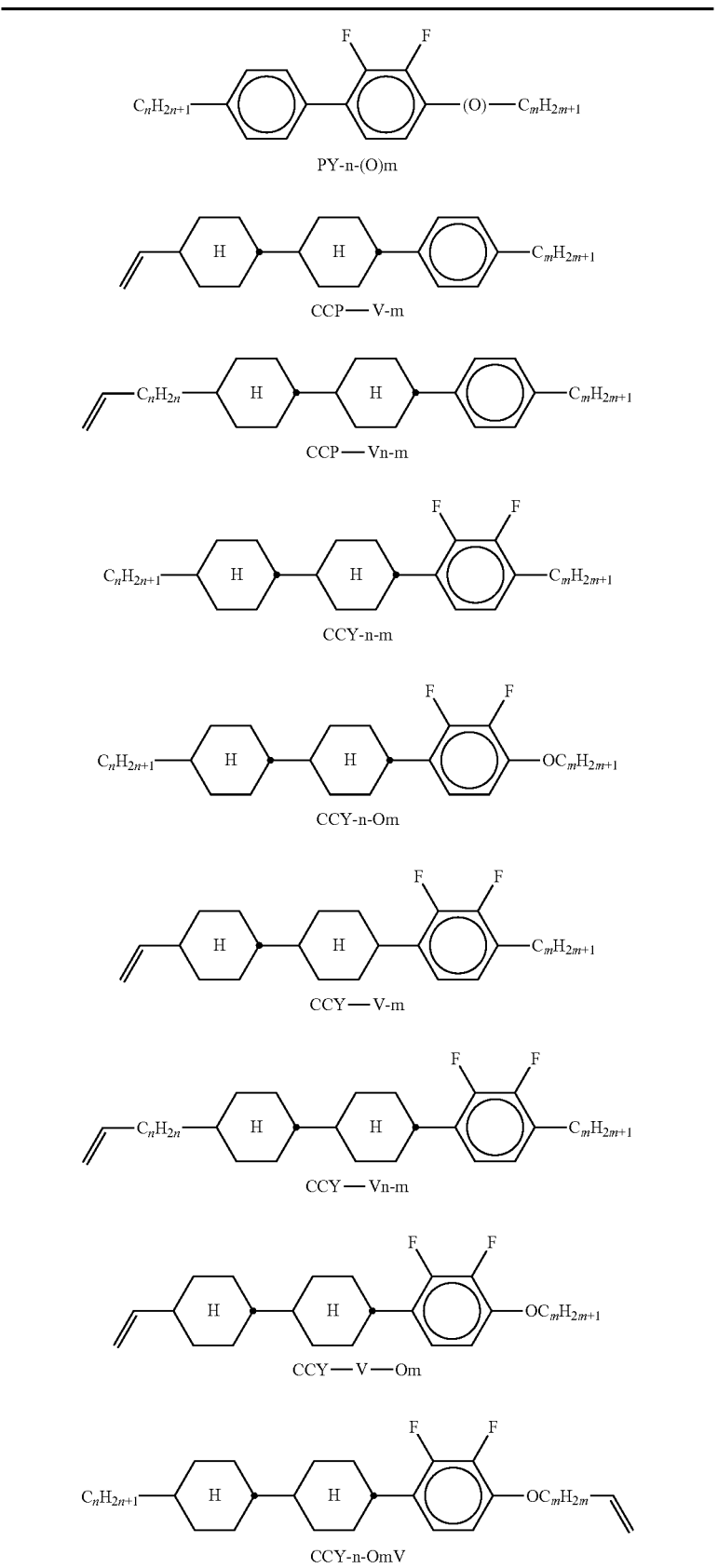

TABLE A-continued
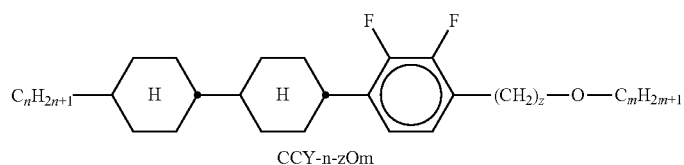
CCY-n-zOm
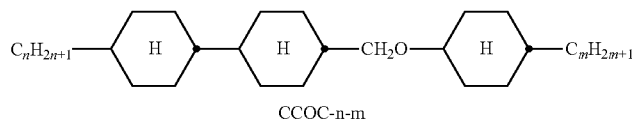
CCOC-n-m
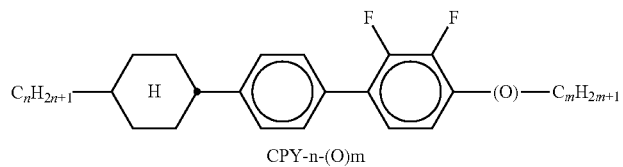
CPY-n-(O)m
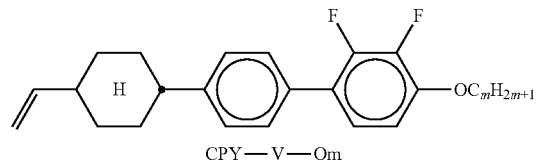
CPY—V—Om
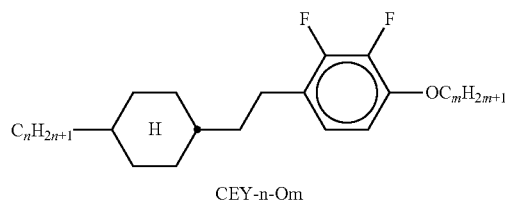
CEY-n-Om
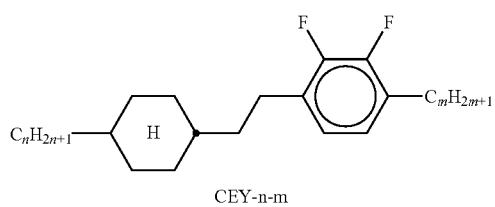
CEY-n-m
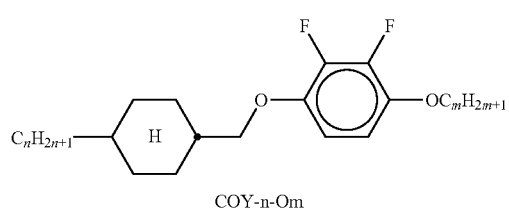
COY-n-Om
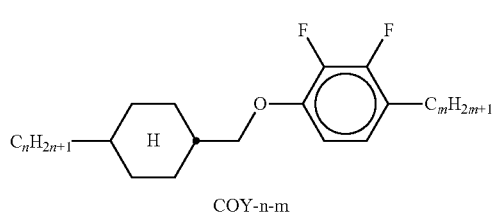
COY-n-m TABLE A-continued
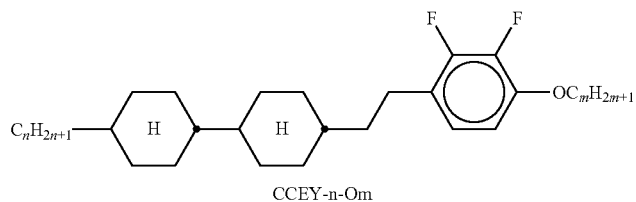
CCEY-n-Om
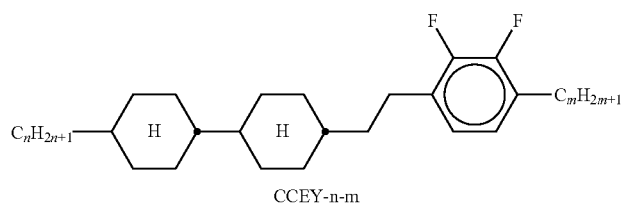
CCEY-n-m
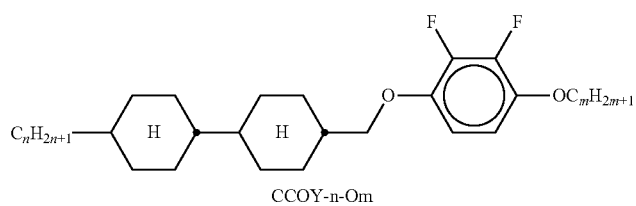
CCOY-n-Om
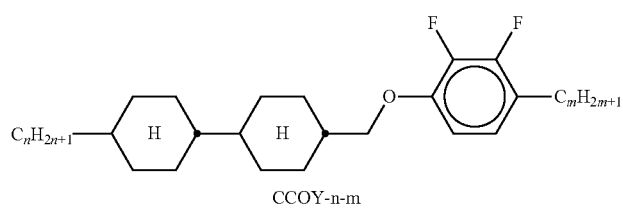
CCOY-n-m
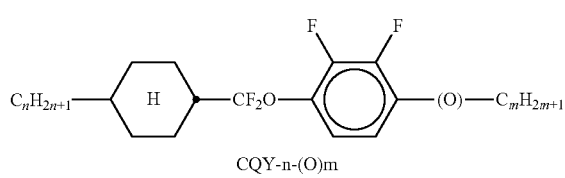
CQY-n-(O)m
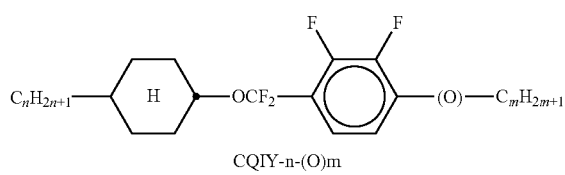
CQIY-n-(O)m
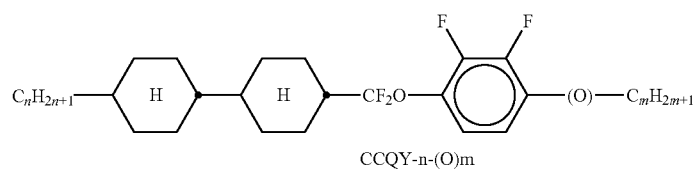
CCQY-n-(O)m
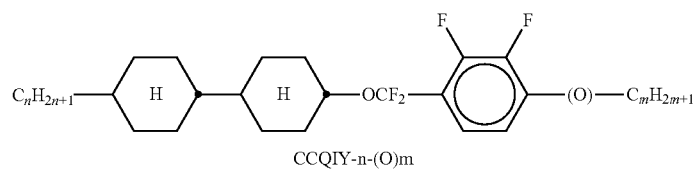
CCQIY-n-(O)m TABLE A-continued
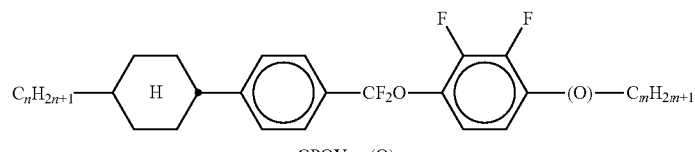
CPQY-n-(O)m
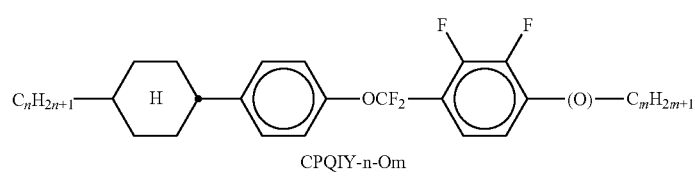
CPQIY-n-Om
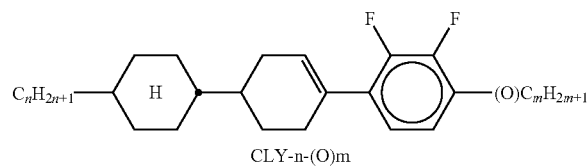
CLY-n-(O)m
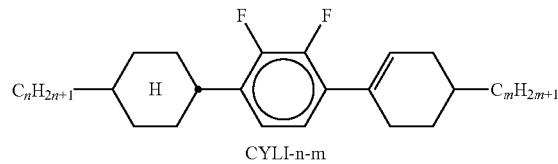
CYLI-n-m
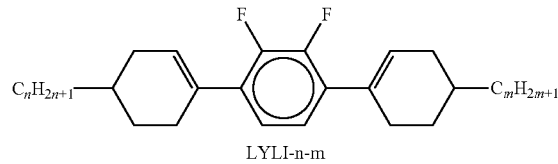
LYLI-n-m
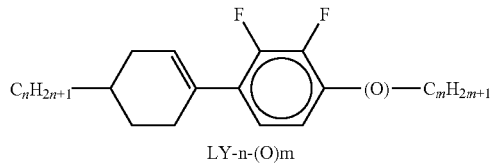
LY-n-(O)m
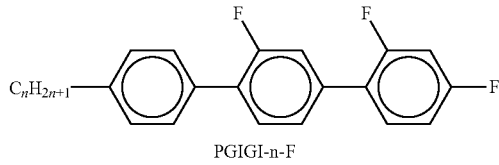
PGIGI-n-F
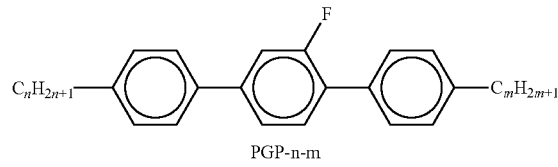
PGP-n-m
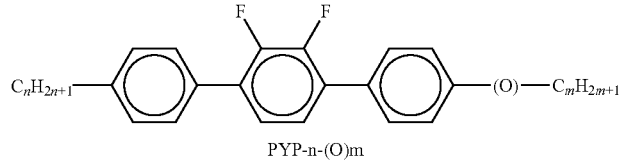
PYP-n-(O)m TABLE A-continued
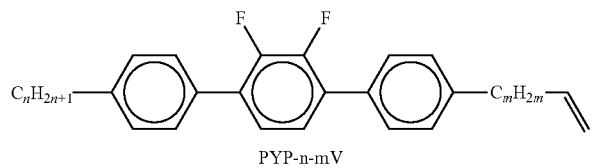
PYP-n-mV
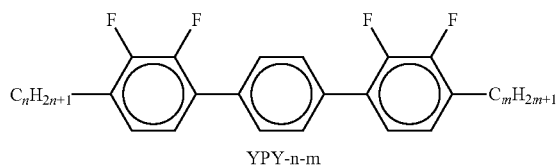
YPY-n-m
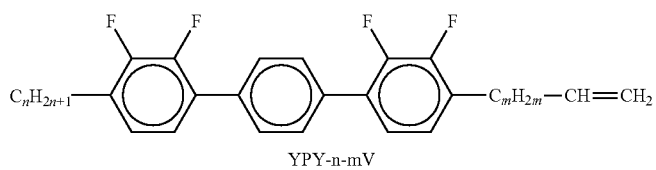
YPY-n-mV
BCH-nm
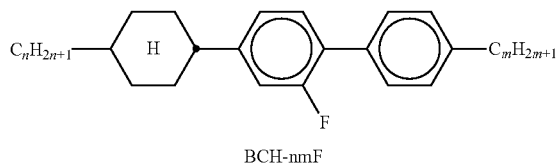
BCH-nmF
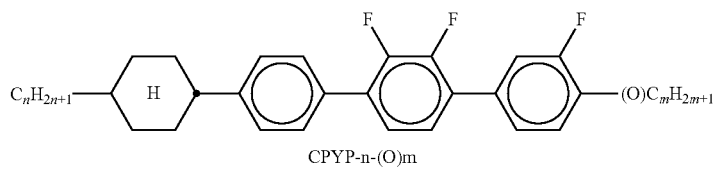
CPYP-n-(O)m
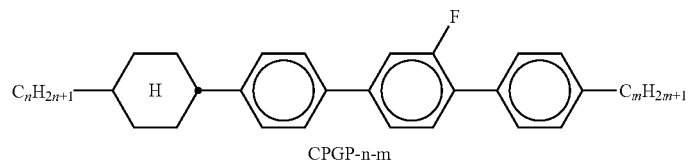
CPGP-n-m
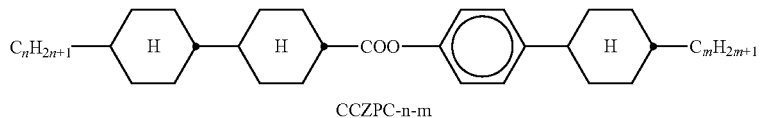
CCZPC-n-m
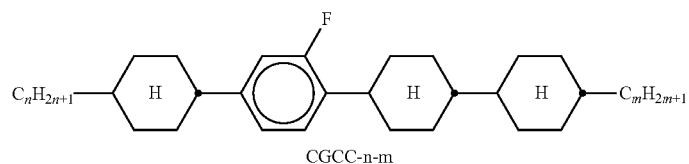
CGCC-n-m TABLE A-continued
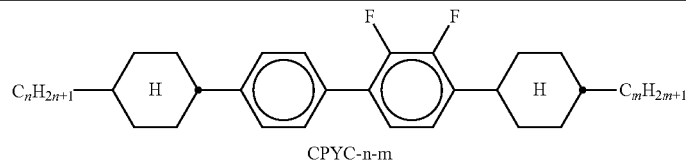
CPYC-n-m
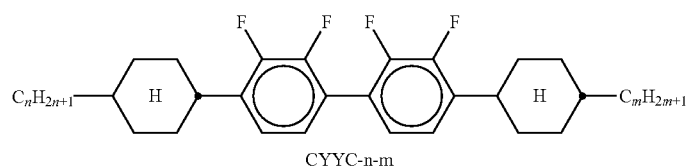
CYYC-n-m
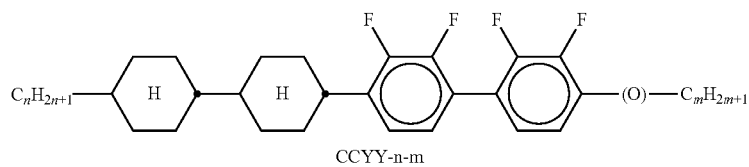
CCYY-n-m
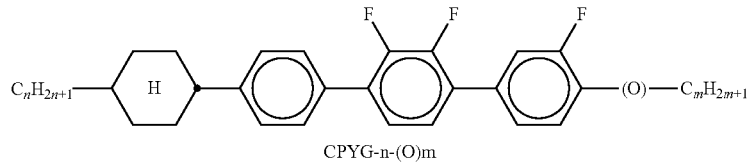
CPYG-n-(O)m
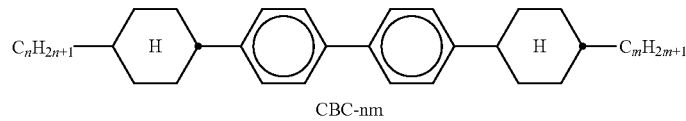
CBC-nm
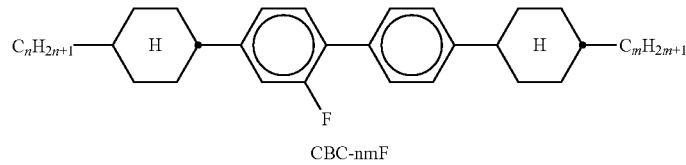
CBC-nmF
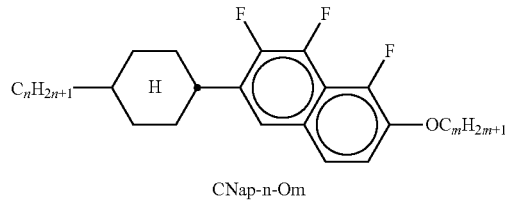
CNap-n-Om
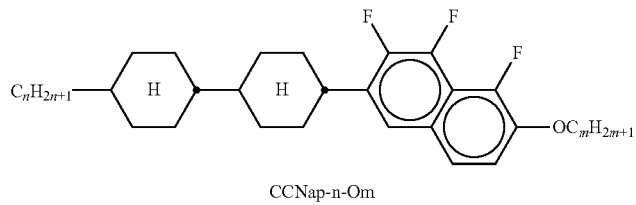
CCNap-n-Om
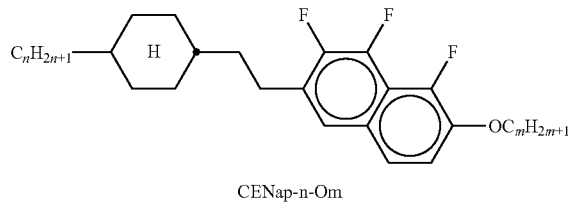
CENap-n-Om TABLE A-continued
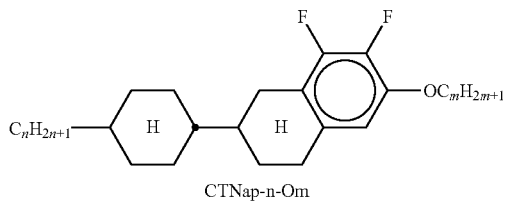
CTNap-n-Om
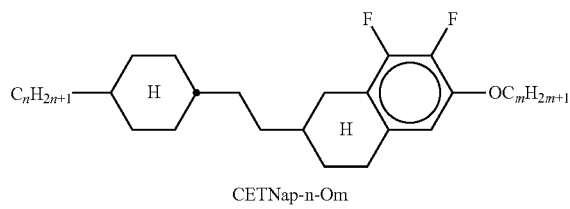
CETNap-n-Om
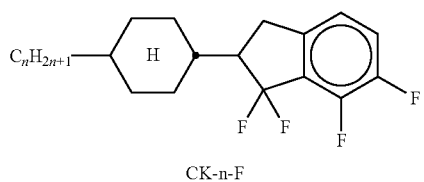
CK-n-F
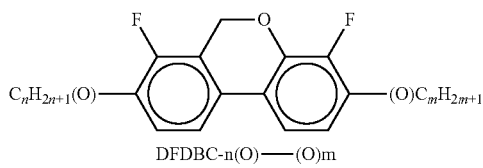
DFDBC-n(O)—(O)m
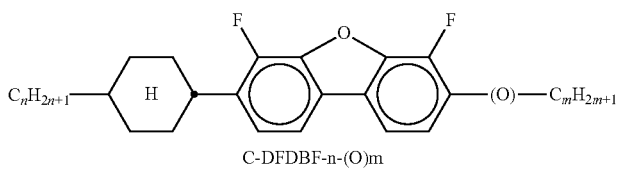
C-DFDBF-n-(O)m
In a preferred embodiment of the present invention, the LC media according to the invention comprise one or more compounds selected from the group consisting of compounds from Table A.
TABLE B
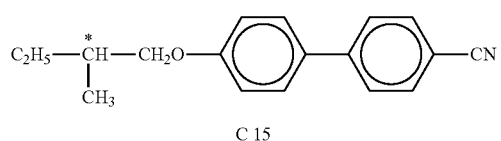
C 15
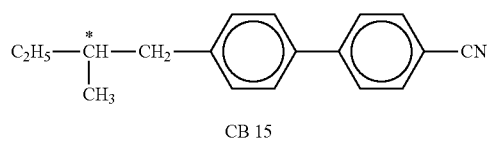
CB 15

TABLE B-continued
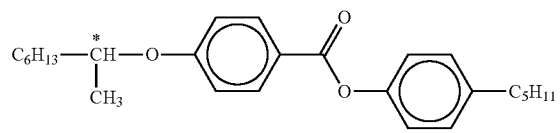
CM 21
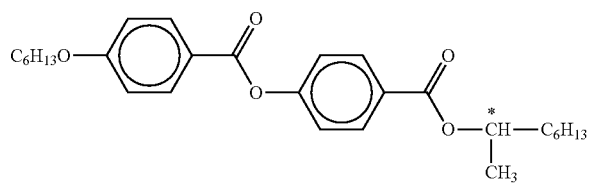
R/S-811
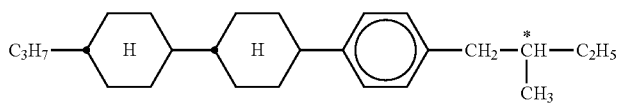
CM 44
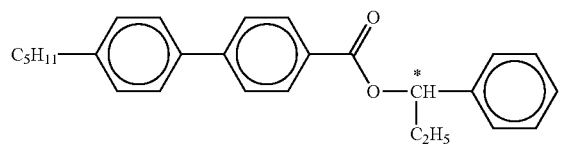
CM 45
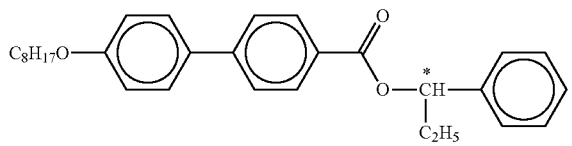
CM 47
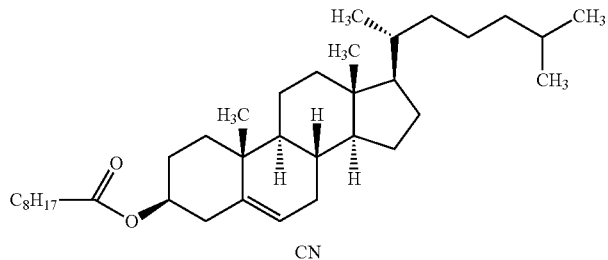
CN
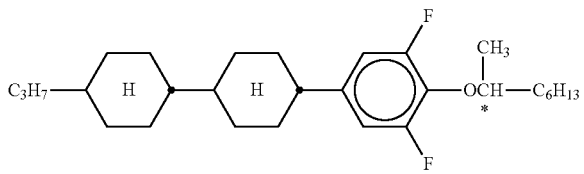
R/S-2011

TABLE B-continued

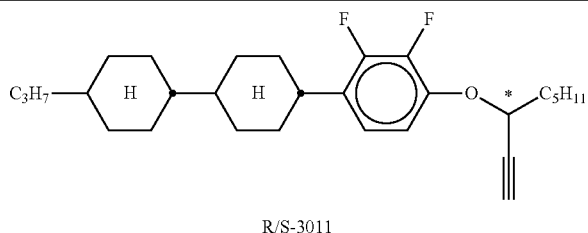

R/S-3011

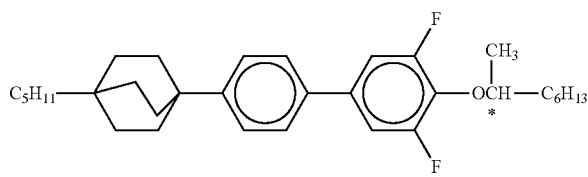

R/S-4011

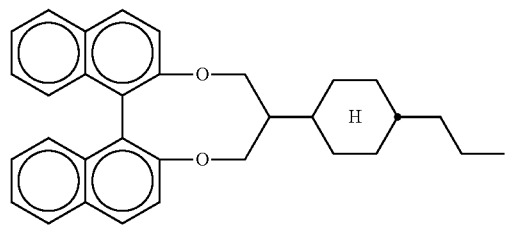

R/S-5011

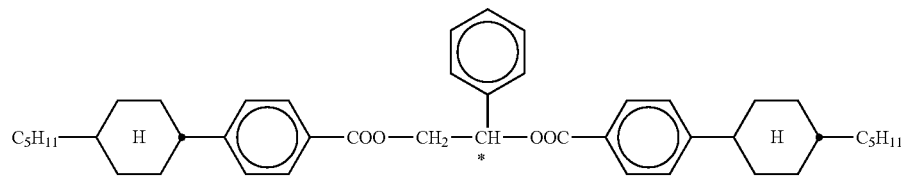

R/S-1011

Table B shows possible chiral dopants which can be added to the LC media according to the invention.

The LC media preferably comprise 0 to 10% by weight, in particular 0.01 to 5% by weight, particularly preferably 0.1 to 3% by weight, of dopants. The LC media preferably comprise one or more dopants selected from the group consisting of compounds from Table B.

TABLE C

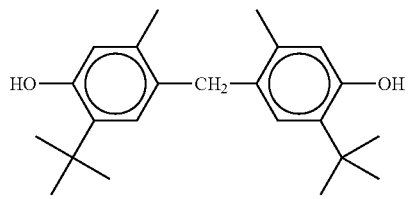

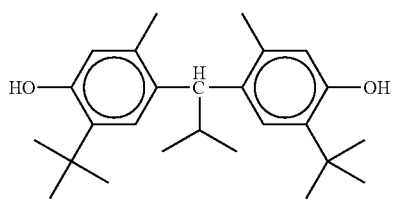

TABLE C-continued
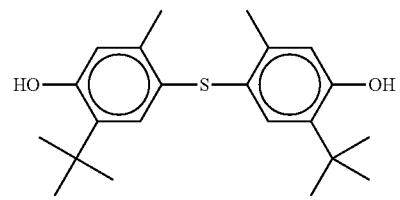
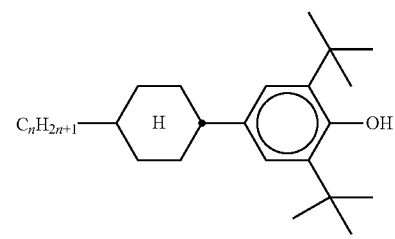
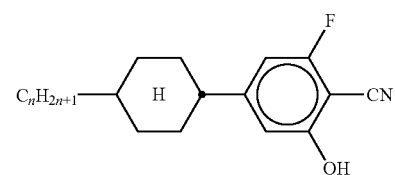
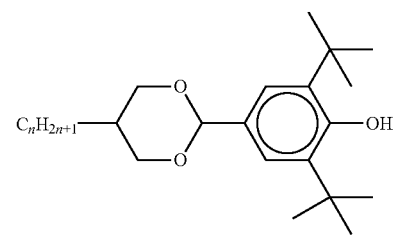
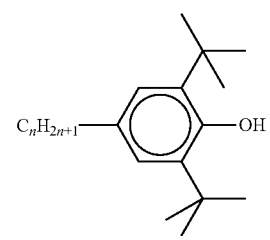
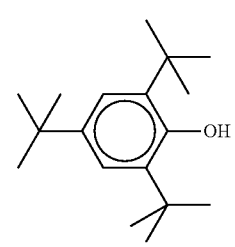
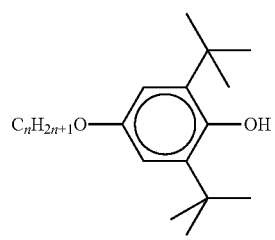

TABLE C-continued
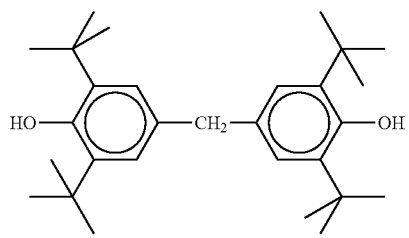
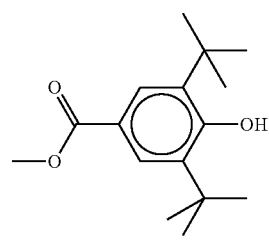
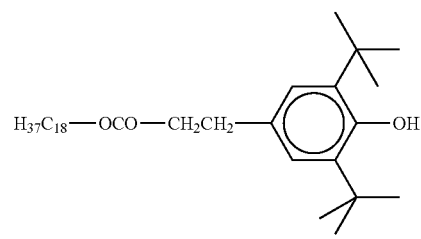
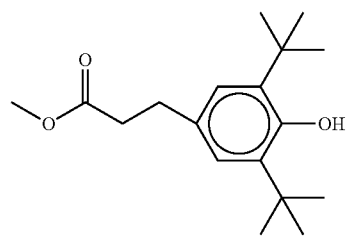
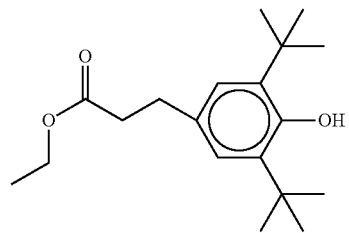
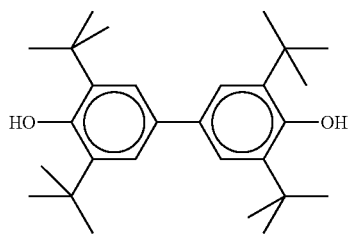

TABLE C-continued
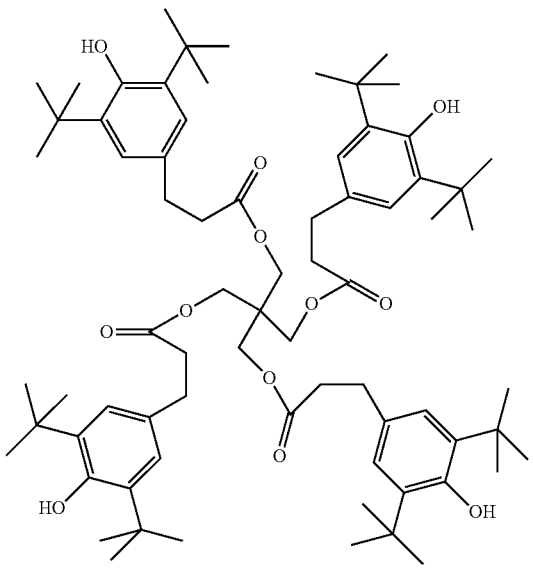 [SMILES: CC(C)(C)c1cc(CCC(=O)OCC(COC(=O)CCc2cc(C(C)(C)C)c(O)c(C(C)(C)C)c2)(COC(=O)CCc2cc(C(C)(C)C)c(O)c(C(C)(C)C)c2)COC(=O)CCc2cc(C(C)(C)C)c(O)c(C(C)(C)C)c2)cc(C(C)(C)C)c1O]
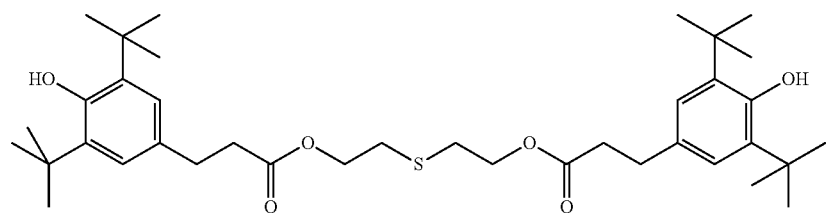 [SMILES: CC(C)(C)c1cc(CCC(=O)OCCSCCOC(=O)CCc2cc(C(C)(C)C)c(O)c(C(C)(C)C)c2)cc(C(C)(C)C)c1O]
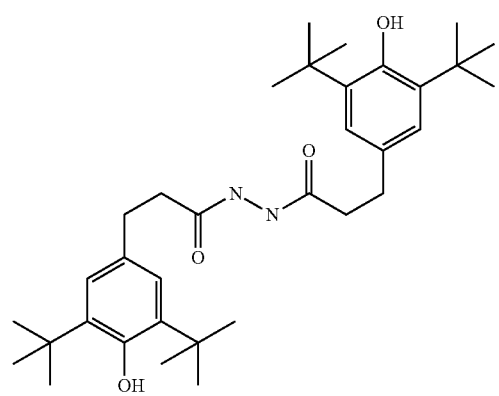 [SMILES: CC(C)(C)c1cc(CCC(=O)NNC(=O)CCc2cc(C(C)(C)C)c(O)c(C(C)(C)C)c2)cc(C(C)(C)C)c1O]
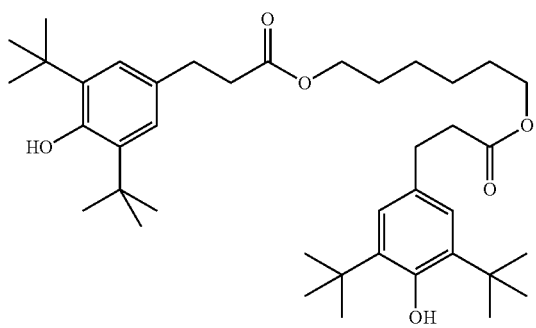 [SMILES: CC(C)(C)c1cc(CCC(=O)OCCCCCCOC(=O)CCc2cc(C(C)(C)C)c(O)c(C(C)(C)C)c2)cc(C(C)(C)C)c1O]

TABLE C-continued
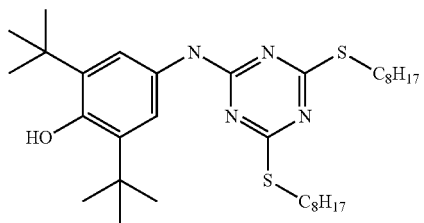
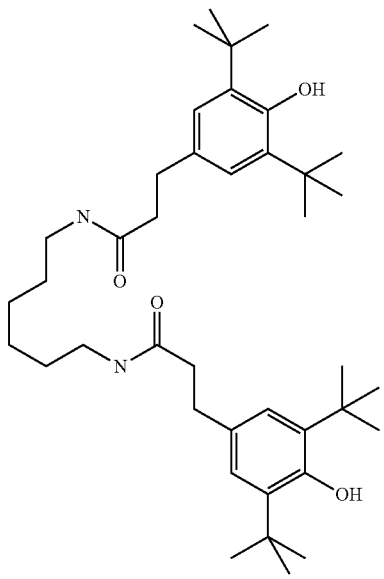 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]
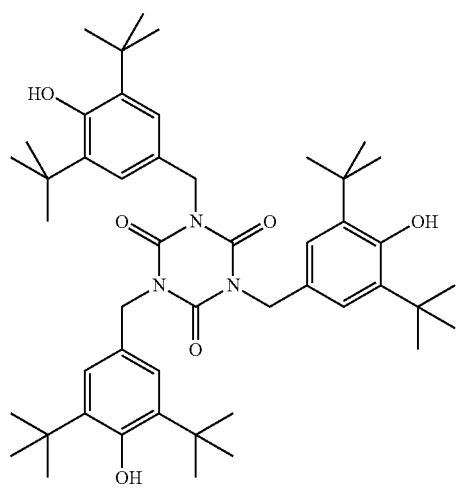 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]
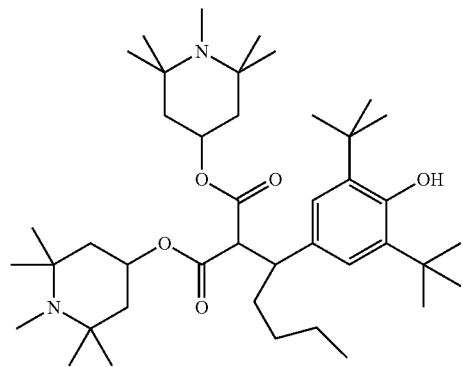 [SMILES: CCCCC(c1cc(C(C)(C)C)c(O)c(C(C)(C)C)c1)C(C(=O)OC1CC(C)(C)N(C)C(C)(C)C1)C(=O)OC1CC(C)(C)N(C)C(C)(C)C1]

TABLE C-continued
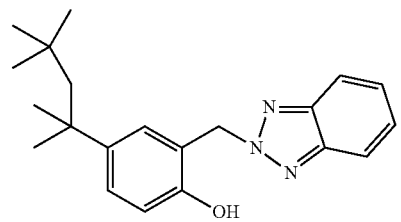 [SMILES: CC(C)(C)CC(C)(C)c1ccc(O)c(Cn2nc3ccccc3n2)c1]
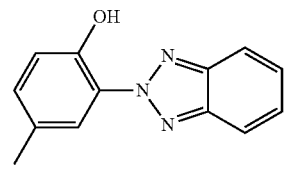 [SMILES: Cc1ccc(O)c(-n2nc3ccccc3n2)c1]
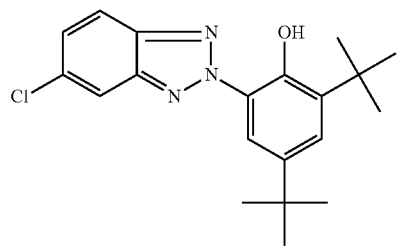 [SMILES: CC(C)(C)c1cc(-n2nc3ccc(Cl)cc3n2)c(O)c(C(C)(C)C)c1]
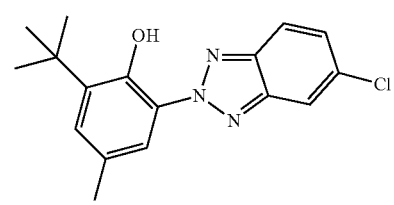 [SMILES: Cc1cc(-n2nc3ccc(Cl)cc3n2)c(O)c(C(C)(C)C)c1]
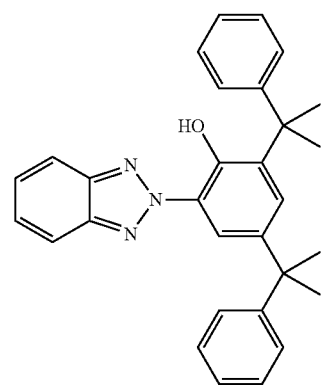 [SMILES: CC(C)(c1ccccc1)c1cc(-n2nc3ccccc3n2)c(O)c(C(C)(C)c2ccccc2)c1]
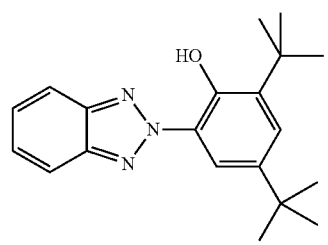 [SMILES: CC(C)(C)c1cc(-n2nc3ccccc3n2)c(O)c(C(C)(C)C)c1]

TABLE C-continued
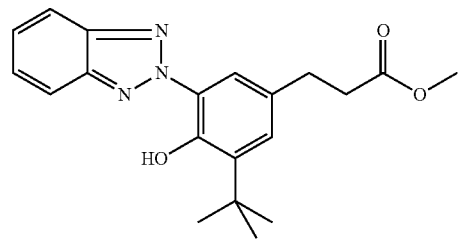 [SMILES: COC(=O)CCc1cc(-n2nc3ccccc3n2)c(O)c(C(C)(C)C)c1]
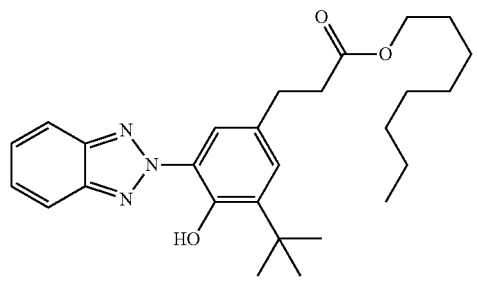 [SMILES: CCCCCCCCOC(=O)CCc1cc(-n2nc3ccccc3n2)c(O)c(C(C)(C)C)c1]
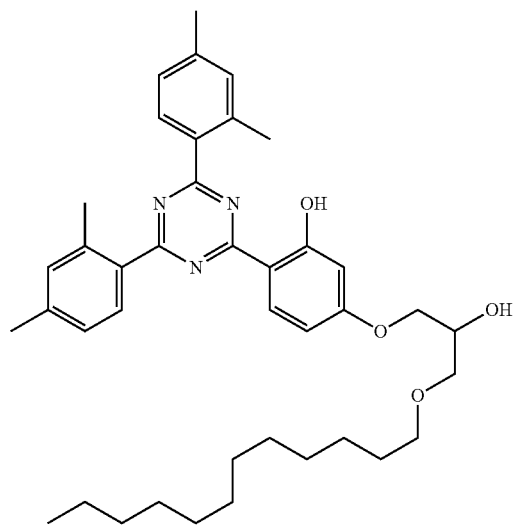 [SMILES: CCCCCCCCCCCCOCC(O)COc1ccc(-c2nc(-c3ccc(C)cc3C)nc(-c3ccc(C)cc3C)n2)c(O)c1]
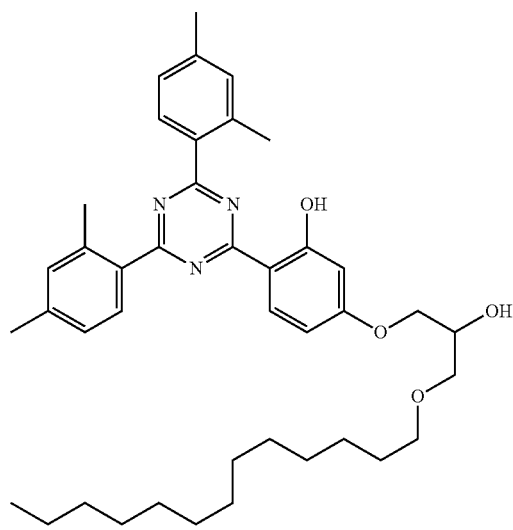 [SMILES: CCCCCCCCCCCCCOCC(O)COc1ccc(-c2nc(-c3ccc(C)cc3C)nc(-c3ccc(C)cc3C)n2)c(O)c1]

TABLE C-continued

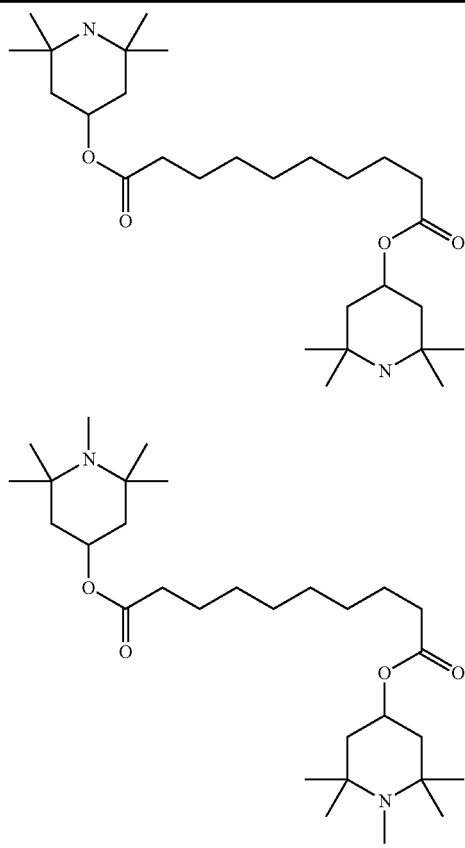

Table C shows possible stabilisers which can be added to the LC media according to the invention.
(n here denotes an integer from 1 to 12, preferably 1, 2, 3, 4, 5, 6, 7 or 8, terminal methyl groups are not shown).

The LC media preferably comprise 0 to 10% by weight, in particular 1 ppm to 5% by weight, particularly preferably 1 ppm to 1% by weight, of stabilisers. The LC media preferably comprise one or more stabilisers selected from the group consisting of compounds from Table C.

TABLE D

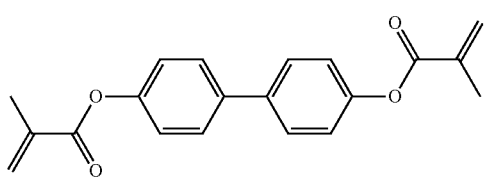 [SMILES: C=C(C)C(=O)Oc1ccc(-c2ccc(OC(=O)C(=C)C)cc2)cc1]

RM-1

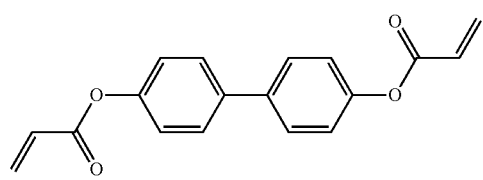 [SMILES: C=CC(=O)Oc1ccc(-c2ccc(OC(=O)C=C)cc2)cc1]

RM-2

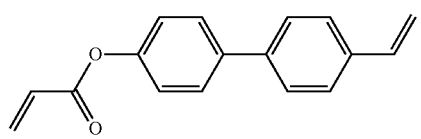 [SMILES: C=CC(=O)Oc1ccc(-c2ccc(C=C)cc2)cc1]

RM-3

TABLE D-continued
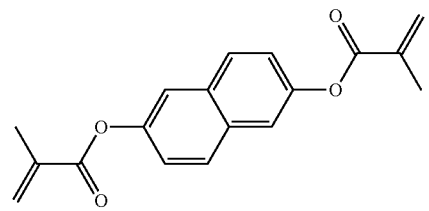 [SMILES: C=C(C)C(=O)Oc1ccc2cc(OC(=O)C(=C)C)ccc2c1] RM-4
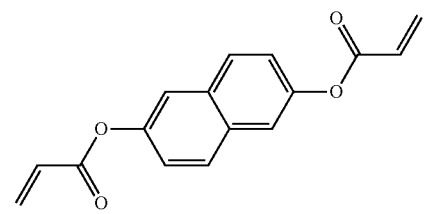 [SMILES: C=CC(=O)Oc1ccc2cc(OC(=O)C=C)ccc2c1] RM-5
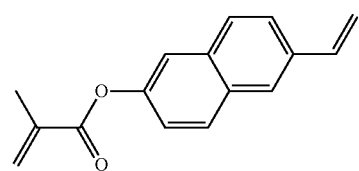 [SMILES: C=Cc1ccc2cc(OC(=O)C(=C)C)ccc2c1] RM-6
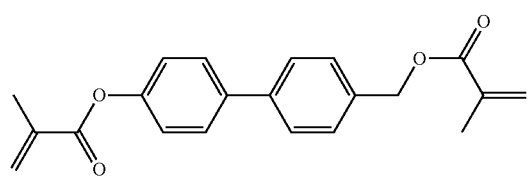 [SMILES: C=C(C)C(=O)OCc1ccc(-c2ccc(OC(=O)C(=C)C)cc2)cc1] RM-7
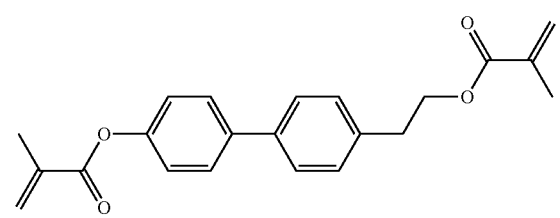 [SMILES: C=C(C)C(=O)OCCc1ccc(-c2ccc(OC(=O)C(=C)C)cc2)cc1] RM-8
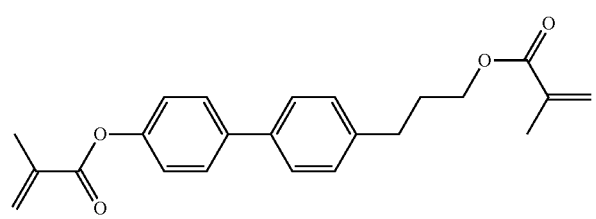 [SMILES: C=C(C)C(=O)OCCCc1ccc(-c2ccc(OC(=O)C(=C)C)cc2)cc1] RM-9
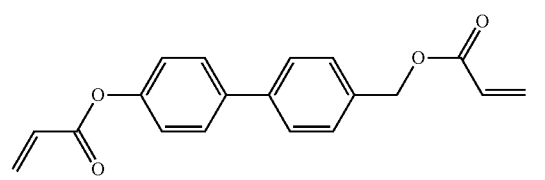 [SMILES: C=CC(=O)OCc1ccc(-c2ccc(OC(=O)C=C)cc2)cc1] RM-10
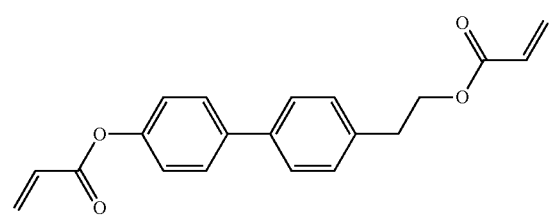 [SMILES: C=CC(=O)OCCc1ccc(-c2ccc(OC(=O)C=C)cc2)cc1] RM-11

TABLE D-continued
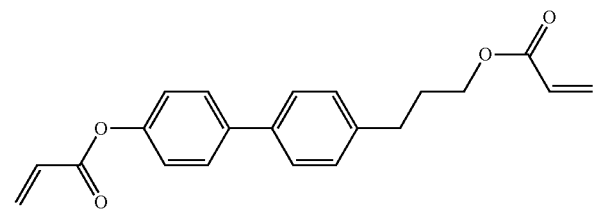 [SMILES: C=CC(=O)OCCCc1ccc(-c2ccc(OC(=O)C=C)cc2)cc1]
RM-12
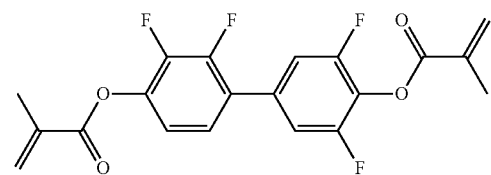 [SMILES: C=C(C)C(=O)Oc1ccc(-c2cc(F)c(OC(=O)C(=C)C)c(F)c2)c(F)c1F]
RM-13
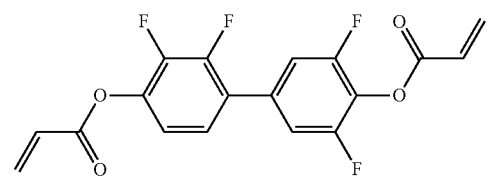 [SMILES: C=CC(=O)Oc1ccc(-c2cc(F)c(OC(=O)C=C)c(F)c2)c(F)c1F]
RM-14
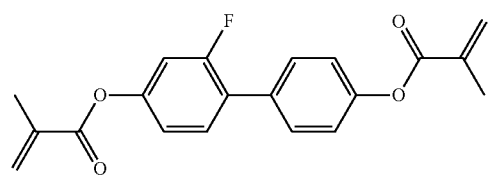 [SMILES: C=C(C)C(=O)Oc1ccc(-c2ccc(OC(=O)C(=C)C)cc2F)cc1]
RM-15
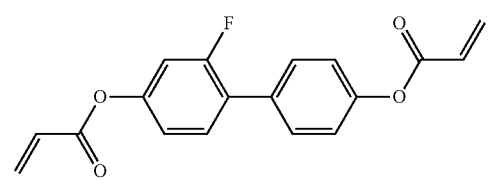 [SMILES: C=CC(=O)Oc1ccc(-c2ccc(OC(=O)C=C)cc2F)cc1]
RM-16
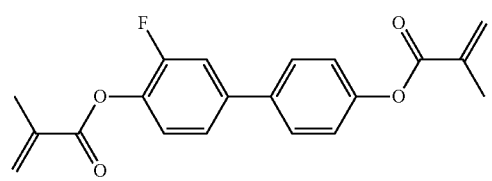 [SMILES: C=C(C)C(=O)Oc1ccc(-c2ccc(OC(=O)C(=C)C)c(F)c2)cc1]
RM-17
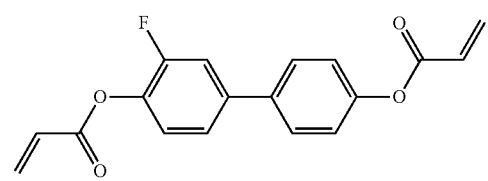 [SMILES: C=CC(=O)Oc1ccc(-c2ccc(OC(=O)C=C)c(F)c2)cc1]
RM-18
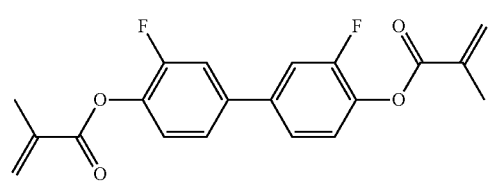
RM-19

TABLE D-continued
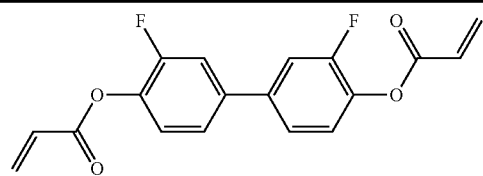 RM-20
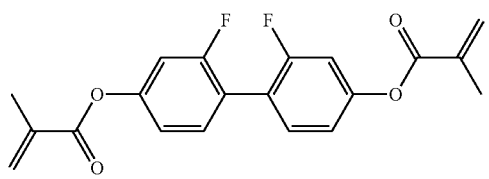 RM-21
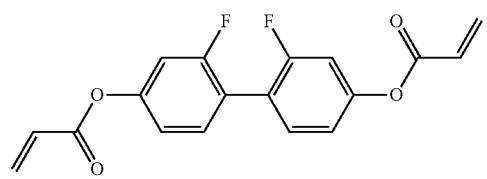 RM-22
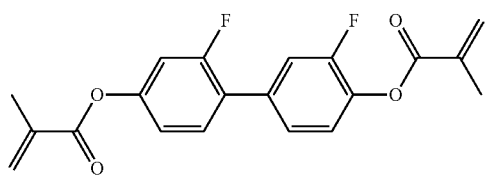 [SMILES: C=C(C)C(=O)Oc1ccc(-c2ccc(OC(=O)C(=C)C)c(F)c2)cc1F] RM-23
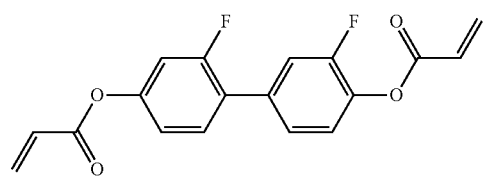 [SMILES: C=CC(=O)Oc1ccc(-c2ccc(OC(=O)C=C)c(F)c2)c(F)c1] RM-24
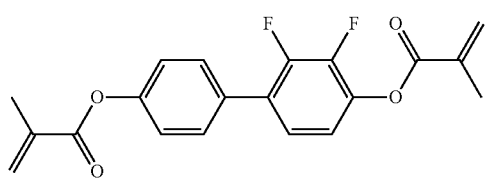 RM-25
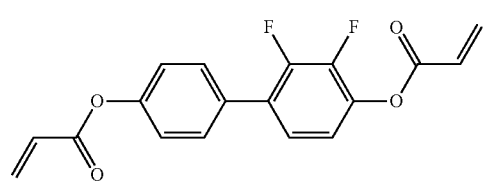 RM-26
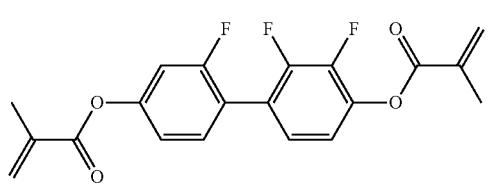 [SMILES: C=C(C)C(=O)Oc1ccc(-c2ccc(OC(=O)C(=C)C)c(F)c2F)c(F)c1] RM-27
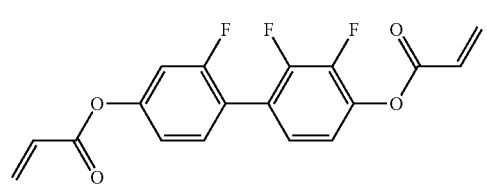 RM-28

TABLE D-continued
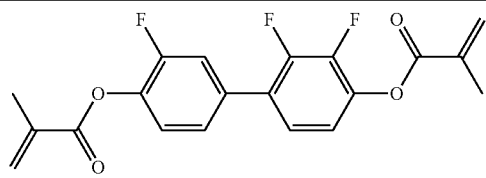
RM-29
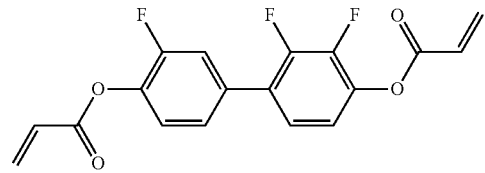
RM-30
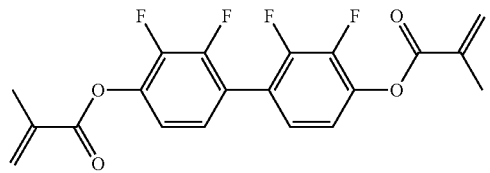
RM-31
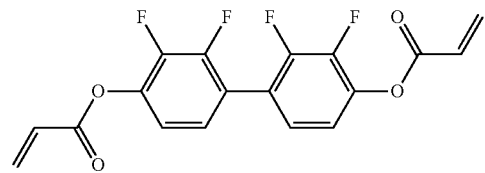 [SMILES: C=CC(=O)Oc1ccc(-c2ccc(OC(=O)C=C)c(F)c2F)c(F)c1]
RM-32
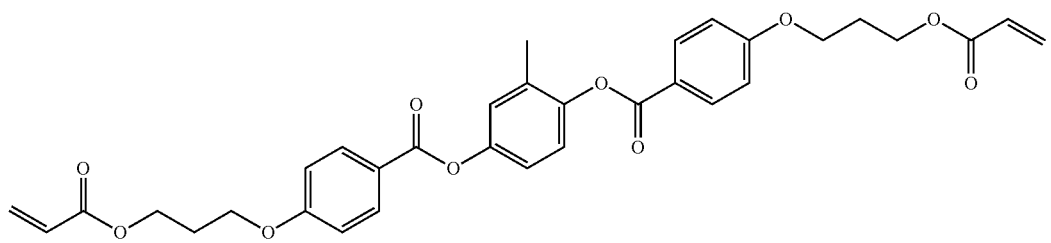 [SMILES: C=CC(=O)OCCCOc1ccc(C(=O)Oc2ccc(OC(=O)c3ccc(OCCCOC(=O)C=C)cc3)c(C)c2)cc1]
RM-33
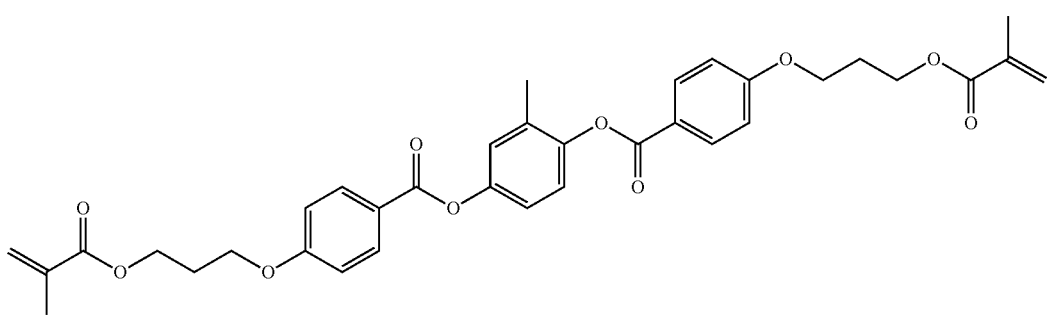 [SMILES: C=C(C)C(=O)OCCCOc1ccc(C(=O)Oc2ccc(OC(=O)c3ccc(OCCCOC(=O)C(=C)C)cc3)c(C)c2)cc1]
RM-34
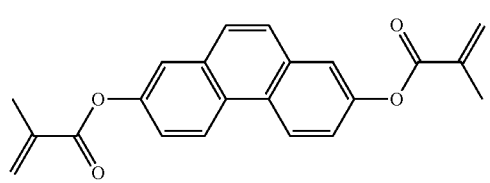 [SMILES: C=C(C)C(=O)Oc1ccc2c(ccc3cc(OC(=O)C(=C)C)ccc32)c1]
RM-35
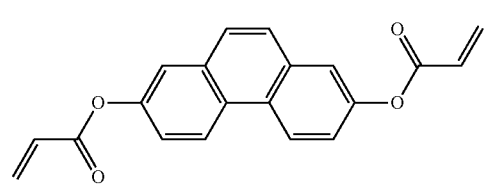 [SMILES: C=CC(=O)Oc1ccc2c(ccc3cc(OC(=O)C=C)ccc32)c1]
RM-36

TABLE D-continued
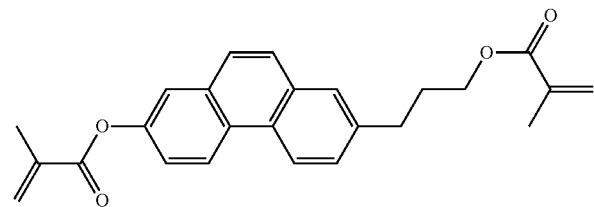 [SMILES: C=C(C)C(=O)OCCCc1ccc2c(ccc3cc(OC(=O)C(=C)C)ccc32)c1] RM-37
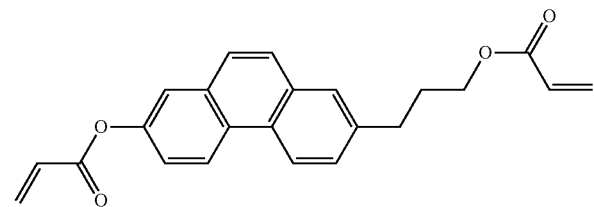 [SMILES: C=CC(=O)OCCCc1ccc2c(ccc3cc(OC(=O)C=C)ccc32)c1] RM-38
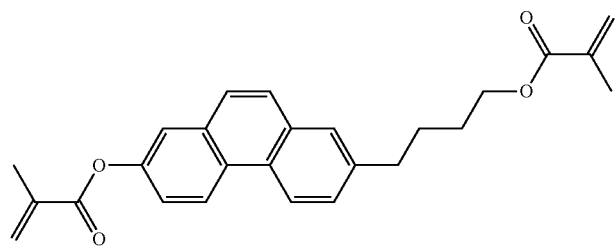 [SMILES: C=C(C)C(=O)OCCCCc1ccc2c(ccc3cc(OC(=O)C(=C)C)ccc32)c1] RM-39
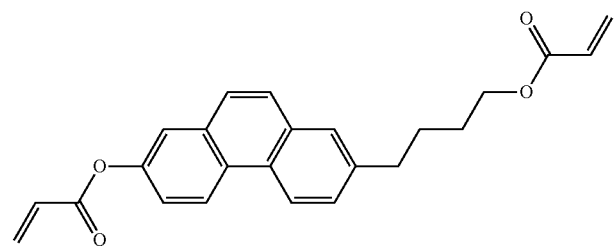 [SMILES: C=CC(=O)OCCCCc1ccc2c(ccc3cc(OC(=O)C=C)ccc32)c1] RM-40
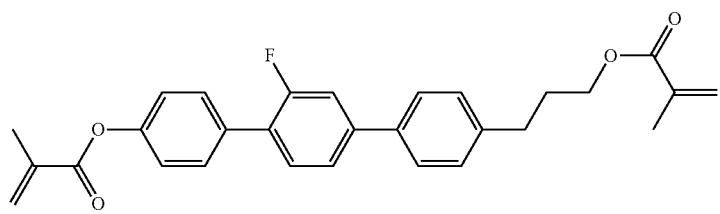 [SMILES: C=C(C)C(=O)OCCCc1ccc(-c2ccc(-c3ccc(OC(=O)C(=C)C)cc3)c(F)c2)cc1] RM-41
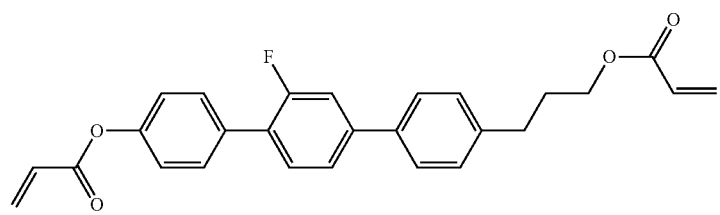 [SMILES: C=CC(=O)OCCCc1ccc(-c2ccc(-c3ccc(OC(=O)C=C)cc3)c(F)c2)cc1] RM-42
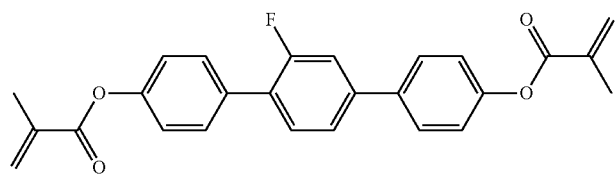 RM-43

TABLE D-continued
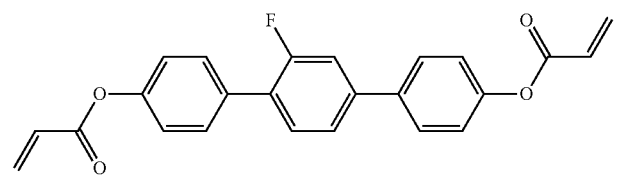 [SMILES: C=CC(=O)Oc1ccc(-c2ccc(-c3ccc(OC(=O)C=C)cc3)c(F)c2)cc1] RM-44
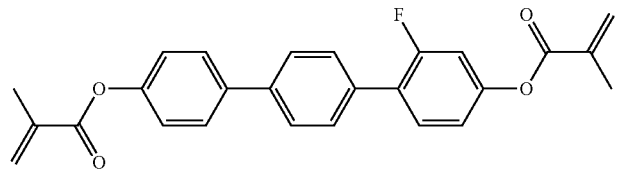 [SMILES: C=C(C)C(=O)Oc1ccc(-c2ccc(-c3ccc(OC(=O)C(=C)C)cc3F)cc2)cc1] RM-45
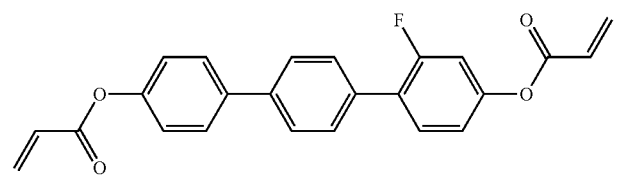 [SMILES: C=CC(=O)Oc1ccc(-c2ccc(-c3ccc(OC(=O)C=C)cc3F)cc2)cc1] RM-46
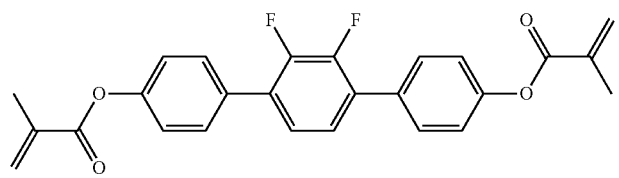 RM-47
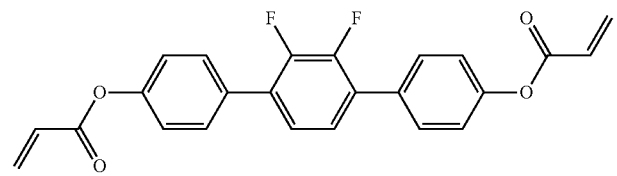 [SMILES: C=C(C)C(=O)Oc1ccc(-c2ccc(-c3ccc(OC(=O)C(=C)C)cc3)c(F)c2F)cc1] RM-48
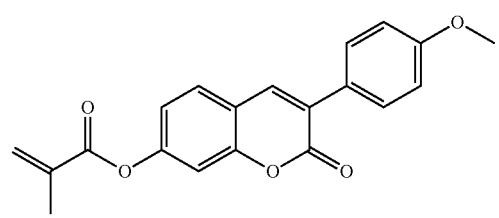 [SMILES: C=C(C)C(=O)Oc1ccc2cc(-c3ccc(OC)cc3)c(=O)oc2c1] RM-49
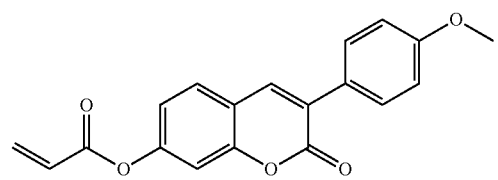 [SMILES: C=CC(=O)Oc1ccc2cc(-c3ccc(OC)cc3)c(=O)oc2c1] RM-50
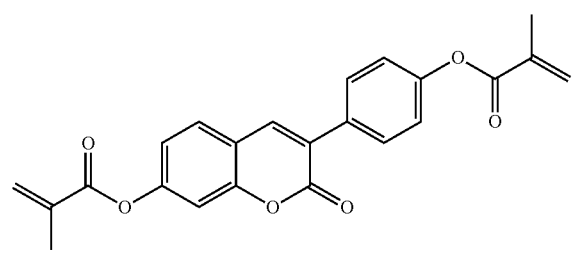 [SMILES: C=C(C)C(=O)Oc1ccc(-c2cc3ccc(OC(=O)C(=C)C)cc3oc2=O)cc1] RM-51

TABLE D-continued
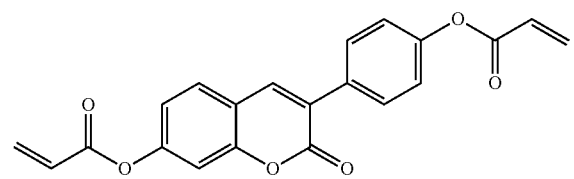 [SMILES: C=CC(=O)Oc1ccc(-c2cc3ccc(OC(=O)C=C)cc3oc2=O)cc1] RM-52
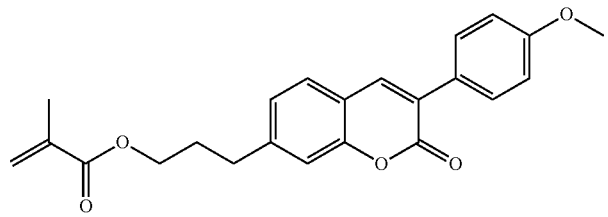 [SMILES: C=C(C)C(=O)OCCCc1ccc2cc(-c3ccc(OC)cc3)c(=O)oc2c1] RM-53
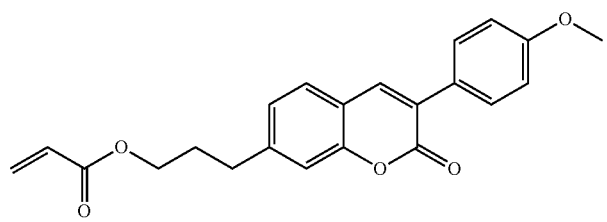 [SMILES: C=CC(=O)OCCCc1ccc2cc(-c3ccc(OC)cc3)c(=O)oc2c1] RM-54
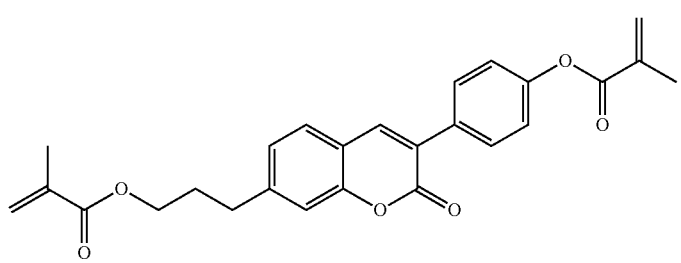 [SMILES: C=C(C)C(=O)OCCCc1ccc2cc(-c3ccc(OC(=O)C(=C)C)cc3)c(=O)oc2c1] RM-55
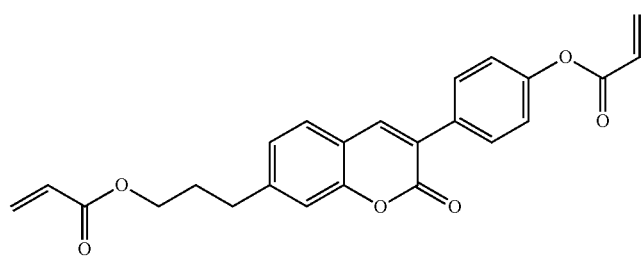 [SMILES: C=CC(=O)OCCCc1ccc2cc(-c3ccc(OC(=O)C=C)cc3)c(=O)oc2c1] RM-56
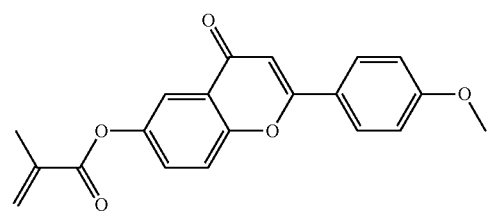 [SMILES: C=C(C)C(=O)Oc1ccc2oc(-c3ccc(OC)cc3)cc(=O)c2c1] RM-57
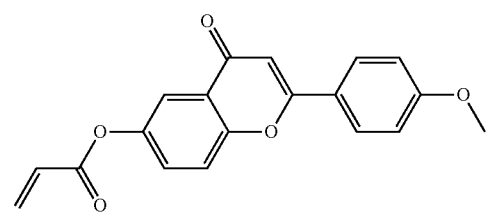 [SMILES: C=CC(=O)Oc1ccc2oc(-c3ccc(OC)cc3)cc(=O)c2c1] RM-58

TABLE D-continued
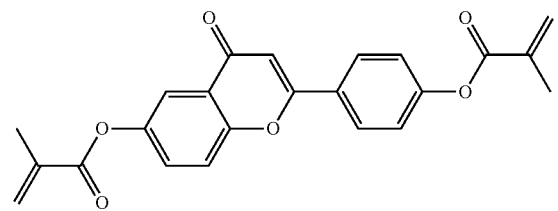 [SMILES: C=C(C)C(=O)Oc1ccc(-c2cc(=O)c3cc(OC(=O)C(=C)C)ccc3o2)cc1] RM-59
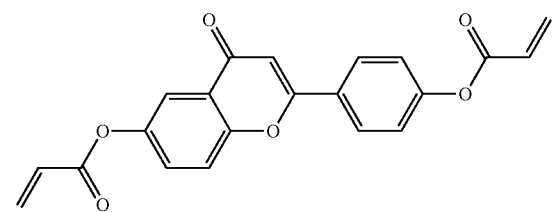 [SMILES: C=CC(=O)Oc1ccc(-c2cc(=O)c3cc(OC(=O)C=C)ccc3o2)cc1] RM-60
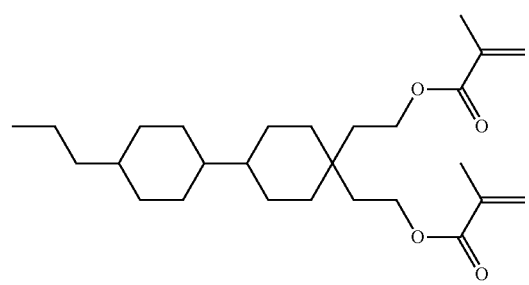 [SMILES: C=C(C)C(=O)OCCC1(CCOC(=O)C(=C)C)CCC(C2CCC(CCC)CC2)CC1] RM-61
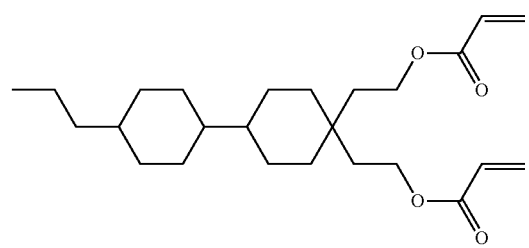 [SMILES: C=CC(=O)OCCC1(CCOC(=O)C=C)CCC(C2CCC(CCC)CC2)CC1] RM-62
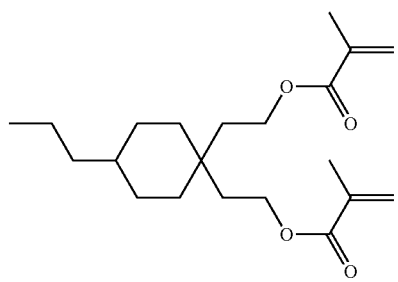 [SMILES: C=C(C)C(=O)OCCC1(CCOC(=O)C(=C)C)CCC(CCC)CC1] RM-63
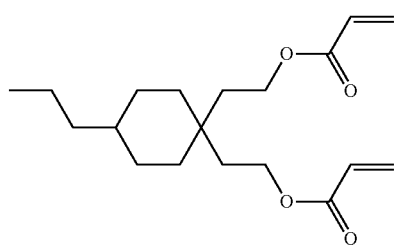 [SMILES: C=CC(=O)OCCC1(CCOC(=O)C=C)CCC(CCC)CC1] RM-64
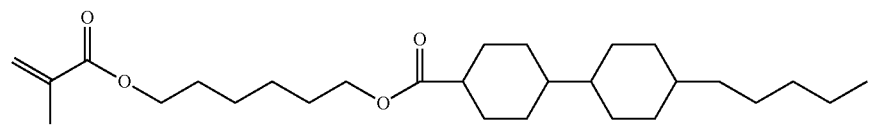 RM-65

TABLE D-continued
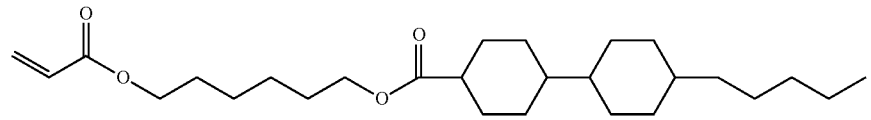 [SMILES: C=CC(=O)OCCCCCCOC(=O)C1CCC(C2CCC(CCCCC)CC2)CC1]
RM-66
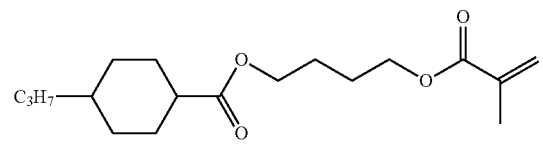
RM-67
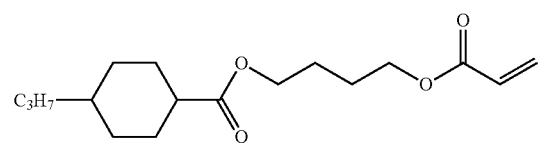
RM-68
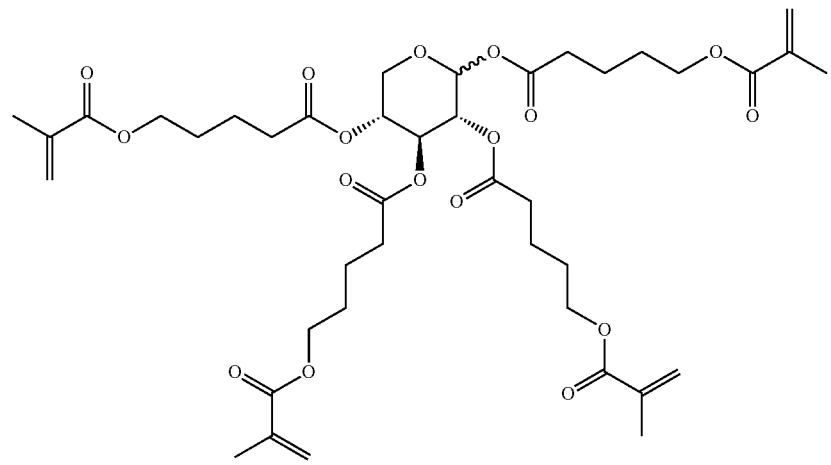 [SMILES: C=C(C)C(=O)OCCCCC(=O)OC1OC[C@@H](OC(=O)CCCCOC(=O)C(=C)C)[C@H](OC(=O)CCCCOC(=O)C(=C)C)[C@H]1OC(=O)CCCCOC(=O)C(=C)C]
RM-69
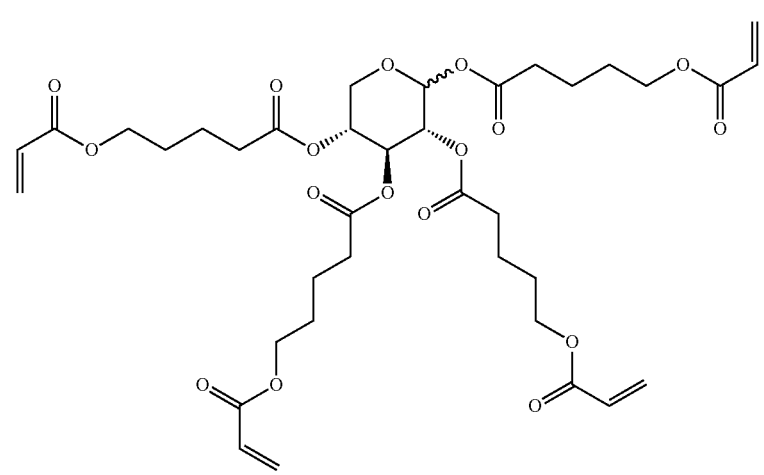 [SMILES: C=CC(=O)OCCCCC(=O)OC1OC[C@@H](OC(=O)CCCCOC(=O)C=C)[C@H](OC(=O)CCCCOC(=O)C=C)[C@H]1OC(=O)CCCCOC(=O)C=C]
RM-70

TABLE D-continued
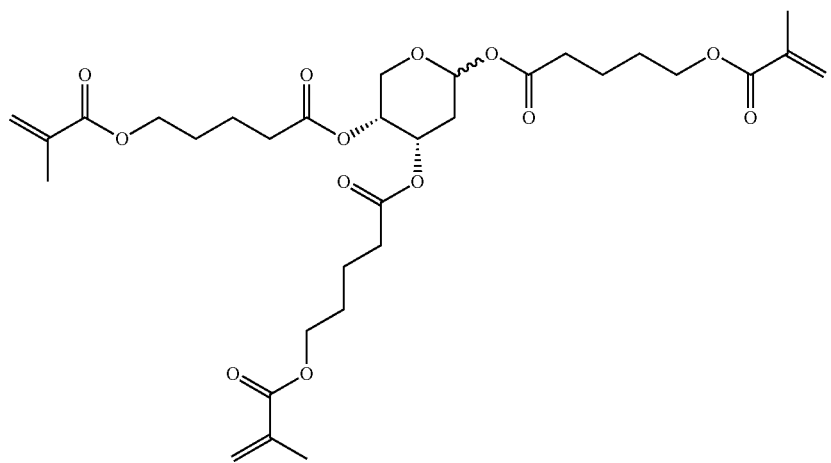 [SMILES: C=C(C)C(=O)OCCCCC(=O)OC1C[C@H](OC(=O)CCCCOC(=O)C(=C)C)[C@H](OC(=O)CCCCOC(=O)C(=C)C)CO1]
RM-71
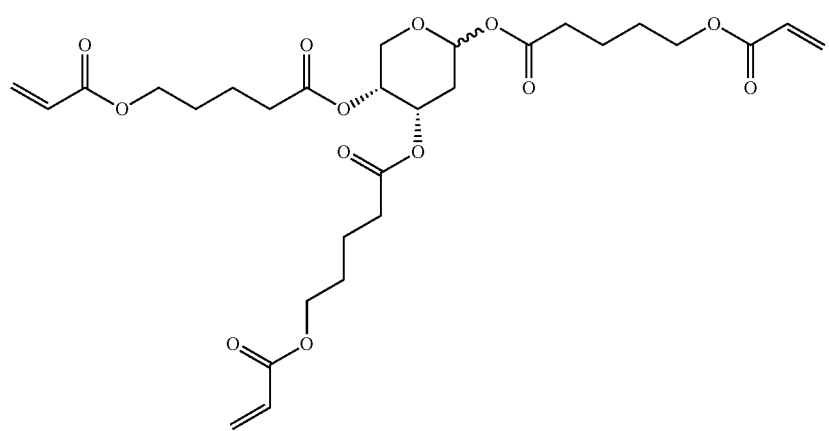 [SMILES: C=CC(=O)OCCCCC(=O)OC1C[C@H](OC(=O)CCCCOC(=O)C=C)[C@H](OC(=O)CCCCOC(=O)C=C)CO1]
RM-72
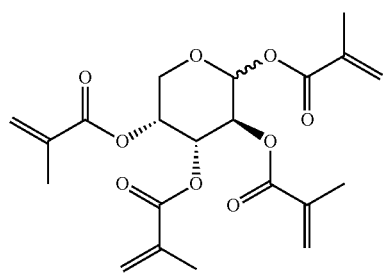 [SMILES: C=C(C)C(=O)OC1OC[C@@H](OC(=O)C(=C)C)[C@@H](OC(=O)C(=C)C)[C@@H]1OC(=O)C(=C)C]
RM-73
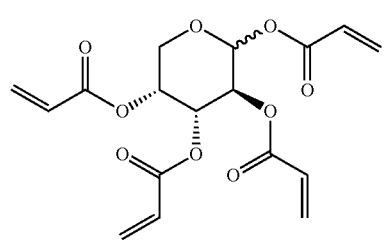 [SMILES: C=CC(=O)OC1OC[C@@H](OC(=O)C=C)[C@@H](OC(=O)C=C)[C@@H]1OC(=O)C=C]
RM-74

Table D shows illustrative compounds which can be used in the LC media in accordance with the present invention, preferably as reactive mesogenic compounds.

In a preferred embodiment of the present invention, the mesogenic media comprise one or more compounds selected from the group of the compounds from Table D.

In addition, the following abbreviations and symbols are used:
$V_0$ threshold voltage, capacitive [V] at 20° C.,
$n_e$ extraordinary refractive index at 20° C. and 589 nm,
$n_o$ ordinary refractive index at 20° C. and 589 nm,
Δn optical anisotropy at 20° C. and 589 nm,
$\varepsilon_\perp$ dielectric permittivity perpendicular to the director at 20° C. and 1 kHz,
$\varepsilon\|$ dielectric permittivity parallel to the director at 20° C. and 1 kHz,
Δε dielectric anisotropy at 20° C. and 1 kHz,
cl.p., T(N,I) clearing point [° C.],
$\gamma_1$ rotational viscosity at 20° C. [mPa·s],
$K_1$ elastic constant, "splay" deformation at 20° C. [pN],
$K_2$ elastic constant, "twist" deformation at 20° C. [pN],
$K_3$ elastic constant, "bend" deformation at 20° C. [pN].

Unless explicitly noted otherwise, all concentrations in the present application are quoted in percent by weight and relate to the corresponding mixture as a whole, comprising all solid or liquid-crystalline components, without solvents.

Unless explicitly noted otherwise, all temperature values indicated in the present application, such as, for example, for the melting point T(C,N), the transition from the smectic (S) to the nematic (N) phase T(S,N) and the clearing point T(N,I), are quoted in degrees Celsius (° C.). M.p. denotes melting point, cl.p.=clearing point. Furthermore, C=crystalline state, N=nematic phase, S=smectic phase and I=isotropic phase. The data between these symbols represent the transition temperatures.

All physical properties are and have been determined in accordance with "Merck Liquid Crystals, Physical Properties of Liquid Crystals", Status November 1997, Merck KGaA, Germany, and apply for a temperature of 20° C., and Δn is determined at 589 nm and Δε at 1 kHz, unless explicitly indicated otherwise in each case.

The term "threshold voltage" for the present invention relates to the capacitive threshold ($V_0$), also known as the Freedericks threshold, unless explicitly indicated otherwise. In the examples, the optical threshold may also, as generally usual, be quoted for 10% relative contrast ($V_{10}$).

Unless stated otherwise, the process of polymerizing the polymerisable compounds in the PSA displays as described above and below is carried out at a temperature where the LC medium exhibits a liquid crystal phase, preferably a nematic phase, and most preferably is carried out at room temperature.

The display used for measurement of the capacitive threshold voltage consists of two plane-parallel glass outer plates at a separation of 20 μm, each of which has on the inside an electrode layer and an unrubbed polyimide alignment layer on top, which effect a homeotropic edge alignment of the liquid-crystal molecules.

The display or test cell used for measurement of the tilt angles consists of two plane-parallel glass outer plates at a separation of 4 μm, each of which has on the inside an electrode layer and a polyimide alignment layer on top, where the two polyimide layers are rubbed antiparallel to one another and effect a homeotropic edge alignment of the liquid-crystal molecules.

The polymerisable compounds are polymerised in the display or test cell by irradiation with UVA light of defined intensity for a prespecified time, with a voltage simultaneously being applied to the display (usually 10 V to 30 V alternating current, 1 kHz). In the examples, unless indicated otherwise, a metal halide lamp and an intensity of 100 mW/cm$^2$ is used for polymerisation. The intensity is measured using a standard UVA meter (Hoenle UV-meter high end with UVA sensor).

The tilt angle is determined by crystal rotation experiment (Autronic-Melchers TBA-105). A low value (i.e. a large deviation from the 90° angle) corresponds to a large tilt here.

The VHR value is measured as follows: 0.3% of a polymerisable monomeric compound is added to the LC host mixture, and the resultant mixture is introduced into VA-VHR test cells (not rubbed, VA-polyimide alignment layer, LC-layer thickness d≈6 μm). The HR value is determined after 5 min at 100° C. before and after UV exposure at 1 V, 60 Hz, 64 μs pulse (measuring instrument: Autronic-Melchers VHRM-105).

Example 1

2-Methylacrylic acid-4-{8-[4-(2-methyl-acryloyloxy)-butyl]-3-[4-(2-methyl-acryloyloxy)-phenyl]-2-oxo-2H-chromen-6-yl}-butyl ester (1)

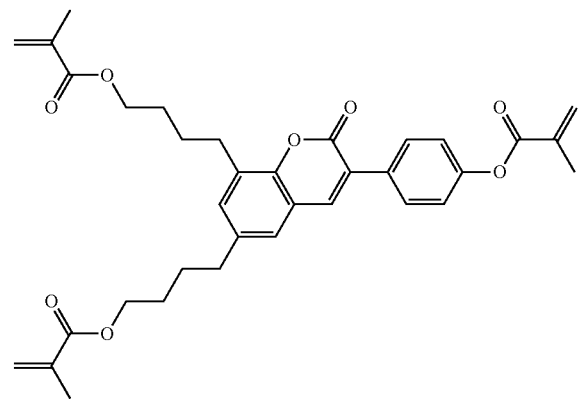

1.1
6,8-Dibromo-3-(4-methoxy-phenyl)-chromen-2-one

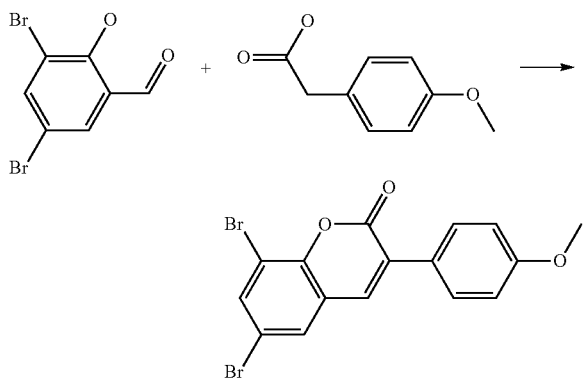

3,5-Dibromo-2-hydroxybenzaldehyd (30.0 g, 107 mmol) [CAS-Nr. 90-59-5] and 4-methoxyphenylacetic acid (35.7 g, 166 mmol) are heated in 51 ml acetic anhydride and 60 ml triethylamine overnight at reflux. The reaction mixture is cooled down to 80° C. and poured onto 1000 ml 2 M sodium hydroxide under stirring. After 5 min the precipitated product is filtered by vacuum, washed with water and digested two times with 100 ml ethanol. 6,8-Dibromo-3-(4-methoxy-phenyl)-chromen-2-one is obtained as a yellow solid.

$^1$H-NMR (300 MHz, CDCl$_3$)

δ=3.86 (s, 3H, OCH$_3$), 6.98 (AB-m$_c$, therein: J=8.9 Hz, 2H, Ph-H), 7.66 (AB-m$_c$, therein: J=8.9 Hz, 2H, Ph-H), 7.60 (d, J=2.2, Hz, 1H, Ar—H), 7.62 (s, 1H, Ar—H), 7.84 (d, J=2.2 Hz, 1H, Ar—H).

1.2. 6,8-Bis-(4-hydroxy-but-1-ynyl)-3-(4-methoxy-phenyl)-chromen-2-one

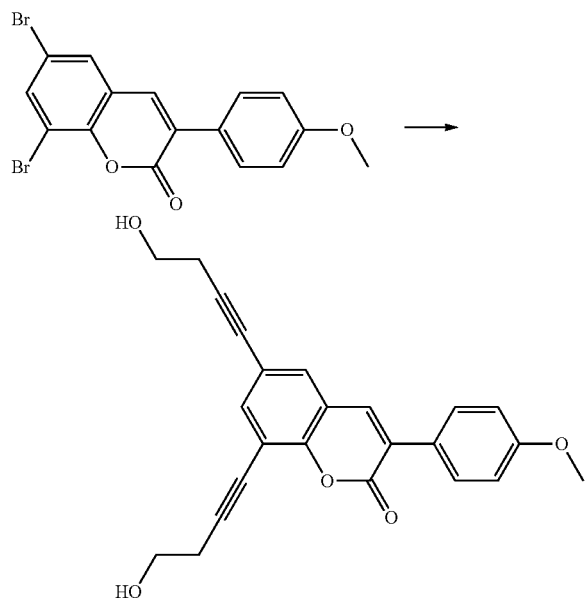

6,8-Dibromo-3-(4-methoxy-phenyl)-chromen-2-one (30.8 g, 75.1 mmol), copper(I)iodide (1.50 g, 7.88 mmol) and bis(acetonitril)palladium(II) chloride (5.00 g, 7.12 mmol) are dissolved in 300 ml DMF and 50 ml diisopropylamin at 70° C., and a solution of butyne-1-ol (20.0 g, 285 mmol) in 50 ml DMF is added dropwise within 30 min. The reaction mixture is stirred overnight at 80° C., then poured onto 300 ml water and acidified with 2 N hydrochloric acid. The precipitated product is filtered by vacuum, then filtered through silica gel with THF/toluene (4:1) and addition of a small amount of ethanol, and the crude product is recrystallized from toluene. 6,8-Bis-(4-hydroxy-but-1-ynyl)-3-(4-methoxy-phenyl)-chromen-2-one is obtained as light brown solid, which is pure enough to be used as starting material for the next step.

1.3 6,8-Bis-(4-hydroxy-butyl)-3-(4-methoxy-phenyl)-chromen-2-one

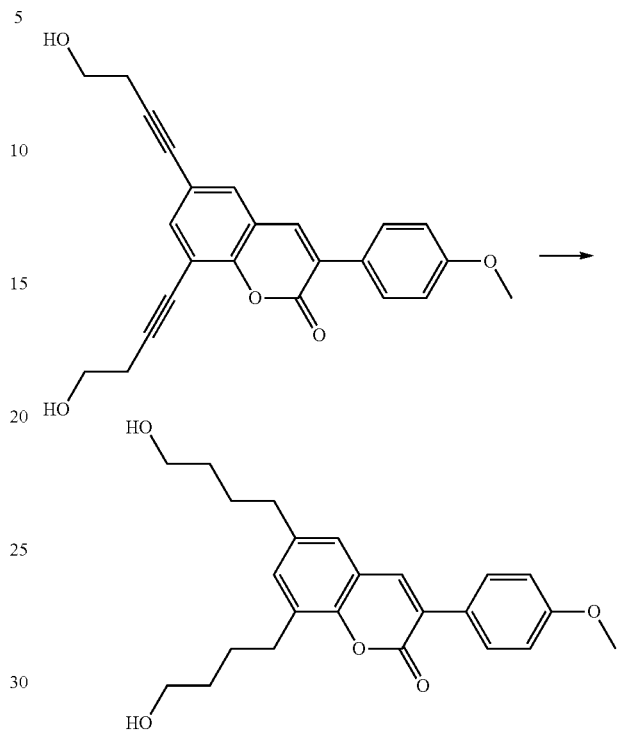

6,8-Bis-(4-hydroxy-but-1-ynyl)-3-(4-methoxy-phenyl)-chromen-2-one is hydrogenated in THF on Pd/activated charcoal until the reaction is completed. The catalyst is filtered off, the solvent removed in vacuo and the crude product is filtered through silica gel with THF/toluene (3:2) and recrystallized from toluene. 6,8-Bis-(4-hydroxy-butyl)-3-(4-methoxy-phenyl)-chromen-2-one is obtained as a colourless solid.

$^1$H-NMR (300 MHz, CDCl$_3$)

δ=1.47 (s, br., 1H, OH), 1.55-1.86 ppm (m, 8H, CH$_2$), 2.68 (t, J=7.4 Hz, 2H, Ar—CH$_2$—), 2.89 (t, J=7.3 Hz, 2H, Ar—CH$_2$—), 3.69 (m$_c$, 4 H, —CH$_2$—O—) 3.85 (s, 3H, OCH$_3$), 6.97 (AB-m$_c$, therein: J=8.9 Hz, 2H, Ph-H), 7.17 (dd, J=2.0 Hz, J=9.9 Hz, 2H, Ar—H), 7.67 (AB-m$_c$, therein: J=8.9 Hz, 2H, Ph-H), 7.70 (s, br., 1H, Ar—H).

1.4 6,8-Bis-(4-hydroxy-butyl)-3-(4-hydroxy-phenyl)-chromen-2-one

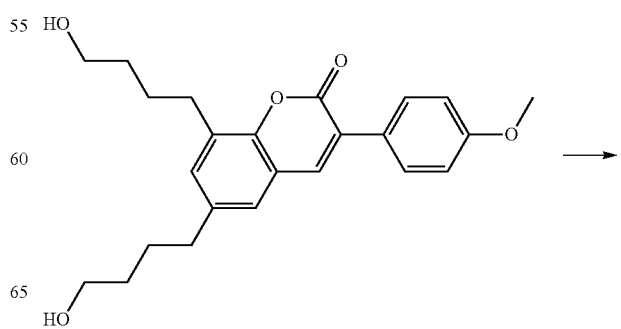

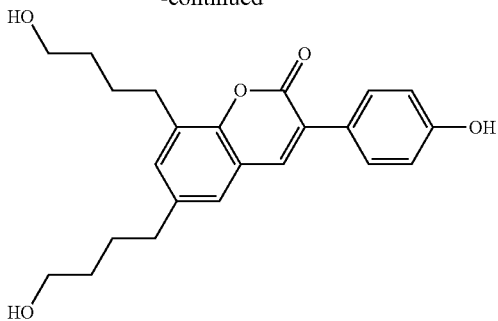

6,8-Bis-(4-hydroxy-butyl)-3-(4-methoxy-phenyl)-chromen-2-one (14.3 g, 36.0 mmol) is dissolved in 270 ml dichloromethane and a solution of boron tribromide (12 ml, 126 mmol) in 30 ml dichloromethane is added under ice-cooling. The cooling is removed and the reaction mixture is stirred overnight at room temp. The solution is poured onto ice/water, acidified with 2 N hydrochloric acid, and extracted three times with ethyl acetate. The combined organic layers are washed with water and dried over sodium sulfate. The solvent is removed in vacuo and the residue is filtered through silica gel with toluene/THF (7:3). 6,8-Bis-(4-hydroxy-butyl)-3-(4-hydroxy-phenyl)-chromen-2-one is obtained as a viscous oil.

1.5 2-Methyl-acrylic acid-4-{8-[4-(2-methyl-acryloyloxy)-butyl]-3-[4-(2-methyl-acryloyloxy)-phenyl]-2-oxo-2H-chromen-6-yl}-butyl ester

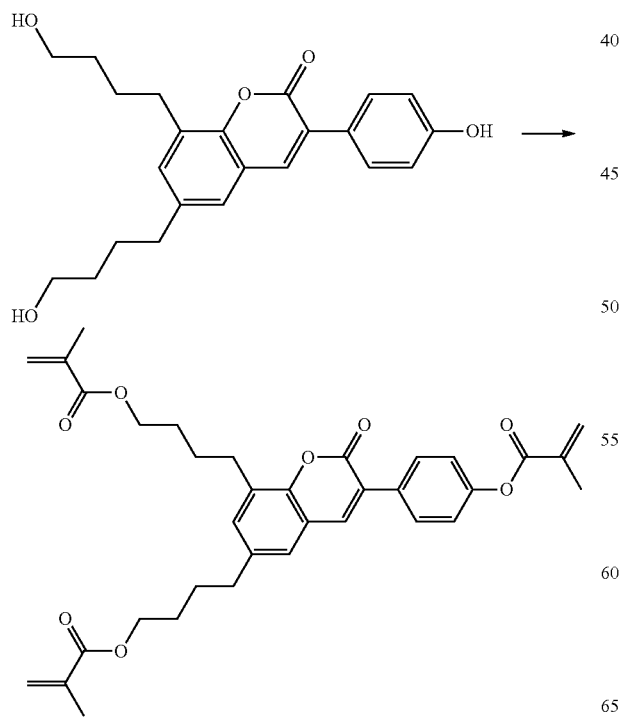

6,8-Bis-(4-hydroxy-butyl)-3-(4-hydroxy-phenyl)-chromen-2-one (10.1 g, 25.1 mmol) is suspended in 230 ml dichloromethane, methacrylic acid (8.5 g, 99.0 mmol) and DMAP (0.5 g) are added, and then a solution of 1-(3-Dimethylaminopropyl)-3-ethylcarbodiimid (15.0 g, 96.6 mmol) in 20 ml dichloromethane is added under ice-cooling. After 1 h the cooling is removed and the reaction mixture is stirred overnight at room temp. The solvent is removed in vacuo and the residue is purified by column chromatography on silica with dichloromethane/ethyl acetate (95:5) as eluent. 2-Methyl-acrylic acid-4-{8-[4-(2-methyl-acryloyloxy)-butyl]-3-[4-(2-methyl-acryloyloxy)-phenyl]-2-oxo-2H-chromen-6-yl}-butyl ester is obtained as a colourless oil.

$^1$H-NMR (300 MHz, CDCl$_3$)

δ=1.70-1.85 ppm (m, 8H, CH$_2$), 1.94 (m$_c$, 6 H, 2 Me), 2.08 (m$_c$, 3 H, Me), 2.70 (m$_c$, 2 H, Ar—CH$_2$—), 2.92 (m$_c$, 2 H, Ar—CH$_2$), 4.20 (m$_e$, —CH$_2$—O—), 5.55 (m$_c$, 2 H, 2 CHH═C(Me)COO—), 5.78 (m$_c$, 1 H, CHH═C(Me)COO—), 6.10 (m$_c$, m$_c$, 2 H, 2 CHH═C(Me)COO—), 6.37 (m$_c$, 1 H, CHH═C(Me)COO—), 7.15-7.24 (m, 3H, Ar—H), 7.71-7.80 (m, 4H, Ar—H).

Example 2

2-Methyl-acrylic acid-3-{3-[4-(2-methyl-acryloyloxy)-phenyl]-6-[3-(2-methyl-acryloyloxy)-propyl]-2-oxo-2H-chromen-8-yl}-propyl ester (2)

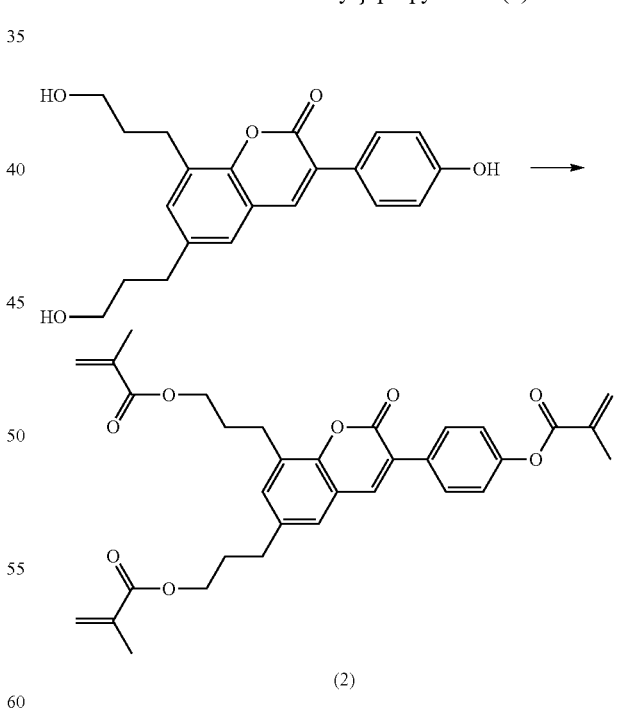

(2)

In analogy to example 1,2-methyl-acrylic acid-3-{3-[4-(2-methyl-acryloyloxy)-phenyl]-6-[3-(2-methyl-acryloyloxy)-propyl]-2-oxo-2H-chromen-8-yl}-propyl ester (2) is obtained from 3-(4-Hydroxy-phenyl)-6,8-bis-(3-hydroxy-propyl)-chromen-2-one as colourless crystals with a melting point of 49° C.

Example 3

2-Methylacrylic acid-2-{6-[2-(2-methyl-acryloyloxy)-ethyl]-3-[4-(2-methyl-acryloyloxy)-phenyl]-2-oxo-2H-chromen-8-yl}-ethyl ester (3)

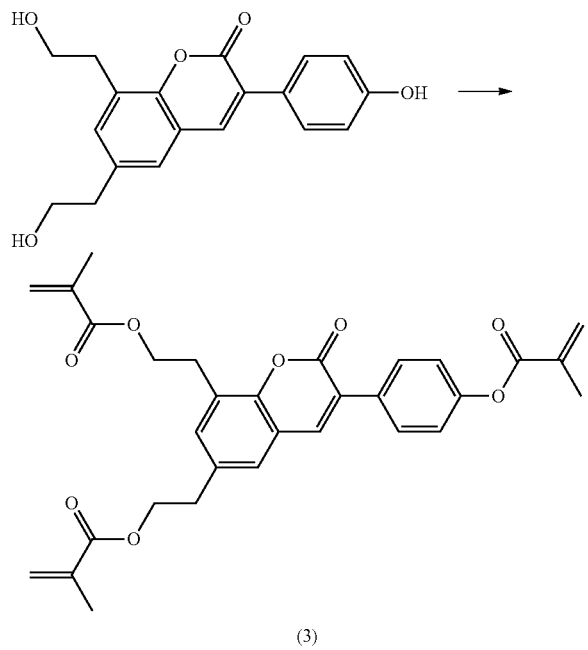

(3)

In analogy to example 1,2-methyl-acrylic acid-2-{6-[2-(2-methyl-acryloyloxy)-ethyl]-3-[4-(2-methyl-acryloyloxy)-phenyl]-2-oxo-2H-chromen-8-yl}-ethyl ester is obtained from 3-(4-hydroxy-phenyl)-6,8-bis-(2-hydroxy-ethyl)-chromen-2-one as colourless crystals.

Example 4

2-Methylacrylic acid-4-{6,7-bis-[3-(2-methyl-acryloyloxy)-butyl]-2-oxo-2H-chromen-3-yl}-phenyl ester (4)

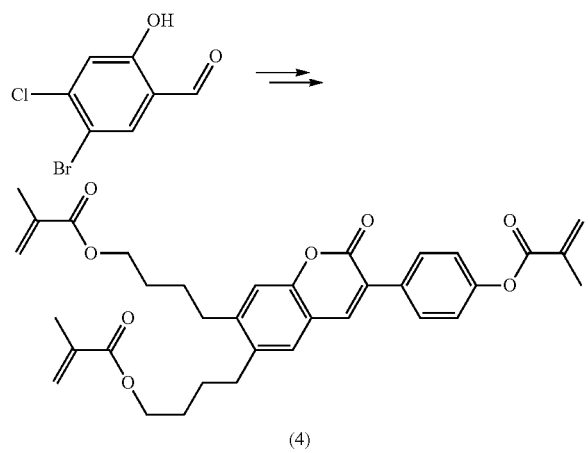

(4)

In analogy to the synthesis sequence as described in example 1,2-methyl-acrylic acid 4-{6,7-bis-[3-(2-methyl-acryloyloxy)-butyl]-2-oxo-2H-chromen-3-yl}-phenyl ester is obtained from 5-bromo-4-chlor-2-hydroxybenzaldehyde [CAS-No. 876492-31-8] as a colourless oil.

Example 5

2-Methyl-acrylic acid-4-{5,7-bis-[3-(2-methyl-acryloyloxy)-butyl]-2-oxo-2H-chromen-3-yl}-phenyl ester (5)

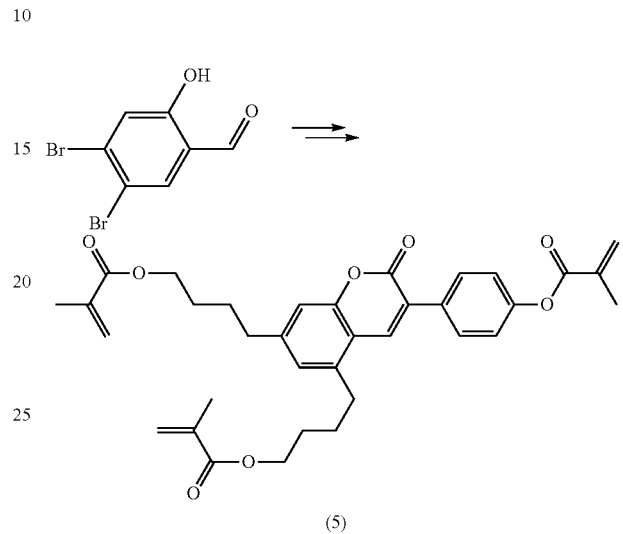

(5)

In analogy to the synthesis sequence as described in Example 1,2-methyl-acrylic acid-4-{5,7-bis-[3-(2-methyl-acryloyloxy)-butyl]-2-oxo-2H-chromen-3-yl}-phenyl ester is obtained from 2,4-dibromo-6-hydroxybenzaldehyde [CAS-No. 73289-92-6] as a colourless oil.

Example 6

2-Methyl-acrylic acid-4-{7,8-bis-[3-(2-methyl-acryloyloxy)-butyl]-2-oxo-2H-chromen-3-yl}-phenyl ester (6)

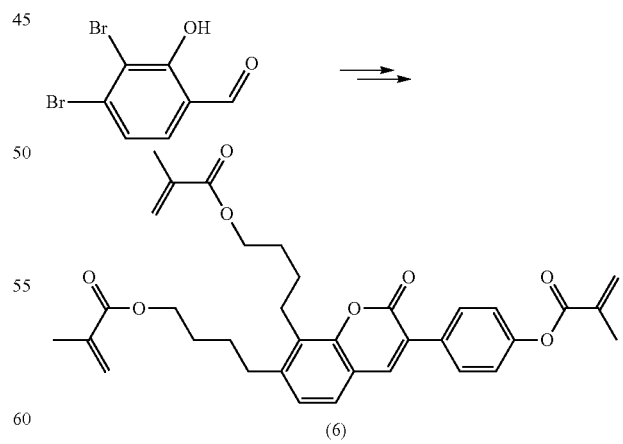

(6)

In analogy to the synthesis sequence as described in Example 1,2-methyl-acrylic acid-4-{7,8-bis-[3-(2-methyl-acryloyloxy)-butyl]-2-oxo-2H-chromen-3-yl}-phenyl ester is obtained from 3,4-dibromo-2-hydroxybenzaldehyde [CAS-No. 51042-20-7] as a colourless oil.

The following compounds are obtained in analogy to the synthesis described in Example 1:
(7)
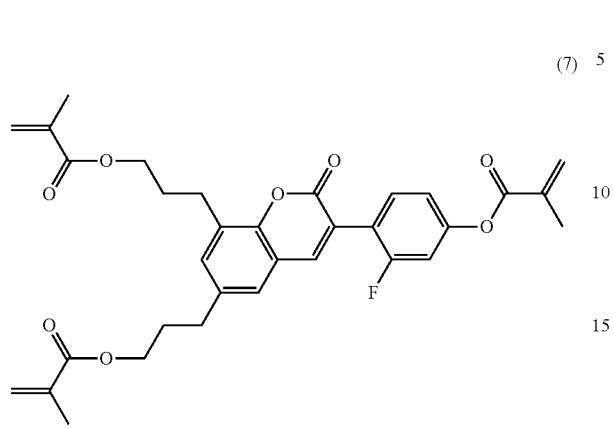
(8)
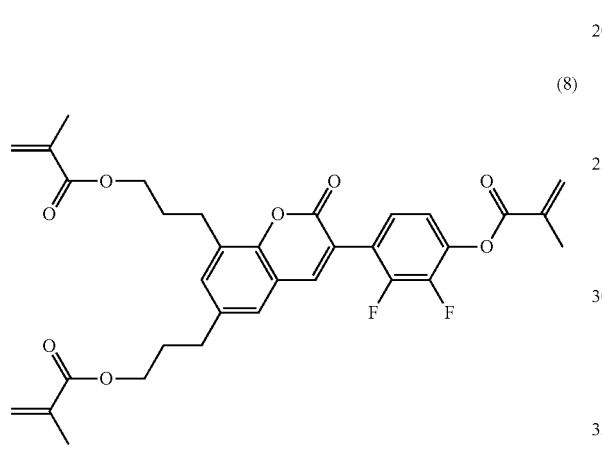
(9)
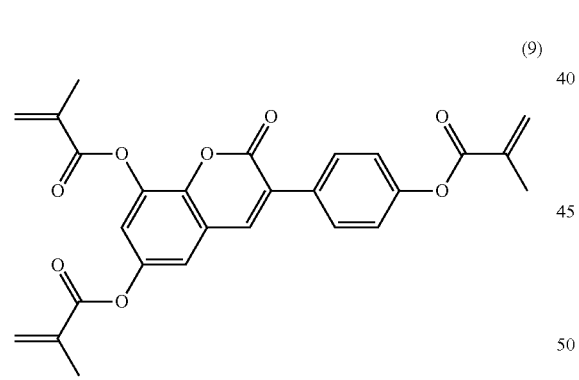
(10)
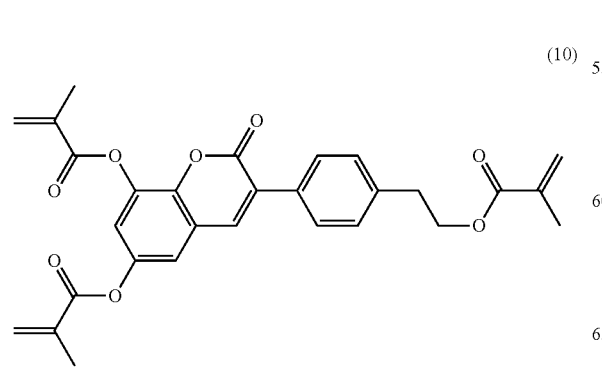
-continued
(11)
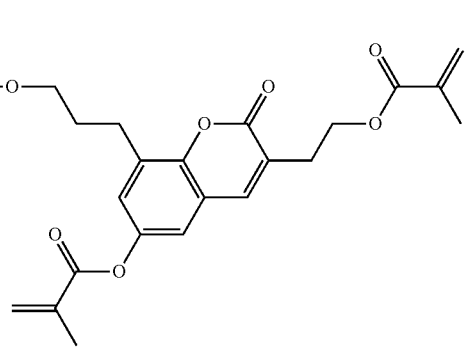
(12)
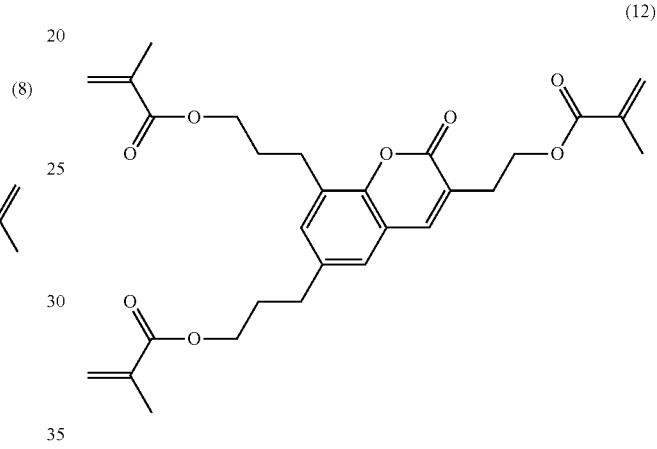
(13)
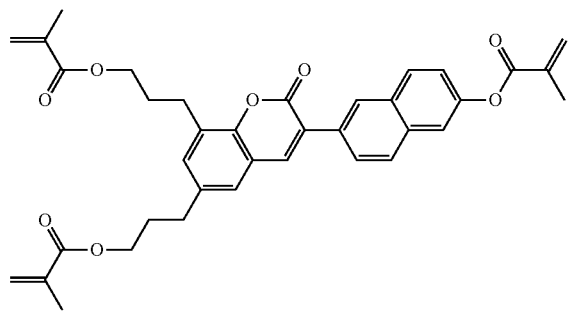
(14)
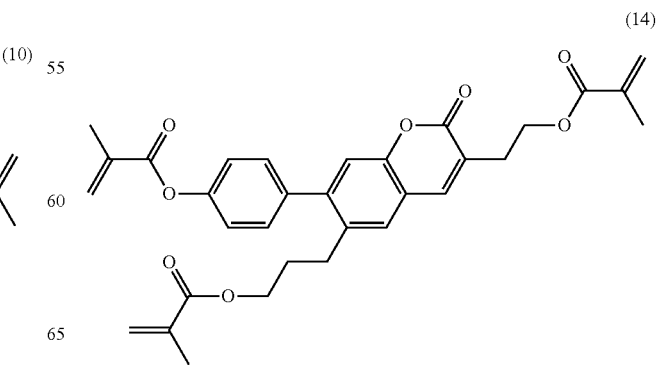

(15)
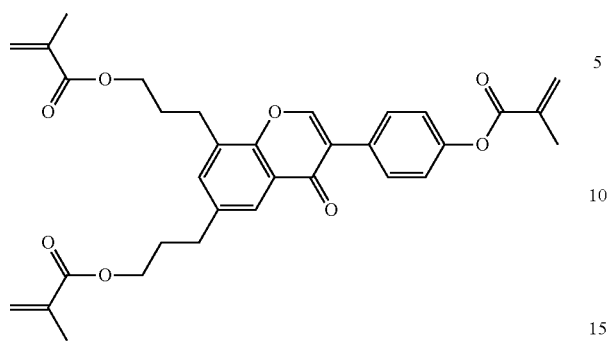
(16)
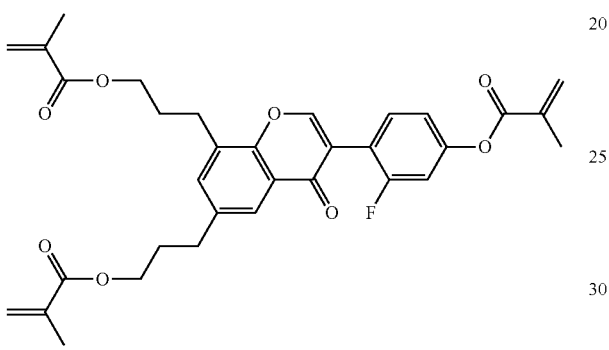
(17)
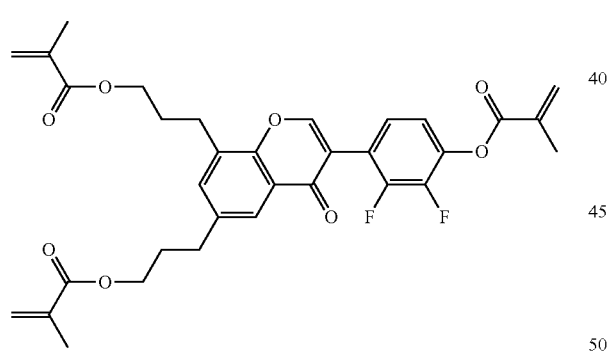
(18)
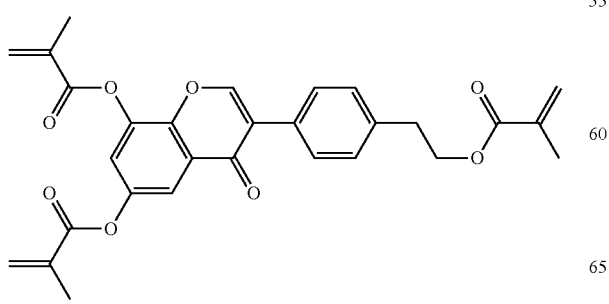
(19)
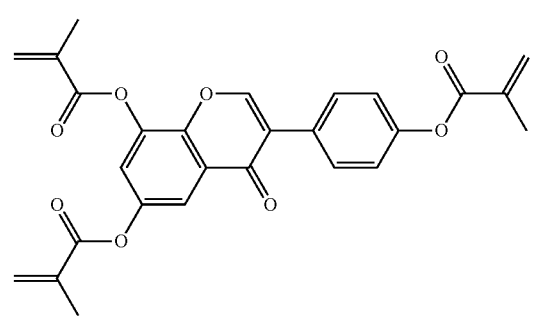
(20)
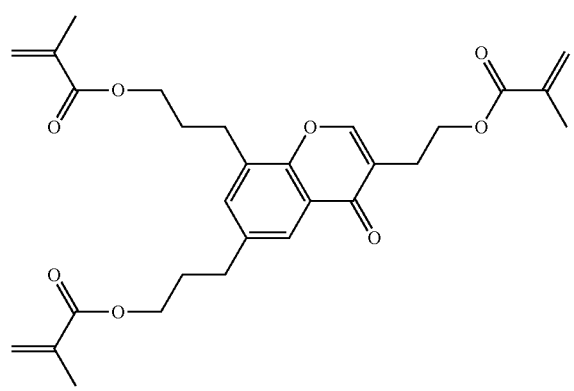
(21)
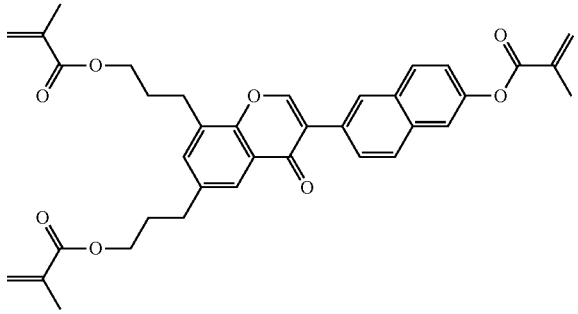
(22)
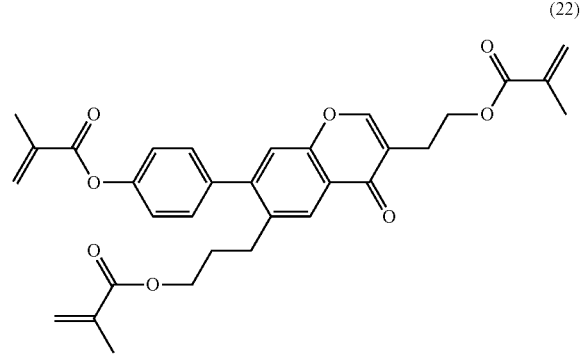

-continued (23)

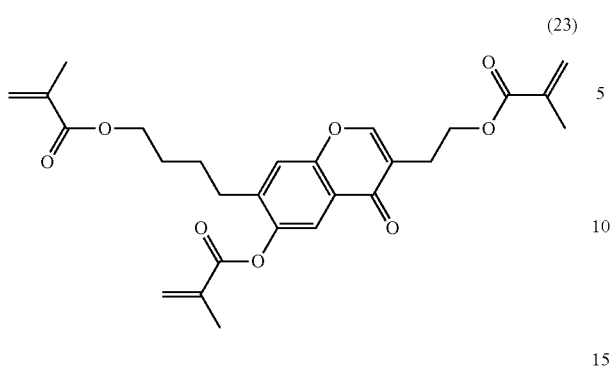

Mixture Example A

The nematic LC mixture N1 is formulated as follows.

| CY-3-O2 | 18.00% | cl.p. | +74.5 |
|---------|--------|-------|-------|
| CPY-2-O2 | 10.00% | Δn | 0.1021 |
| CPY-3-O2 | 10.00% | Δε | −3.1 |
| CCY-3-O2 | 9.00% | $\varepsilon_{\parallel}$ | 3.5 |
| CCY-4-O2 | 4.00% | $K_3/K_1$ | 1.16 |
| CC-3-V | 40.00% | $\gamma_1$ | 86 |
| PYP-2-3 | 9.00% | $V_0$ | 2.29 |

For each measured sample, the polymerisable monomeric compound (1) or (2) from Example 1 or 2, respectively (hereinafter referred to as monomer M1 or M2, see below), is added to the LC mixture N1 at a concentration of 0.3% by weight. Each resultant polymerisable mixture is inserted into a VA e/o test cell (rubbed antiparallel, VA-polyimide alignment layer, LC-layer thickness d≈4 μm). The cells are irradiated with UV light having an intensity of 100 mW/cm² for the time indicated with application of a voltage of 24 V (alternating current), causing polymerisation of the monomeric compound. The tilt angle is determined before and after UV irradiation by a crystal rotation experiment (Autronic-Melchers TBA-105).

M1

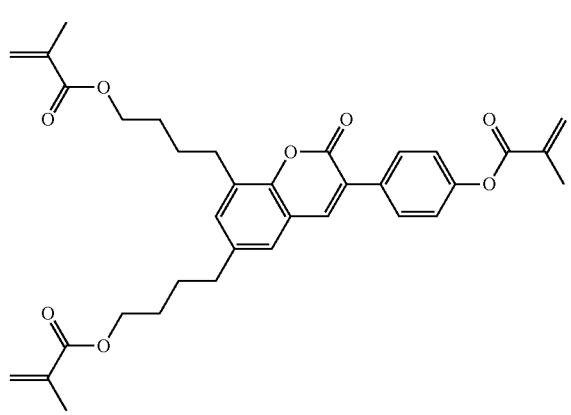

M2

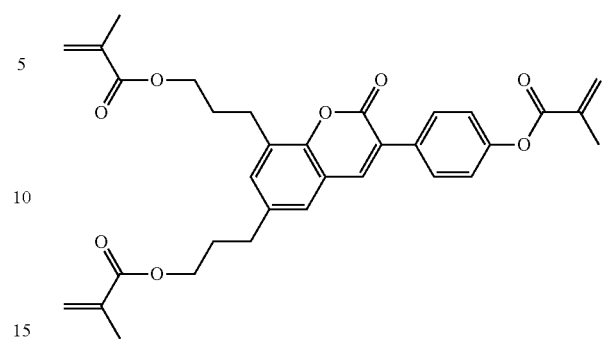

In order to determine the polymerisation rate, the residual content of unpolymerised RM (in % by weight) in the test cells is measured by HPLC after various exposure times. For this purpose each mixture is polymerised in the test cell under the stated conditions. The mixture is then rinsed out of the test cell using MEK (methyl ethyl ketone) and measured.

In addition, the VHR values of the polymerisable LC mixtures comprising N1 and monomer M1 or M2, respectively, are before and after UV exposure are measured as described above.

For comparative purposes, the experiments as described above are also carried out with monomer C1 of prior art.

C1

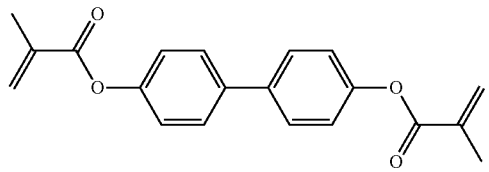

The tilt-angle results for monomers M1, M2 and C1 in N1 are shown in Table 1. The residual concentrations of monomer M1, M2 and C1 in N1 after different exposure times are shown in Table 2. The VHR values of mixtures containing N1 together with M1, M2 or C1 are shown in Table 3.

TABLE 1

| | (t = exposure time) | | |
|---|---|---|---|
| | C1 | M1 | M2 |
| t/s | | Tilt angle/° | |
| 0 | 88.8 | 89.0 | 89.2 |
| 30 | — | 82.2 | 82.1 |
| 60 | — | 77.5 | 76.1 |
| 120 | 77.2 | 74.3 | 73.5 |
| 240 | 72.1 | 71.2 | 71.8 |
| 360 | 70.3 | 71.4 | 70.5 |

TABLE 2

| | (t = exposure time) | | |
|---|---|---|---|
| | C1 | M1 | M2 |
| t/s | | RM concentration/% | |
| 0 | 0.300 | 0.300 | 0.300 |
| 20 | — | 0.164 | 0.138 |

TABLE 2-continued (t = exposure time)

| t/s | C1 | M1 | M2 |
|---|---|---|---|
| | | RM concentration/% | |
| 40 | — | 0.0375 | 0.027 |
| 60 | — | 0.035 | 0.015 |
| 90 | — | 0.061 | 0.008 |
| 120 | 0.1105 | 0.009 | 0.0055 |
| 180 | — | — | 0 |
| 360 | 0.067 | — | — |

TABLE 3

(t = exposure time)

| t/s | C1 | M1 | M2 |
|---|---|---|---|
| | | VHR/% | |
| 0 | 98.50 | 98.20 | 97.93 |
| 30 | — | 96.99 | 96.34 |
| 60 | — | 96.57 | 95.96 |
| 90 | — | 96.03 | — |
| 120 | 94.20 | 95.60 | 95.56 |
| 180 | — | 95.14 | — |
| 300 | — | 94.14 | 93.87 |
| 600 | 81.16 | 91.79 | 91.85 |
| 900 | 73.87 | 89.37 | 87.80 |

As can be seen from Table 1, a small tilt angle after polymerisation is achieved more quickly in PSA displays containing monomers M1 and M2 according to the invention, compared to PSA displays containing the monomer C1 from prior art.

As can be seen from Table 2, significantly more rapid and complete polymerisation is achieved in PSA displays containing the monomers M1 and M2 according to the invention, compared to PSA displays containing the monomer C1 from prior art.

As can be seen from Table 3, the VHR values of monomers M1 and M2 according to the invention in LC mixture N1 after UV exposure are significantly higher than the VHR values of monomer C1 in N1.

The invention claimed is:

1. A compound of formula I $$(R^a-(A^1-Z^1)_{n1}-A^2-X^1)_x \text{—[ring with G, O]}$$  I wherein
G denotes $-CM=CR^c-CO-$, $-CO-CR^c=CM-$, $-CR^c=CM-CO-$ or $-CO-CM=CR^c-$,
M denotes $-X^2-A^4-(Z^2-A^3)_{n2}-R^b$,
$A^{1-4}$ each, independently of one another, and on each occurrence identically or differently, denote an aromatic, heteroaromatic, alicyclic or heterocyclic group, which may also contain fused rings, and which is optionally mono- or polysubstituted by L, and $A^2$ and $A^4$ may also denote a single bond,
$X^1$ and $X^2$ each denote a single bond,
$Z^1$ and $Z^2$ each denote a single bond,
$R^{a-c}$ each, independently of one another, and on each occurrence identically or differently, denote P, P-Sp-, H, OH, F, Cl, Br, I, —CN, —NO$_2$, —NCO, —NCS, —OCN, —SCN, SF$_5$ or straight-chain or branched alkyl having 1 to 25 C atoms, in which, in addition, one or more non-adjacent CH$_2$ groups may each be replaced, independently of one another, by —C(R$^{00}$)=C(R$^{00}$)—, —C≡C—, —N(R$^{00}$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I, CN or P-Sp-,
wherein at least two of the radicals R$^a$ denote or contain a group P or P-Sp-,
P denotes on each occurrence, identically or differently, a polymerisable group that is a vinyloxy, acrylate, methacrylate, fluoroacrylate, chloroacrylate, oxetane or epoxy group,
Sp denotes on each occurrence, identically or differently, a spacer group or a single bond,
R$^{00}$ and R$^{000}$ each, independently of one another, denote H or alkyl having 1 to 12 C atoms,
L denotes on each occurrence, identically or differently, an unpolymerizable group that is F, Cl, CN, or straight-chain or branched C$_{1-25}$-alkyl in which one or more non-adjacent CH$_2$ groups optionally is replaced, independently of one another, by —C(R$^{00}$)=C(R$^{000}$)—, —C≡C—, —N(R$^{00}$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I or CN,
n1 and n2 each, independently of one another, denote 0, 1, 2 or 3,
n3 denotes 1, 2, 3 or 4,
x denotes 2, 3 or 4,
wherein at least one of (a) or (b) is satisfied:
(a) at least one of n1 and n2 is different from 0,
(b) at least one of $A^2$ and $A^4$ is not a single bond.

2. A compound of formula I according to claim 1 of sub-formulae:

$$R^a-(A^1-Z^1)_{n1}-A^2-X^1\text{—[coumarin]}-X^2-A^4-(Z^2-A^3)_{n2}-R^b$$
$$R^a-(A^1-Z^1)_{n1}-A^2-X^1$$  I1

$$R^a-(A^1-Z^1)_{n1}-A^2-X^1\text{—[coumarin]}-X^2-A^4-(Z^2-A^3)_{n2}-R^b$$
$$R^a-(A^1-Z^1)_{n1}-A^2-X^1$$  I2

$$R^a-(A^1-Z^1)_{n1}-A^2-X^1\text{—[coumarin]}-X^2-A^4-(Z^2-A^3)_{n2}-R^b$$
$$R^a-(A^1-Z^1)_{n1}-A^2-X^1$$  I3

$$R^a-(A^1-Z^1)_{n1}-A^2-X^1\text{—[coumarin]}-X^2-A^4-(Z^2-A^3)_{n2}-R^b$$
$$R^a-(A^1-Z^1)_{n1}-A^2-X^1$$  I4

-continued

I5
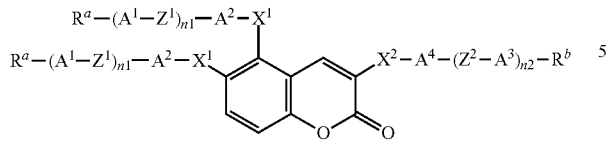

I6
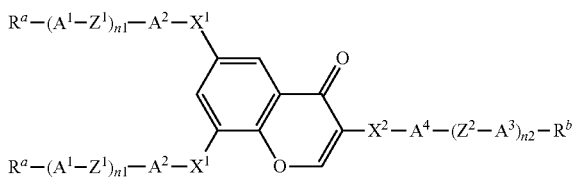

I7
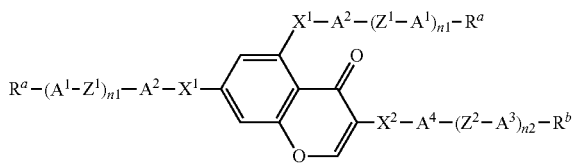

I8
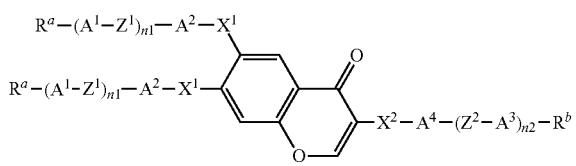

I9
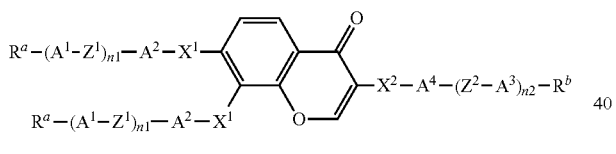

I10
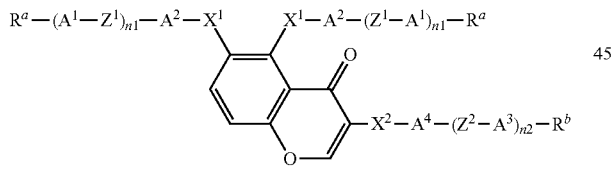

I11
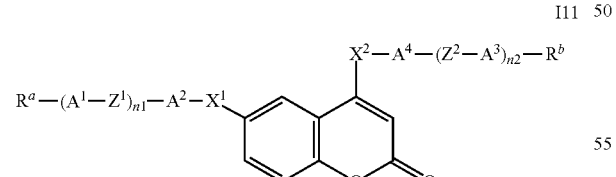

I12
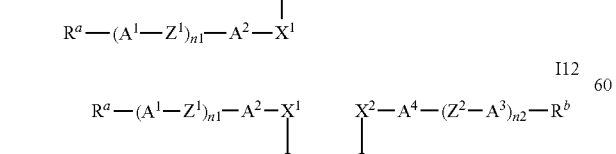

-continued

I13
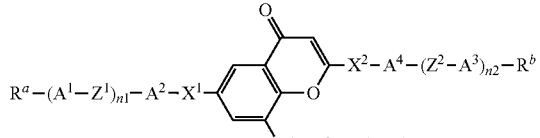

or

I14
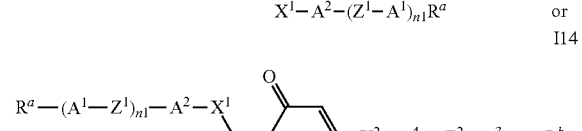

3. The compound according to claim 2, wherein at least one of the aromatic, heteroaromatic, alicyclic or heterocyclic groups $A^{1-4}$ is 1,4-phenylene or naphthalene-2,6-diyl, in which one or two CH groups are optionally replaced by N, and which are optionally mono- or polysubstituted by L.

4. The compound according to claim 2, wherein n1=n2=0, and one of $A^2$ and $A^4$ is a single bond and the other is 1,4-phenylene or naphthalene-2,6-diyl, in which one or two CH groups are optionally replaced by N, and which are optionally mono- or polysubstituted by L.

5. A compound of formula I according to claim 1 of the following sub-formulae:

I1a
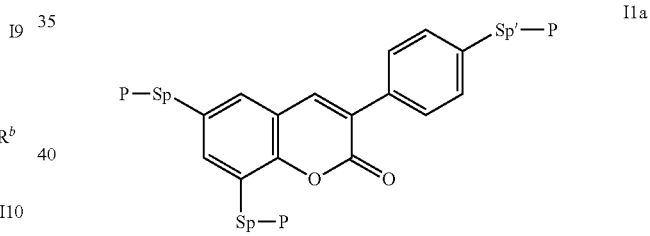

I1b
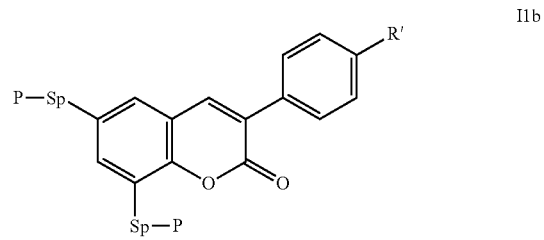

I1c
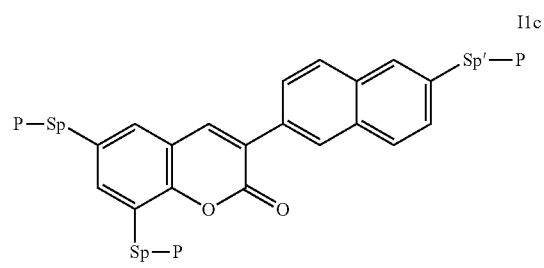

I2a
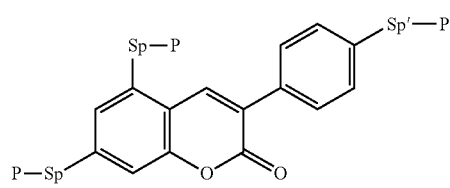
I2b
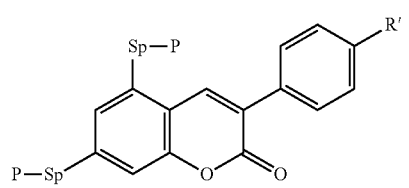
I2c
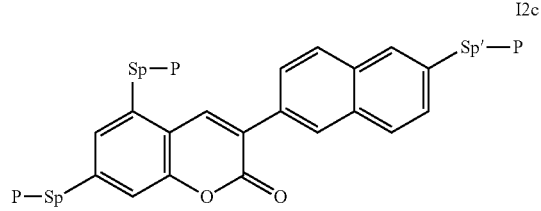
I2d
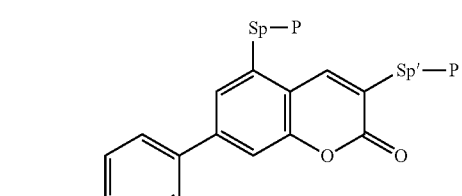
I3a
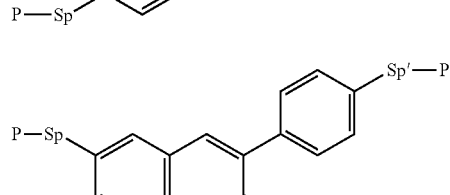
I3b
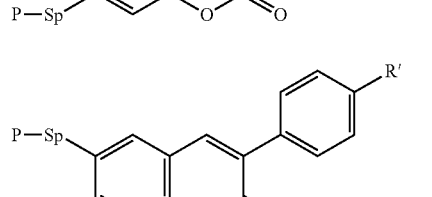
I3c
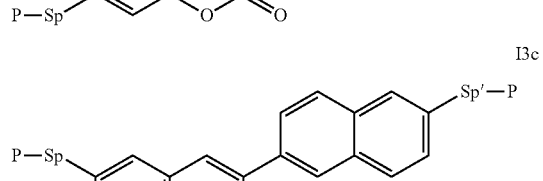
I3d
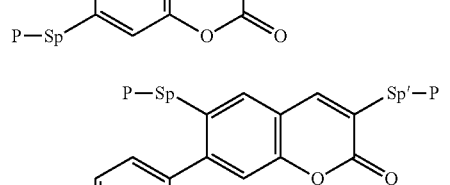
I4a
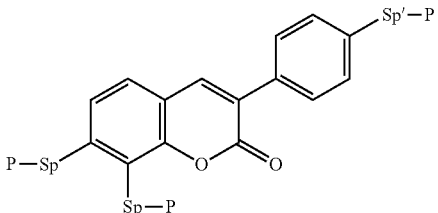
I4b
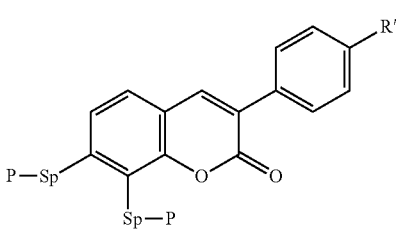
I4c
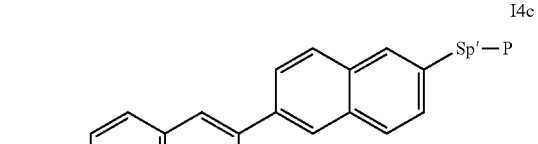
I4d
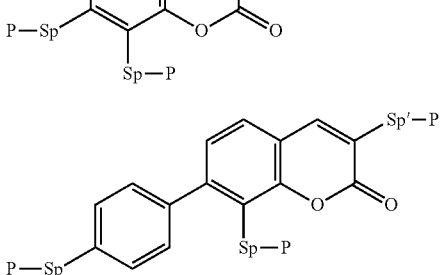
I5a
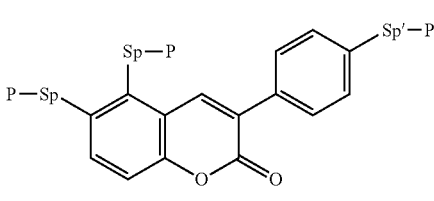
I5b
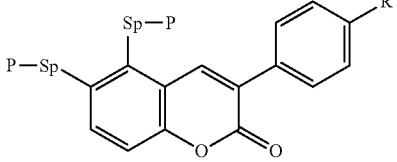
I5c
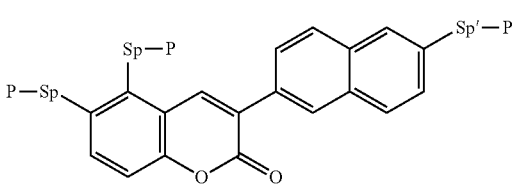
I6a
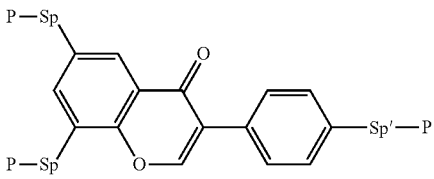

I6b
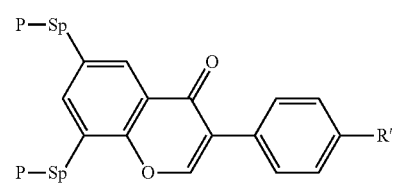
I6c
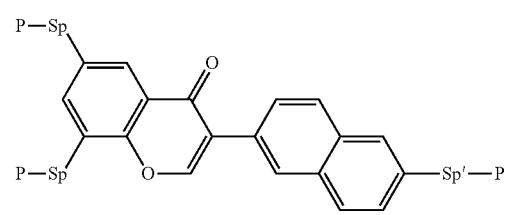
I7a
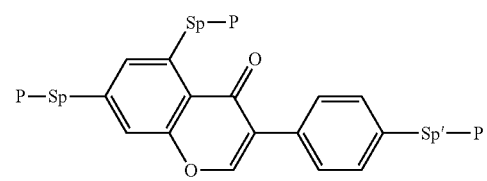
I7b
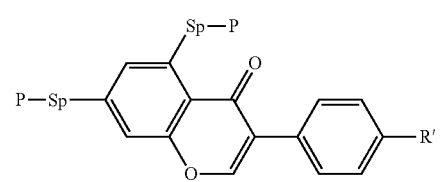
I7c
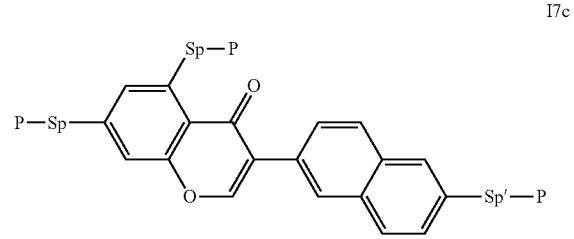
I8a
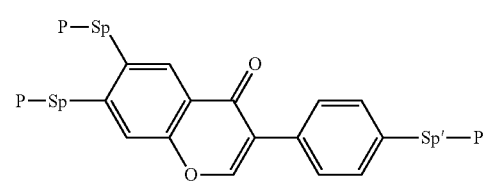
I8b
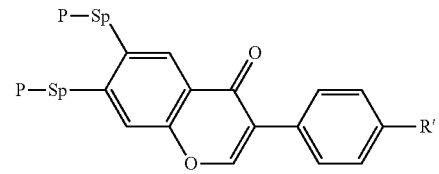
I8c
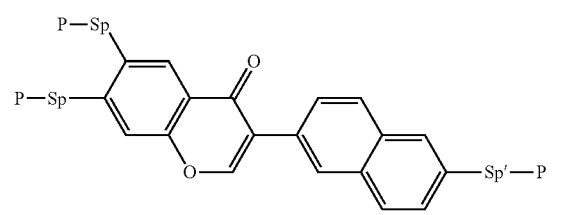
I8d
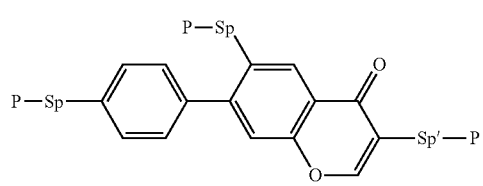
I9a
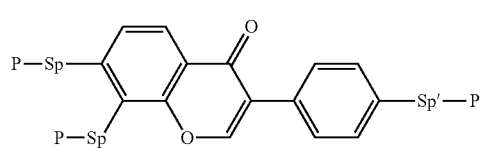
I9b
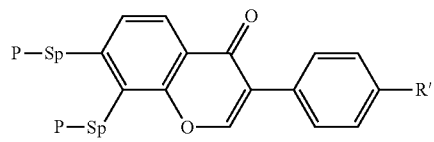
I9c
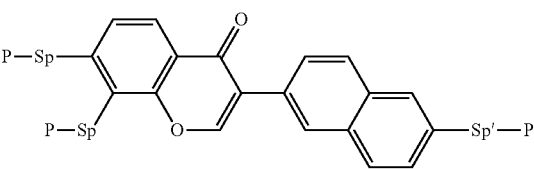
I10a
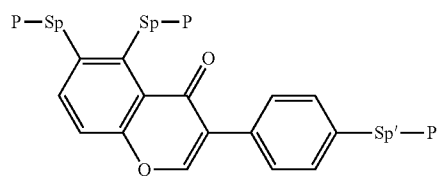
I10b
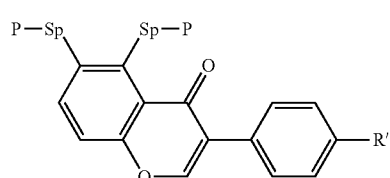
I10c
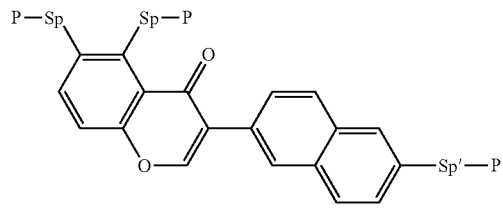
I11a
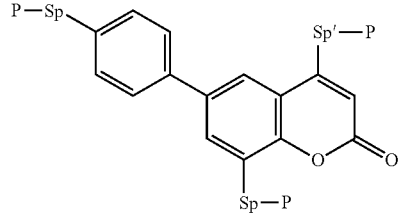

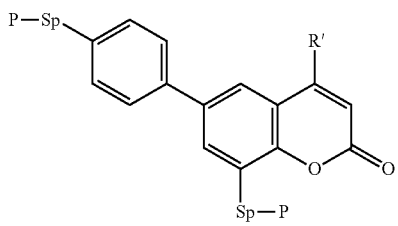

I11b

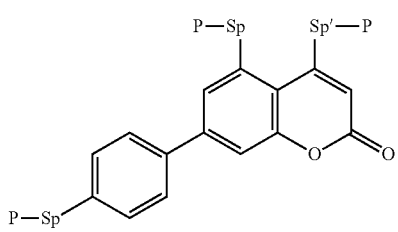

I12a

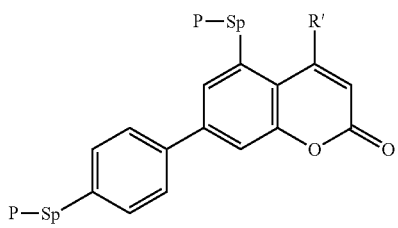

I12b

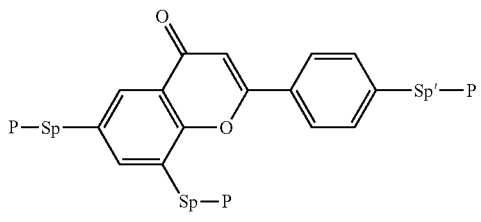

I13a

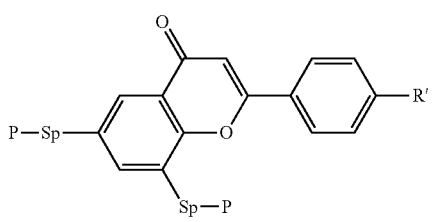

I13b

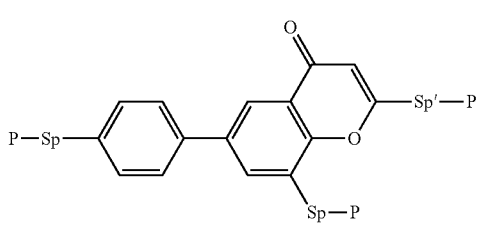

I13c

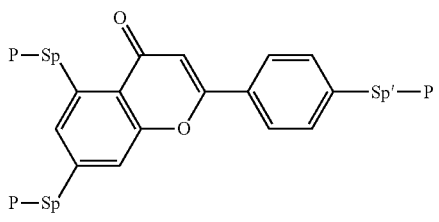

I14a

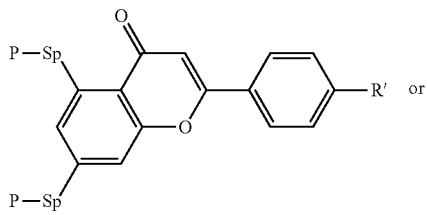

I14b

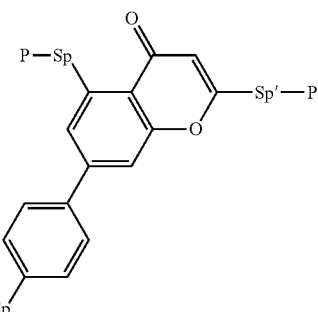

I14c in which Sp' has one of the meanings given for Sp, and is identical to or different from Sp, R' has one of the meanings indicated for $R^b$ which is different from H, P- and P-Sp-, and the phenylene and naphthalene groups are optionally substituted with one, two, three of four F atoms.

6. The compound according to claim 5, which is of one of the following formulae: I1a, I2a, I3a, I4a, I5a, I6a, I7a, I8a, I9a, I10a, I11a, I12a, I13a or I14a.

7. The compound according to claim 5, which is of one of the following formulae: I1b, I2b, I3b, I4b, I5b, I6b, I7b, I8b, I19b, I10b, I11b, I12b, I13b or I14b.

8. The compound according to claim 5, which is of one of the following formulae: I1c, I2c, I3c, I4c, I5c, I6c, I7c, I8c, I9c, I10c, I13c or I14c.

9. The compound according to claim 5, which is of one of the following formulae: I2d, I3d, I4d or I8d.

10. The compound according to claim 1, wherein the aromatic, heteroaromatic, alicyclic or heterocyclic groups $A^{1-4}$ has 4 to 25 C atoms.

11. The compound according to claim 1, wherein at least one of the aromatic, heteroaromatic, alicyclic or heterocyclic groups $A^{1-4}$ is 1,4-phenylene or naphthalene-2,6-diyl, in which one or two CH groups are optionally replaced by N, and which are optionally mono- or polysubstituted by L.

12. The compound according to claim 1, wherein n1=n2=0, and one of $A^2$ and $A^4$ is a single bond and the other is 1,4-phenylene or naphthalene-2,6-diyl, in which one or two CH groups are optionally replaced by N, and which are optionally mono- or polysubstituted by L.

13. A process for the preparation of a compound according to claim 1, in which $R^a$ and $R^b$ are each P-Sp, by esterification or etherification of a compound of formula I*

I*

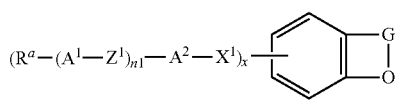

G denotes -CM=$CR^c$—CO—, —CO—$CR^c$=CM-, —$CR^c$=CM-CO— or —CO-CM=$CR^c$—

M denotes —X²-A⁴-(Z²-A³)$_{n2}$-R$^b$,

A$^{1-4}$ each, independently of one another, and on each occurrence identically or differently, denote an aromatic, heteroaromatic, alicyclic or heterocyclic group, which may also contain fused rings, and which is optionally mono- or polysubstituted by L, and A² and A⁴ may also denote a single bond, X¹ and X² each denote a single bond, Z¹ and Z² each denote a single bond, R$^c$ each, independently of one another, and on each occurrence identically or differently, denote P, P-Sp-, H, OH, F, Cl, Br, I, —CN, —NO₂, —NCO, —NCS, —OCN, —SCN, SF₅ or straight-chain or branched alkyl having 1 to 25 C atoms, in which, in addition, one or more non-adjacent CH₂ groups may each be replaced, independently of one another, by —C(R$^{00}$)=C(R$^{000}$)—, —C≡C—, —N(R$^{00}$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I, CN or P-Sp-, wherein at least two of the radicals R$^a$ denote or contain a group P or P-Sp-, P denotes on each occurrence, identically or differently, an acrylate or a methacrylate group, Sp denotes on each occurrence, identically or differently, a spacer group or a single bond, R$^{00}$ and R$^{000}$ each, independently of one another, denote H or alkyl having 1 to 12 C atoms, L denotes on each occurrence, identically or differently, P-Sp-, H, OH, CH₂OH, halogen, SF₅, NO₂, a carbon group or hydrocarbon group, n1 and n2 each, independently of one another, denote 0, 1, 2 or 3, n3 denotes 1, 2, 3 or 4, x denotes 2, 3 or 4, wherein at least one of (a) or (b) is satisfied:

(a) at least one of n1 and n2 is different from 0, (b) at least one of A² and A⁴ is not a single bond, R$^a$ and R$^b$ denote -Sp-O—Sg, and Sg denotes an H atom or a protecting group, using, in case P is a methacrylate group, methacryloyl chloride or methacrylic anhydride or a methacrylic acid derivative in the presence of a base, or methacrylic acid in the presence of a dehydrating reagent, or in case P is an acrylate group, acryloyl chloride or acrylic anhydride or an acrylic acid derivative in the presence of a base, or acrylic acid in the presence of a dehydrating reagent.

14. The process according to claim 13, wherein the compound of the formula I* is I*7a
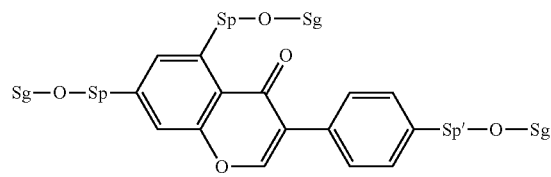
I*8a
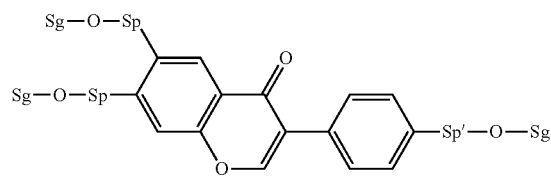
I*8b
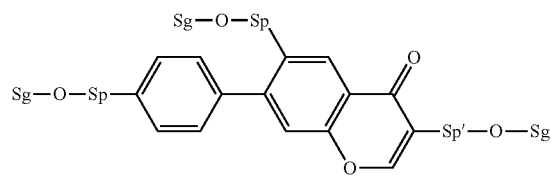
I*9a
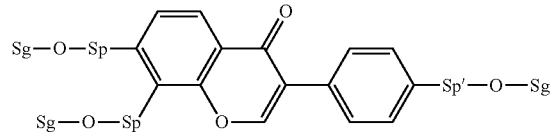
I*10a
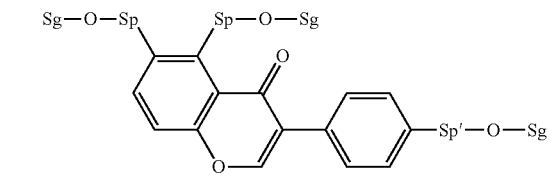
I*11a
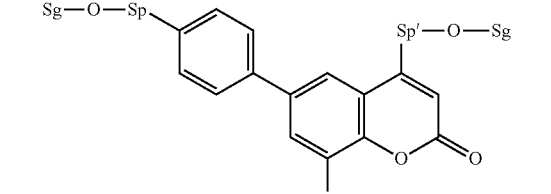
I12*a
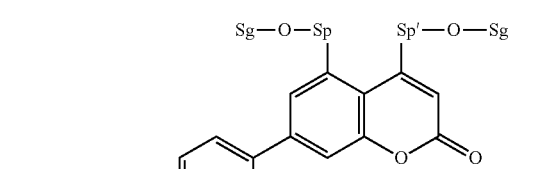
I13*a
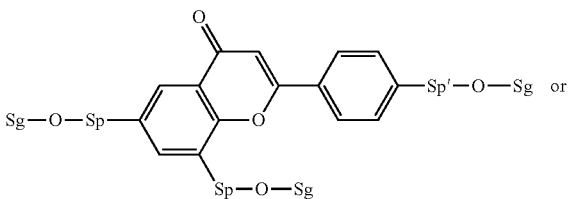 or
I14*a
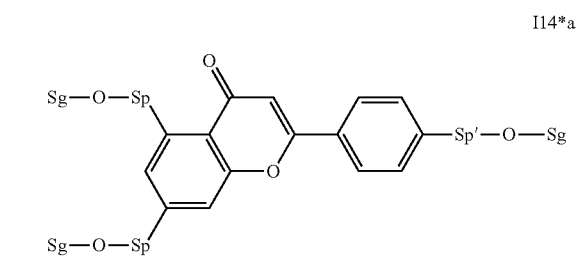
wherein each Sp' independently has one of the meanings of Sp.
15. The process according to claim 13, wherein the aromatic, heteroaromatic, alicyclic or heterocyclic groups $A^{1-4}$ has 4 to 25 C atoms.
16. A compound of the formula:
I*1a
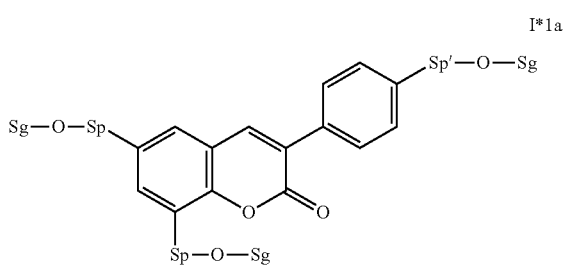
I*1b
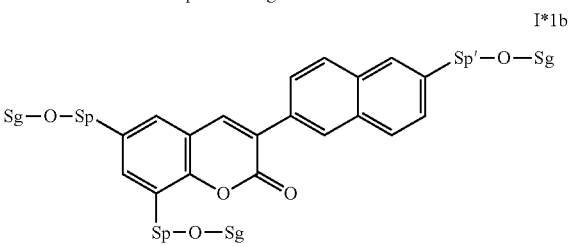
I*2a
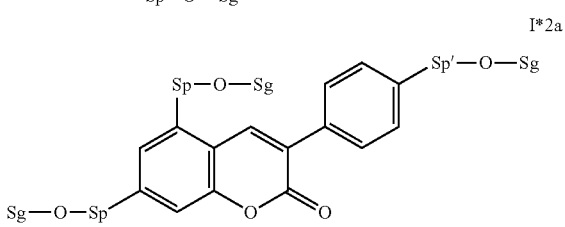
I*3a
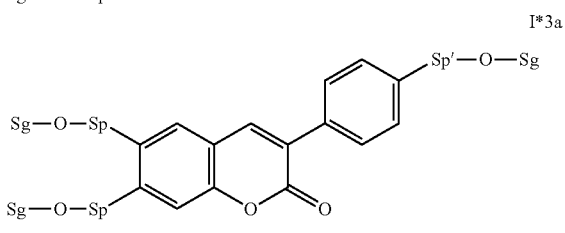

-continued

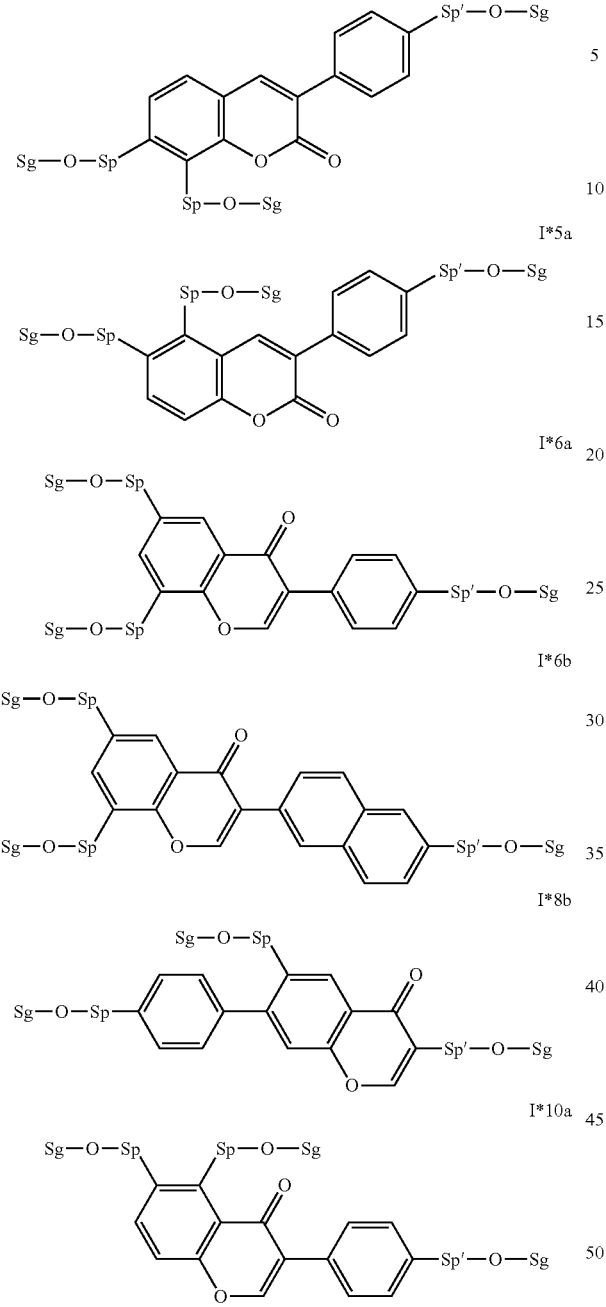

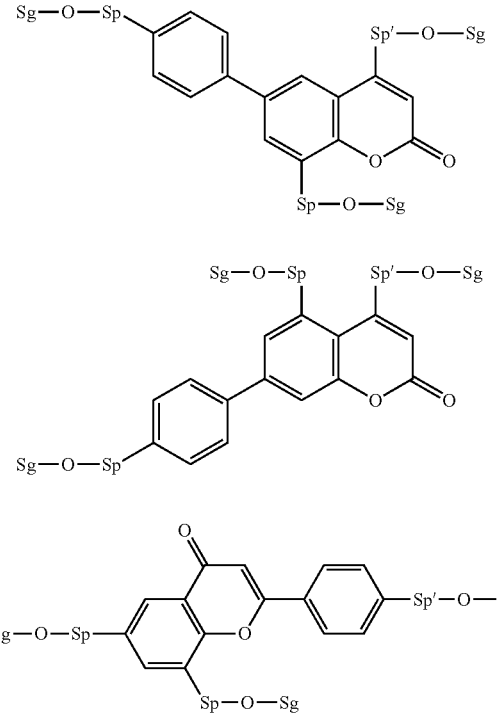

wherein

Sg denotes an H atom or a protecting group,

Sp each, denotes on each occurrence, identically or differently, a spacer group or a single bond, and Sp' each, independently has one of the meanings of Sp, wherein in each compound one or more of the radicals Sp and Sp' denote a single bond and one or more of the radicals Sp and Sp' are not a single bond.

17. The compound according to claim 16, which is of one of the following formulae: I*1a, I*5a, I*6a, I*8b, I* 10a, I11*a or I12*a.

18. The compound according to claim 16, which is of one of the following formulae: I* 1b or I*6b.

19. The compound according to claim 16, which is of one of the following formulae: I*2a, I*3a, or I*4a.

20. The compound according to claim 16, which is of formula I13*a.

* * * * *